US010016402B2

(12) United States Patent
Zon et al.

(10) Patent No.: US 10,016,402 B2
(45) Date of Patent: Jul. 10, 2018

(54) METHODS FOR TREATMENT OF MELANOMA

(71) Applicants: CHILDREN'S MEDICAL CENTER CORPORATION, Boston, MA (US); DANA-FARBER CANCER INSTITUTE, INC., Boston, MA (US)

(72) Inventors: Leonard Zon, Wellesley, MA (US); Richard M. White, Cambridge, MA (US)

(73) Assignees: CHILDREN'S MEDICAL CENTER CORPORATION, Boston, MA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 14/733,498

(22) Filed: Jun. 8, 2015

(65) Prior Publication Data
US 2015/0306080 A1   Oct. 29, 2015

Related U.S. Application Data

(63) Continuation-in-part of application No. 13/983,090, filed as application No. PCT/US2012/024295 on Feb. 8, 2012, now abandoned.

(60) Provisional application No. 61/440,475, filed on Feb. 8, 2011.

(51) Int. Cl.
| A61K 31/44 | (2006.01) |
| A61K 31/196 | (2006.01) |
| A61K 31/437 | (2006.01) |
| A61K 45/06 | (2006.01) |
| A61K 31/381 | (2006.01) |
| A61K 31/42 | (2006.01) |

(52) U.S. Cl.
CPC ............ *A61K 31/44* (2013.01); *A61K 31/196* (2013.01); *A61K 31/381* (2013.01); *A61K 31/42* (2013.01); *A61K 31/437* (2013.01); *A61K 45/06* (2013.01)

(58) Field of Classification Search
CPC .... A61K 31/44; A61K 31/196; A61K 31/381; A61K 31/42; A61K 31/437; A61K 45/06
USPC ........................................................ 514/300
See application file for complete search history.

(56) References Cited

U.S. PATENT DOCUMENTS

| 5,763,441 | A | 6/1998 | App et al. |
| 7,074,831 | B2 | 7/2006 | Jonsson et al. |
| 7,176,241 | B2 | 2/2007 | Leban et al. |
| 2004/0192758 | A1 | 9/2004 | Leban et al. |
| 2006/0199856 | A1 | 9/2006 | Leban et al. |
| 2006/0199859 | A1 | 9/2006 | Dees et al. |
| 2007/0254295 | A1 | 11/2007 | Harvey et al. |
| 2009/0192158 | A1 | 7/2009 | Kargman et al. |
| 2010/0004304 | A1 | 1/2010 | Kohn et al. |
| 2010/0074898 | A1 | 3/2010 | Castro Palomino Laria et al. |
| 2012/0294854 | A1 | 11/2012 | Castro Palomino Laria et al. |
| 2014/0031383 | A1 | 1/2014 | Zon et al. |
| 2014/0121235 | A1 | 5/2014 | Xu |

FOREIGN PATENT DOCUMENTS

| JP | 2006265117 | | 10/2006 |
| WO | 9521613 | | 8/1995 |
| WO | WO 2008/077639 | * | 7/2008 |
| WO | WO 2012/052179 | * | 4/2012 |
| WO | 2012/109329 A2 | | 8/2012 |

OTHER PUBLICATIONS

Ko et al. A new era: melanoma genetics and therapeutics. Journal of Pathology, 2011; 223: 241-250.*
Tsai et al. Discovery of a selective inhibitor of oncogenic B-raf kianse with potent antimelanoma activity. PNAS, Feb. 26, 2008. vol. 105, No. 8, pp. 3041-3046.*
White et al. DHODH modulates transcriptional elongations in the neural crest and melanoma. Nature, vol. 471, Mar. 24, 2011.*
Chen et al. Transplant Immunology, 2010, 23(4) 180-184 (Year: 2010).*
Dhomen et al. "BRAF Signaling and Targeted Therapies in Melanoma" Hematology-Oncology Clinics of North America, WB Saunders, U.S. 23(3)529-545 (2009).
Dorwald (Side Reactions in Organic Synthesis: A Guide to Successful Design, Weinheim: WILEY-VCH Verlag GmbH & Co. KGaA, Preface (2005).
Eckhardt et al., "Phase I and pharmacologic study of the tyrosine kinase inhibitor SU101 in patients with advanced solid tumors." Jounal of Clinical Oncology 17(4):1095-1104 (1999).
Flaherty et al. "Inhibition of mutated, activated BRAF in metastatic melanoma" N. Engl. J. Med. 363:809-819 (2010).
Fritzson et al., Inhibition of human DHODH by 4-hydroxycoumarins, fenamic acids, and N-(alkylcarbonyl) anthranilic acids identified by structure-guided fragment selection. Chem. Med. Chem. 5:6089-617 (2010).
Greene et al. "Inhibition of dihydroorotate dehydrogenase by the immunosuppressive agent leflunomide" Biochemical Pharmacology, Elsevier, US 50(6)861-867 (1995).
Ko et al. "A new era: melanoma genetics and therapeutics," Journal of Pathology 223:241-250 (2011).

(Continued)

*Primary Examiner* — Yevegeny Valenrod
(74) *Attorney, Agent, or Firm* — Nixon Peabody LLP

(57) ABSTRACT

Embodiments of the present invention are directed to methods for treatment of melanoma using an inhibitor of dihydroorotate dehydrogenase (DHODH) and to combination therapies that involve administering to a subject an inhibitor of oncogenic BRAF (e.g. BRAF(V600E)), as well as an inhibitor of dihydroorotate dehydrogenase (DHODH). Assays for identifying compounds useful for the treatment of melanoma are also provided. The methods comprise screening for compounds or agents that inhibit neural crest progenitor formation in a zebra fish model of melanoma.

12 Claims, 39 Drawing Sheets

(56) References Cited

OTHER PUBLICATIONS

McLean et al. "Multiple inhibitor analysis of the brequinar and leflunomide binding sites on human dihydroorotate dehydrogenase" Biochemistry 40:2194-2200 (2001).

Natale et al. "Multicenter phase II trial of brequinar sodium in patients with advanced melanoma" Annals of Oncology, Kluwer, Dordrecht, NL 3(8):659-660 (1992).

Patton et al., "BRAF mutations are sufficient to promote nevi formation and cooperate with p53 in the genesis of melanoma" Curr. Bio. 15:249-254 (2005).

Sosman "PLX4032 draws 70% response in metastatic melanoma: Commentary" Oncology Report, Elsevier Oncology, US, WINT, p. 43 (2009).

Tsai et al., "Discovery of a selective inhibitor of oncogenic B-Raf kinase with potent antimelanoma activity," PNAS 105 (8):3041-3046 (2008).

Wellbrock et al. "BRAF as therapeutic target in melanoma" Biochemical Pharmacology, Elsevier, US 80 (5):561-567 (2010).

White et al. "DHODH modulates transcriptional elongation in the neural crest and melanoma" Nature, Nature Publishing Group GBR 471(7339):518-522 (2011).

Waltenberger et al., "Pharmacophore Modeling and Virtual Screening for Novel Acidic Inhibitors of Microsomal Prostaglandin E2 Synthase-1 (mPGES-1)", J Med Chem, 54: 3163-3174 (2011).

\* cited by examiner

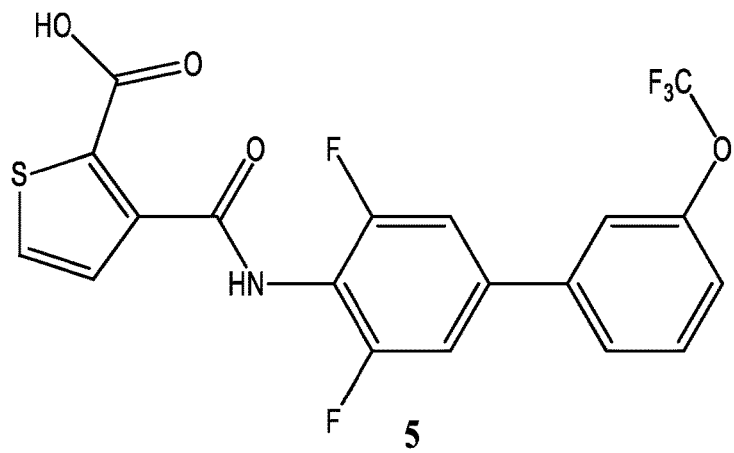
5
Chemical Formula: $C_{19}H_{10}F_5NO_4S$
Molecular Weight: 443.34
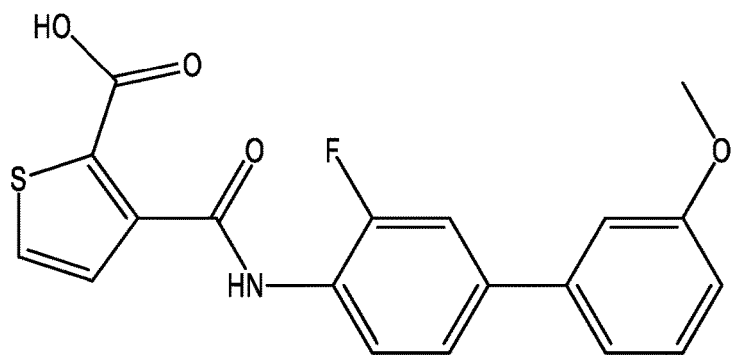
6
Chemical Formula: $C_{19}H_{14}FNO_4S$
Molecular Weight: 371.38
*FIG. 22*

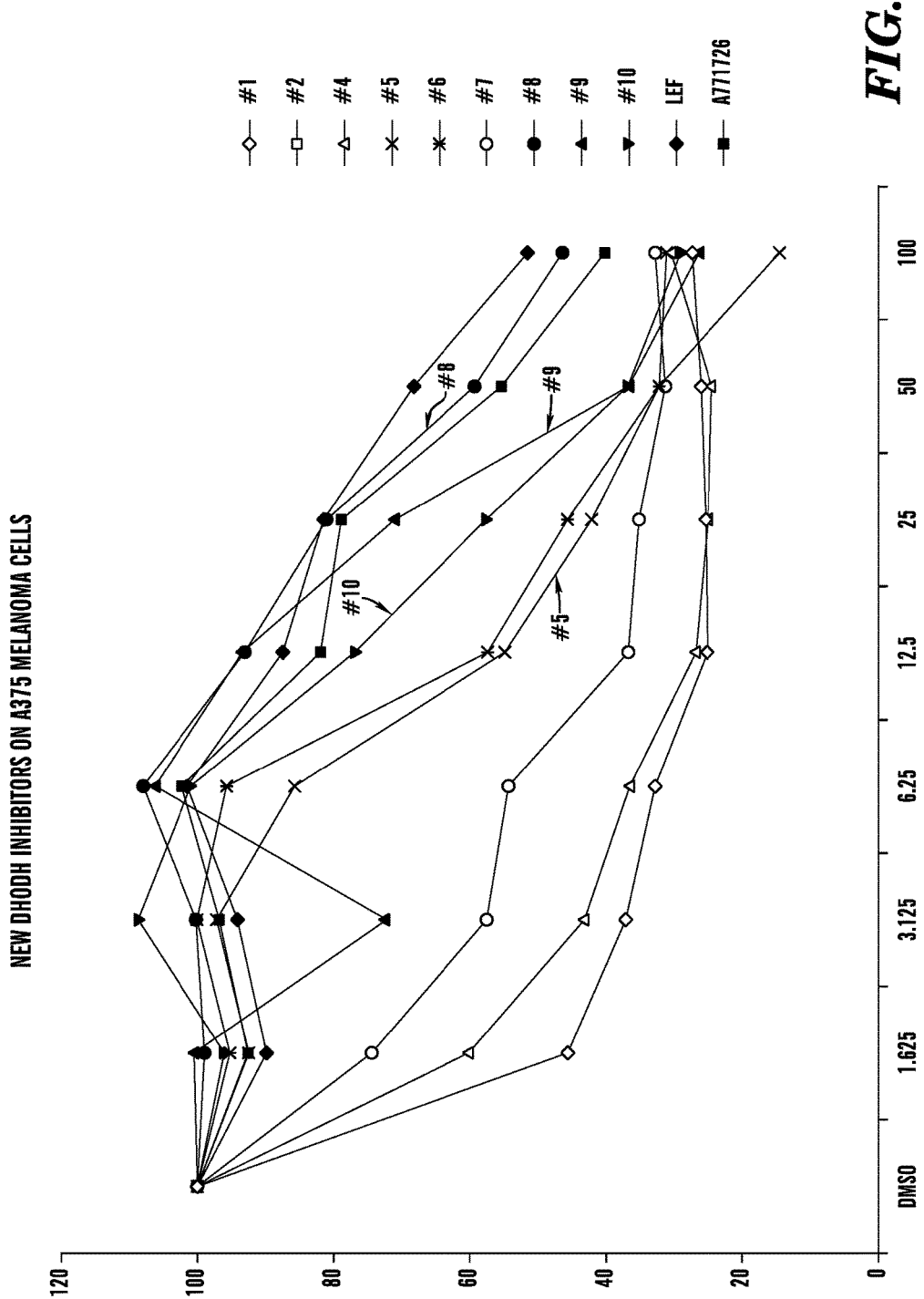

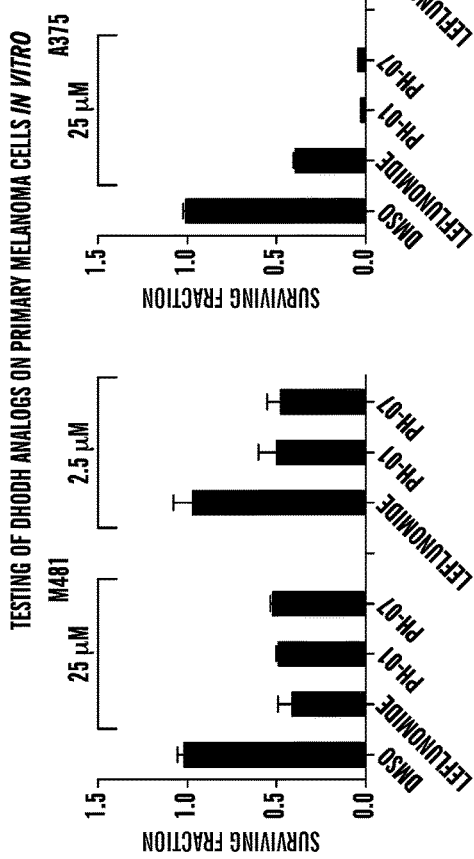
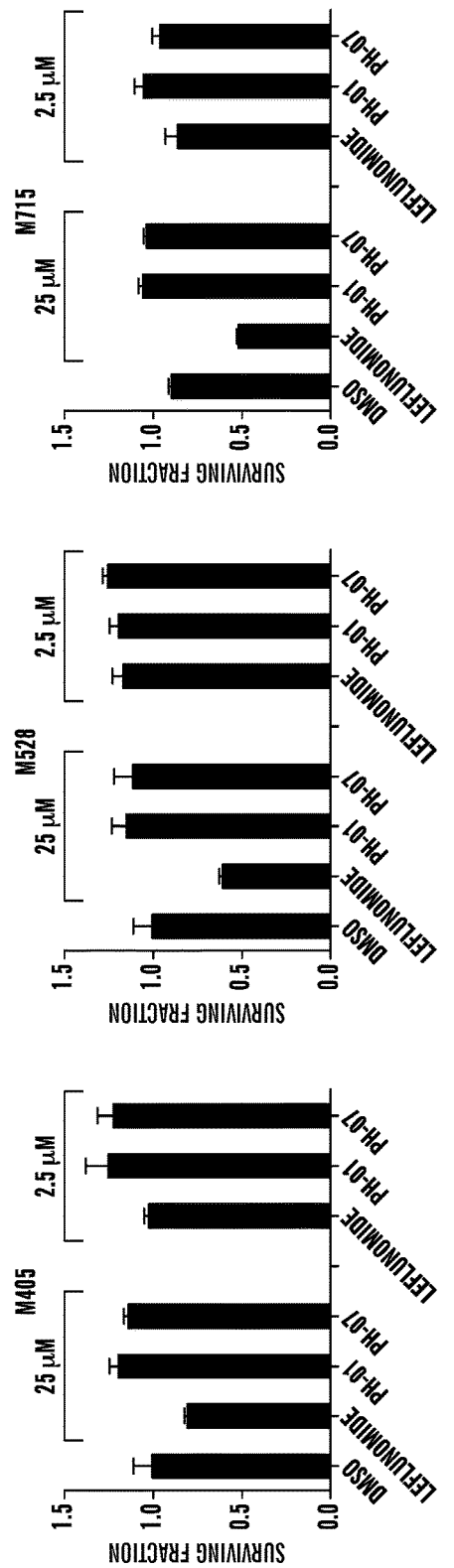

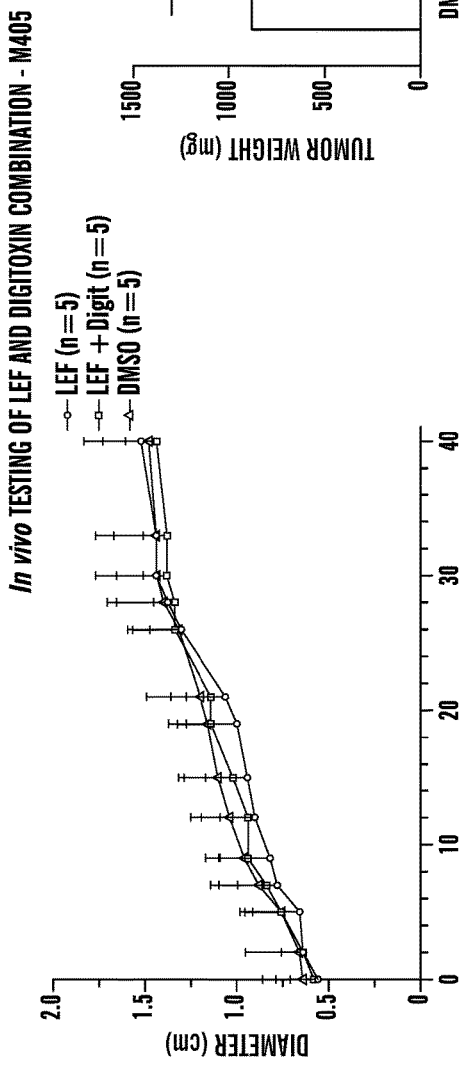
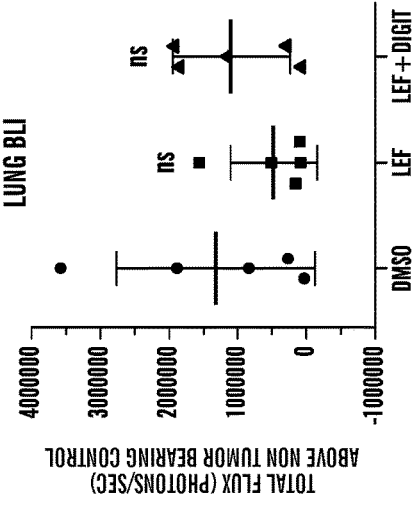
FIG. 29A, FIG. 29B, FIG. 29C, FIG. 29D

METHODS FOR TREATMENT OF MELANOMA

CROSS REFERENCE TO RELATED APPLICATIONS

This Application is a Continuation-in Part Application of U.S. Ser. No. 13/983,090, filed Oct. 4, 2013, which is a 35 U.S.C. 371 National Stage Entry Application of International Application No. PCT/US2012/024295 filed Feb. 8, 2012, which designates the U.S. and claims the benefit under 35 U.S.C. § 119(e) of U.S. Provisional Application No. 61/440,475 filed Feb. 8, 2011, the contents of which are incorporated herein by reference in their entireties.

GOVERNMENT SUPPORT

This invention was made with Government support under Grant No. R01CA103846-09 awarded by the National Institute of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 12, 2016, is named 701039-064585-CIP_SL.txt and is 25,804 bytes in size.

FIELD OF INVENTION

The present invention relates to methods for treatment of melanoma using an inhibitor of dihydroorotate dehydrogenase (DHODH) and to combination therapies that involve administering to a subject an inhibitor of oncogenic BRAF (e.g. BRAF(V600E)), as well as an inhibitor of dihydroorotate dehydrogenase (DHODH). Assays for identifying compounds useful for the treatment of melanoma are also provided. The methods comprise screening for compounds or agents that inhibit neural crest progenitor formation in a zebra fish model of melanoma.

BACKGROUND OF THE INVENTION

Melanoma is a malignant tumor of melanocytes. Primarily melanoma is a skin tumor, but it is also seen, though less frequently, in the melanocytes of the eye (uveal melanoma). Even though it represents one of the rarer forms of skin cancer, melanoma underlies the majority of skin cancer-related deaths and despite many years of intensive laboratory and clinical research, there are still limited treatments for melanoma.

One effective cure for melanoma (prior to metastasis) is surgical resection of the primary tumor before it achieves a thickness of greater than 1 mm. If the tumor is more invasive, surgery can be combined with radiation and/or chemotherapy. Since these conventional modalities cannot cure patients of lethal metastasized tumors, efficacy of alternative treatments such as immunotherapy are being investigated in clinical trials.

Oncogenic BRAF mutations are present in a majority of melanomas and have been implicated in malignant growth of melanoma cells. BRAF(V600E) mutation is the most common oncogenic BRAF mutation found in melanoma cells. Recently, Zelboraf™ (also known as Vemurafenb or PLX4032: Hoffman-La-Roche (Madison Wis.)/Daiichi Sankyo (Parsippany, N.J.)) was approved for treatment of unresectable (inoperable) or metastatic melanoma with a BRAF (V600E) mutation. There have been positive results with Zelboraf™ (Hoffman-La-Roche (Madison Wis.)/Daiichi Sankyo (Parsippany, N.J.)), however resistance is a problem. In addition, there are unwanted side effects, including back pain, constipation, cough, diarrhea, dizziness, dry skin, hair loss, headaches, joint or muscle pain, loss of appetite; nausea, taste changes, thickening of the skin, tiredness, vomiting, and weakness, as well as severe allergic reactions. Thus, treatments for melanoma still need to be improved.

SUMMARY

We have determined by gene expression analysis that melanoma cells adopt a fate similar to multipotent neural crest progenitors. We used zebra-fish embryos to identify the initiating transcriptional events that occur upon activation of oncogenic BRAF(V600E) in the neural crest lineage. Zebrafish embryos that are transgenic for mitfa:BRAF (V660E) and which lack p53 have been found to have a gene signature that is enriched for markers of multipotent neural crest cells, and neural crest progenitors from these embryos fail to terminally differentiate. In particular, we discovered that BRAF(V600E):p53$^{-/-}$ embryos exhibit an abnormal expansion in the number of crestin$^+$ progenitors. Furthermore, in the adult, BRAF(V600E):p53$^{-/-}$ virtually all tumor cells, but no normal cells, are positive for crestin. Thus, we concluded that suppressors of neural crest progenitors may have utility in the treatment of melanoma. Accordingly, we developed a screen to identify inhibitors of the crestin$^+$ lineage during development, allowing for identification of compounds or agents useful for melanoma treatment. We screened a library of 2,000 chemicals for suppressors of neural crest development in BRAF(V600E):p53$^{-/-}$ zebrafish and successfully identified compounds useful in the treatment of melanoma.

Embodiments of the invention are based on the development of a screening assay for inhibitors of melanoma, and on the discovery of one class of compounds, i.e. inhibitors of dihydroorotate dehydrogenase (DHODH), that result in almost complete abrogation of neural crest development in zebrafish. In particular, we have determined that inhibitors of DHODH, when used alone or in combination with an inhibitor of the BRAF oncogene (e.g. BRAF(V600E)), decrease melanoma growth both in vitro and in vivo in mouse xenograft studies. The combination therapy required only subclinical doses of each compound suggesting that there may be therapeutic synergy. Unexpectedly, 40% of the treated mice had complete regression of tumors using a combination of the specific oncogenic BRAF(V600E) inhibitor PLX4720 (Plexxikon Inc., Berkeley, Calif., USA) and the DHODH inhibitor Leflunomide (Arava™ Sanofi-Aventis (Paris, France), which led abrogation of tumor growth in nude mice transplanted with A375 human melanoma cells.

We have also determined that many other inhibitors of DHODH, e.g. when tested in zebra fish, on human A375 melanoma cells and in primary tumor xenographs, when used alone or in combination with an inhibitor of the BRAF oncogene (e.g. BRAF(V600E)), decrease melanoma growth both in vitro and in vivo. In particular, see the compounds of FIG. 21, FIG. 22 and FIG. 23, which are labeled 1-10 and Example III.

Accordingly, provided herein are methods for treatment of melanoma comprising administrating to a subject (diagnosed with, or at risk of having melanoma), an inhibitor of DHODH. Also provided is a combination therapy for treatment of melanoma that involves administrating an effective amount of an inhibitor of DHODH and an effective amount of an inhibitor of oncogenic BRAF (e.g. BRAF(V600E) oncogene), where the inhibitors are administered simultaneously, or sequentially. Methods of screening for agents that inhibit melanoma growth are also described.

In one aspect of the invention, a method for treating melanoma in a subject is provided, which comprises administering to a subject in need thereof a therapeutically effective amount of an inhibitor of dihydroorotate dehydrogenase (DHODH) (e.g. a small molecule, a nucleic acid RNA, a nucleic acid DNA, a protein, a peptide, or an antibody). In one embodiment, the inhibitor of dihydroorotate dehydrogenase (DHODH) is selected from the group consisting of: leflunomide, teriflunomide, brequinar, dichloroallyl lawsone, maritimus, redoxal and NSC210627, or a derivative thereof. In one embodiment, the DHODH inhibitor is selected from the group consisting of $C_{19}H_{14}F_2N_2O_3$, compound 1; $C_{20}H_{16}F_2N_2O_3$, compound 2; $C_{18}H_{13}F_6NO_4$, compound 3; $C_{19}H_{16}F_3NO_4$, compound 4; $C_{19}H_{10}F_5NO_4S$, compound 5; $C_{19}H_{14}FNO_4S$, compound 6; $C_{20}H_{15}F_4NO_4$, compound 7; $C_{19}H_{17}NO_4$, compound 8; $C_{20}H_{17}F_2NO_4$, compound 9; and $C_{20}H_{18}FNO_4$, compound 10, each as depicted in FIG. 21, FIG. 22 and FIG. 23.

In another aspect of the invention, a combination therapy for treating melanoma is provided. The method comprises administering to a subject in need thereof a therapeutically effective amount of an inhibitor of dihydroorotate dehydrogenase (DHODH) and an effective amount of an inhibitor of oncogenic BRAF. The inhibitors may be a small molecule, a nucleic acid RNA, a nucleic acid DNA, a protein, a peptide, or an antibody. The inhibitors (compounds/agents) may be administered simultaneously, or sequentially. In one embodiment, each inhibitor is administered within minutes, within hours, or within days, of one another.

Any oncogenic BRAF can be inhibited, e.g. in one embodiment, the oncogenic BRAF that is inhibited is BRAF (V600E). Alternative oncogenic BRAFs are described within the specification. The inhibitor may be specific for a particular oncogenic BRAF mutation or alternatively may generally inhibit multiple BRAF mutations, and/or wild type BRAF.

Any inhibitor of dihydroorotate dehydrogenase (DHODH) may be used. In one embodiment, the inhibitor of dihydroorotate dehydrogenase (DHODH) to be used in combination with an inhibitor of oncogenic BRAF is selected from the group consisting of: leflunomide, teriflunomide, brequinar, dichloroallyl lawsone, maritimus, redoxal and NSC210627, or a derivative thereof. In one embodiment, the DHODH inhibitor is selected from the group consisting of $C_{19}H_{14}F_2N_2O_3$, compound 1; $C_{20}H_{16}F_2N_2O_3$, compound 2; $C_{18}H_{13}F_6NO_4$, compound 3; $C_{19}H_{16}F_3NO_4$, compound 4; $C_{19}H_{10}F_5NO_4S$, compound 5; $C_{19}H_{14}FNO_4S$, compound 6; $C_{20}H_{15}F_4NO_4$, compound 7; $C_{19}H_{17}NO_4$, compound 8; $C_{20}H_{17}F_2NO_4$, compound 9; and $C_{20}H_{18}FNO_4$, compound 10, each as depicted in FIG. 21, FIG. 22 and FIG. 23.

In one embodiment, the inhibitor of oncogenic BRAF is selected from the group consisting of: Sorafenib, RAF265, XL281, AZ628, GSK2118436, GDC-0879, PLX4032, and PLX4720, or a derivative thereof.

In one embodiment, the inhibitor of oncogenic BRAF is PLX4032 and the inhibitor of dihydroorotate dehydrogenase (DHODH) is leflunomide, or a derivative thereof.

In another embodiment, the inhibitor of oncogenic BRAF is PLX4720 and the inhibitor of dihydroorotate dehydrogenase (DHODH) is leflunomide, or a derivative thereof.

In another embodiment, the methods of treatment described herein, further comprise selecting a subject that has, or is at risk of having melanoma, e.g. a melanoma that expresses oncogenic BRAF. In one embodiment, the subject has a melanoma that expresses an oncogenic BRAF comprising a mutation in BRAF selected from the group consisting of: VAL600GLU, ARG461ILE, ILE462SER, GLY463GLU, and LYS600GLU, GLY465VAL and LEU596ARG, and GLY468ARG, GLY468ALA and ASP593GLY.

The methods of the present invention can be used either alone, or in conjunction with other treatment methods known to those of skill in the art. For example, such methods may include, but are not limited to, chemotherapy, radiation therapy, or surgery.

Administration of the inhibitors can be performed by intravenous, intramuscular, subcutaneous, intradermal, topical, intraperitoneal, intrathecal, intrapleural, intrauterine, rectal, vaginal, intrasynovial, intraocular/periocular, intratumor or parenteral administration.

In one embodiment, the subject is at risk for developing melanoma and the combination therapy, or DHODH inhibitor, is administered prophylactically. The risk can be determined genetically. Alternatively, the risk can be determined by measuring levels of marker proteins in the biological fluids (i.e. blood, urine) of a patient. In one embodiment, the methods of treatment described herein further comprises the step of selecting a subject in need thereof of treatment, e.g. selecting a subject diagnosed with melanoma, or a subject at increased risk of melanoma (e.g. potential cancer relapse).

In another aspect of the invention, screening methods for identifying agents that inhibit melanoma growth are provided. The methods comprise, (a) contacting a zebrafish embryo with a test agent for a period of time, (b) rinsing the test agent from the embryos of step (a); and (c) assaying the number of neural crest progenitors as compared to a control zebrafish embryo that has not been contacted with the test agent, wherein a reduced number of neural crest progenitors (e.g. and their differentiation into melanocytes) indicates that the compound is capable of inhibiting melanoma. The zebrafish embryos may be wild type zebra fish embryos or transgenic zebrafish embryos.

In one embodiment, the number of neural crest progenitors is assayed by monitoring crestin expression, or sox10 expression, or dct expression, e.g. by quantitation of ISH studies.

In one embodiment, the transgenic zebrafish embryo expresses green fluorescent protein operably linked to the melanocyte mitfa promoter and melanocyte neural crest progenitors are monitored by GFP expression.

BRIEF DESCRIPTION OF FIGURES

FIG. 1a, Transgenic zebrafish expressing BRAF$^{V600E}$ under the melanocyte specific mitfa promoter develop pigmentation abnormalities, and melanoma when crossed with p53$^{-/-}$ fish. Gross embryonic development is largely normal. FIG. 1b, Gene expression analysis reveals a unique gene signature at 72 hpf in the BRAF$^{V600E}$;p53$^{-/-}$ strain (left). Gene set enrichment analysis (GSEA) reveals an enrichment between the embryonic gene signature and the adult melanomas which form 4-12 months later (middle and right; see Methods for full GSEA methods). Embryo heat map columns represent average of 3 clutches ($\log_2$ scale, range −2 to +2 fold); adult heat map columns represent individual fish ($\log_2$ scale, range −10 to +10 fold). FIG. 1c, Sagittal section of WT and BRAF$^{V600E}$;p53$^{-/-}$ adults reveal homogeneous crestin expression (blue staining, shown as dark grey) only within the dorsal melanoma, whereas it is absent in normal adult tissues.

FIG. 2a, A chemical genetic screen to identify suppressors of the crestin$^+$ lineage during embryogenesis identified NSC210627, a compound which completely abrogates expression by ISH (FIG. 2a, top and middle). The Discovery gate chemoinformatic algorithm revealed structural similarity between NSC210627 and brequinar (see FIG. 5), an inhibitor of dihydroorotate dehydrogenase (DHODH). Leflunomide, FIG. 2a structurally distinct DHODH inhibitor, phenocopies the crestin phenotype of NSC210627 (FIG. 2a, right). FIG. 2a bottom panel; Leflunomide caused an absence of multiple neural crest derivatives, including pigmented melanocytes, mitf-GFP$^+$ melanocyte progenitors, and mbp-mCherry$^+$ glial cells. FIG. 2b, Leflunomide or A771726 (see FIG. 6a) significantly reduced the number of multipotent daughter cells that could be subcloned from individual primary neural crest stem cell colonies (Values shown are mean+/−SD of n=3 replicates; *, p<0.05 compared to control, t-test).

FIG. 3a, The hypomorphic spt5$^{m806}$ mutant has only a mild pigment defect on its own (top). Treatment with low-dose leflunomide (3 uM) leads to an almost complete absence of neural crest derived melanocytes in the mutant line. See FIG. 7 for dose-response quantification of this effect. FIG. 3b, Metagene analysis of RNA pol II occupancy in A375 human melanoma cells after treatment with leflunomide. Pol II occupancy at the promoter region is unaffected, but diminished at the 3' end of the genes. Inset shows a higher magnification of the 3' region of the genes. FIG. 3c, Representative examples of myc target genes which demonstrate defects in transcriptional elongation after leflunomide treatment, along with a non-affected gene. For Npm1, the TR in DMSO=5.04, and in LEF=8.10. For Ccnd1, the TR in DMSO=3.47, and in LEF=4.67.

FIG. 4a, Leflunomide causes a dose-dependent decrease in melanoma proliferation as measured by CellTiterGlo assay in 3 BRAF$^{V600E}$ melanoma cells lines tested (A375, RPMI7951, Hs.294T). FIG. 4b, FIG. 4c Leflunomide cooperates with the BRAF$^{V600E}$ inhibitor PLX4720 in inhibiting melanoma cell proliferation in the A375 (FIG. 4b) and Hs.294T (FIG. 4) cell lines as well as the other tested lines (See FIG. 8).

FIG. 6a, The effects of A771726 on rat neural crest stem cell self-renewal (as described in FIG. 2, *, p<0.05, compared to control, t-test). FIG. 6b, FIG. 6c, Both compounds cause no defect in plating efficiency or affect individual progeny (NGM=nerve, glia, smooth muscle) without (N, G, or M colonies) survival or differentiation capacity (p>0.05, n=3, ANOVA). Values shown are mean+/−SD of n=3 replicates.

FIG. 7a, Pigmentation scores in untreated embryonic offspring of an incross of the spt5$^{m806}$ hypomorphic mutant. There is a mild pigmentation defect only in homozygous embryos. FIG. 7b, FIG. 7c, FIG. 7d Leflunomide at 3, 4 or 5 uM demonstrates that both heterozygous and homozygous mutants embryos show increased sensitivity to pigment loss when compared to wild-type (*, p=0.000018, Kruskal-Wallis, n values as indicated in Figure).

FIG. 8a, FIG. 8ab, In vitro proliferation assay testing the effects of combined A771726 and the BRAF inhibitor PLX4720 on RPMI7951 and 294T cells shows significant augmentation of the effects of the BRAF inhibitor alone. FIG. 8c, PLX4720 is only effective in BRAF$^{V600E}$ melanoma cells. Although RPMI7951 is BRAF$^{V600E}$, it is significantly less sensitive than the other tested cell lines. FIG. 8d, Proliferation in the presence of A771726 in pancreatic cancer (8988, PANC1) and breast cancer (MDA-MD-231) cell lines. Values shown are mean+/−SEM of n=4 replicates.

FIG. 9b, shows marker staining of tumors, a representative tumor in which all 4 markers are expressed in different areas of the tumor.

FIG. 13a, The spt5sk8−/− transcriptional elongation mutant phenocopies the absence of crestin+ progenitors in a manner analogous to leflunomide. FIG. 13b, GSEA was used to compare the gene expression signature of leflunomide treated embryos and spt5sk8−/− embryos at 24 hpf. Venn diagram shows the number of genes up or downregulated in the spt5sk8−/− mutant that are similarly up or downregulated after leflunomide treatment. (see Methods for full GSEA analysis methods) FIG. 13c, qRT-PCR on whole embryos treated with DMSO or leflunomide was used to measure transcription elongation at the 5' or 3' end of the noted gene. Leflunomide treatment caused a significant decrease in 3' transcription of mitf, pvalb2, her4.2 and dlb, whereas control genes showed no bias towards 5' or 3' effects (n=6 replicates in each group, *p<0.05, two-sided t-test, leflunomide vs. DMSO). Values shown are mean+/−SEM.\

FIG. 14a, Metagene analysis of RNA polymerase II occupancy of the promoter and gene body in MAMLE-3M cells treated with DMSO (control) or leflunomide 50 uM. Leflunomide causes no defect in promoter occupancy but significantly decreases pol II occupancy in the body of the gene, consistent with an inhibition of transcriptional elongation. FIG. 14b, Representative examples of affected (left) and unaffected genes in this cell line.

FIG. 15a, Western blot showing extent of DHODH knockdown induced by shRNA#877 as compared to scrambled (scr) control shRNA in A375 melanoma cells. FIG. 15b, Cell counts measured over an 8 day period in A375-scr and A375-shRNA#877 cells shows a 57% decrease in cellular proliferation with DHODH knockdown. FIG. 15c, ChIP-PCR in A375-scr and A375-shRNA#877 cells demonstrates decreased RNA pol II binding at the 3' end of myc, npml and otub, consistent with an inhibition of transcriptional elongation (*p<0.05, +p=0.1 t-test, A375-sh877 vs. A375-scr cells, n=3-4). Values shown are mean+/−SEM.

FIG. 22 shows the chemical structures of DHODH inhibitors: Compound 5 and Compound 6, which are used in Example III. Synthesis of compound 5 and compound 6 is described in U.S. Patent Publication 2004/0192758.

FIG. 24a shows the chemical structures for leflunomide, which gets converted into its active form A771726 also shown, which causes dihydroorotate dehydrogenase inhibition. Also shown in FIG. 24a is a structurally different DHODH inhibitor, inhibitor DH#1, also known as Compound 1 herein, as used in Example III. FIG. 24b are ISH staining showing the effect of DHODH inhibitor compound 1 (DH#1); leflunomide; and A771726 on neural crest development, in the presence of DMSO, Decylubiquinone, Aphidicolin, or Progesterone. FIG. 24b shows that all of these inhibitors (leflunomide, A77 1726, or DH #1) lead to reduction in expression of the neural crest, depicted by an in situ hybridization for the neural crest marker crestin. However, chemicals including decylubiquinone, aphidicolin, and progesterone suppress these drugs and lead to a rescue of the neural crest population.

FIG. 27 shows a graph depicting the effect of all of the DHODH inhibitors compounds 1-10 (DHODH analogs) (See FIGS. 21-23 for compounds) on A375 cells after 3 days of treatment. y-axis percent inhibition, x-axis concentration. Compounds 1, 4, and 7 significantly decrease cell proliferation at lower doses compared to leflunomide and A771726.

FIGS. 28a to 28e show graphs depicting the effects of leflunomide, Compound 1 (PH-1), and Compound 7 (PH-7) (See FIG. 21 (compound 1) and FIG. 23 (compound 7)) on the indicated melanoma cells in vitro. FIG. 28a, M481 cells. FIG. 28b, A375 cells. FIG. 28c, M405 cells. FIG. 28d, M528 cells. FIG. 28e, M715 cells. Compound 1, Compound 7 and leflunomide affect cell viability of human primary melanoma cells. FIGS. 28a and 28b show respectively that leflunomide as well as DHODH #1 (PH-01, i.e. compound 1), DHODH#7 (PH-07, i.e. compound 7) impair cell survival in primary human melanoma cells (M481) and in the melanoma cell line (A375). FIG. 28c shows that the effect of these inhibitors is variable in different primary melanoma cells (M405, M528 and M715).

FIGS. 29a to 29d are graphs showing the in vivo effects of leflunomide in combination with digitoxin on M405 tumor xenografts in mouse. FIG. 29a, effect on tumor diameter (cm) vs. time. FIG. 29b, effect on tumor weight. FIG. 29c, effect on frequency of melanoma cells in the blood. FIG. 29d, Total flux (photons/second). M405 were not sensitive to drug treatment as shown in FIG. 28 and accordingly there is no effect on tumor growth (FIG. 29a) and number of melanoma cells in blood circulating cells (FIG. 29b). But there is significant difference in blood circulating cells in co-treatment with Leflunomide and Digitoxin. No change in flux was observed (FIG. 29d).

FIG. 30 shows the effect of leflunomide in combination with Plexicon in xenografts mouse model. M841 primary human melanoma xenografts in mice revealed that leflunomide is more effective when used in combination with Plexicon.

DETAILED DESCRIPTION

Figure 1A:
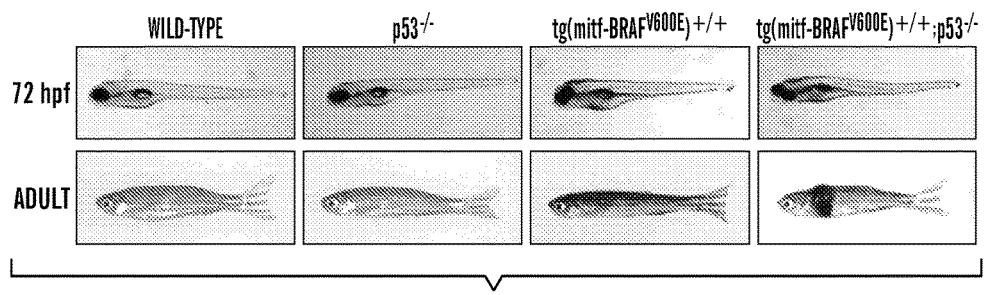
FIGS. 1a to 1c show zebrafish melanoma and neural crest gene expression.

The present invention relates generally to a method of treating melanoma in a subject having, or at risk of having, melanoma.

As used herein, the term "subject" or "patient" or refers to any mammal. The patient is preferably a human, but can also be a mammal in need of veterinary treatment.

The term "melanoma" as used herein includes all types of melanoma, including, for example, melanoma skin cancer, ocular melanoma, and mucosal melanoma. Melanoma is caused by changes melanocytes that produce melanin. There are four major types of melanoma: 1) superficial spreading melanoma, which is usually flat and irregular in shape and color, with different shades of black and brown and is most common in Caucasians, 2) nodular melanoma, which usually starts as a raised area that is dark blackish-blue or bluish-red, but can be colorless, 3) Lentigo maligna melanoma, which usually occurs in the elderly and is most common in sun-damaged skin on the face, neck, and arms. The abnormal skin areas are usually large, flat, and tan with areas of brown, 4) Acral lentiginous melanoma, which is the least common form and usually occurs on the palms, soles, or under the nails and is more common in African Americans. Melanomas may also appear in the mouth, iris of the eye, or retina at the back of the eye and can be found during dental or eye examinations. Although very rare, melanoma can also develop in the vagina, esophagus, anus, urinary tract, and small intestine.

The presence of melanoma can be determined by means well known to those of skill in the art, e.g. tissue biopsies and in situ assays in which malignant melanoma (malignant melanocytes scattered in all epidermal layers) show atrophic epidermis, prominent dermal solar elastosis and almost always lymphocytic infiltration. Invasion of the dermis by melanocytes may occur in lentigo maligna melanoma. In addition, melanoma may be detected by methods that include, but are not limited, immunohistochemistry using the melanoma specific antibody HMB-45, or RT-PCR with different melanoma associated antigens (MAA) including, but not limited to tyrosinase, MART-1/Melan A, Pmel-17, TRP-1, and TRP-2 (see, e.g., Hatta N., et al., *J Clin Pathol.* 1998 August; 51(8):597-601). Biomarkers for melanoma are also known and can be used for example to assess subjects at risk of melanoma. Non-limiting example biomarkers for melanoma are described in PCT Publications WO 2008/141275, WO 2009/073513, or in U.S. Pat. No. 7,442,507, which are herein incorporated by reference in their entirety.

Symptoms of melanoma include, but are not limited to, a mole, sore, lump, or growth on the skin that may bleed, or exhibit change in skin coloring. Often patients are told of an ABCDE system the can help them remember possible symptoms of melanoma to watch out for: Asymmetry: a mole where one half of the abnormal area is different from the other half; Borders, the edges of the growth are irregular; Color, the color changes from one area to another, with shades of tan, brown, or black, and sometimes white, red, or blue, e.g. a mixture of colors may appear within one sore; Diameter, the spot is usually (but not always) larger than 6 mm in diameter, about the size of a pencil eraser; and Evolution, the mole keeps changing appearance.

As used herein, "treatment", "treating", "prevention" or "amelioration" of melanoma refers to inhibition of growth of a melanoma, inhibiting metastasis of melanoma, delaying or preventing the onset of melanoma, or reversing, alleviating, ameliorating, inhibiting, slowing down, or stopping the progression of melanoma. The term "treatment" as used herein is not intended encompass 100% cure of melanoma. However, in one embodiment, the therapeutic methods described herein may result in 100% reversal of disease.

In one embodiment of the methods described herein, at least one symptom of melanoma is alleviated by at least 5%, at least 10%, at least 20%, at least 30%, at least 40%, at least 50%, at least 60%, at least 70%, at least 80%, or at least 90%. In such an embodiment, the clinical signs and/or the symptoms associated with the melanoma are lessened as a result of the administration of the inhibitor/s. The signs or symptoms to be monitored are characteristic of a particular melanoma and are known to the skilled clinician, as well as the methods for monitoring the signs and conditions.

In one embodiment of the methods described herein, the melanoma lesion size is reduced by at least 5%, at least 10%, at least 20%, at least 30%, at least 40%, at least 50%, at least 60%, at least 70%, at least 80%, or at least 90%.

In one embodiment of the methods describe herein, melanoma cell proliferation, or melanoma growth, is inhibited by at least 5%, at least 10%, at least 20%, at least 30%, at least 40%, at least 50%, at least 60%, at least 70%, at least 80%, or at least 90%. The skilled clinician may monitor the size or rate of growth of a tumor using a diagnostic imaging method typically used for the particular tumor (e.g., using ultrasound or magnetic resonance image (MRI) to monitor a tumor).

In one embodiment, the method for treatment of melanoma comprises administering to a subject in need thereof a therapeutically effective amount of an inhibitor of DHODH.

As used herein the term "dihydroorotate dehydrogenase (DHODH)" refers to the enzyme that catalyzes the fourth step in the de novo biosynthesis of pyrimidine. DHODH converts dihydroorotate to orotate. The sequences of DHODH are well known to those of skill in the art, e.g. a human DHODH protein sequence is found at GenBank accession no. AAA50163.1 (SEQ ID NO:2), gene (SEQ ID NO:4). Enzymatic activity of DHODH can be assessed using in vitro assays and monitoring the reduction in 2,6-dichloroindophenol (DCIP) (e.g. see Examples).

Any inhibitor of DHODH can be used in methods of the invention. As used herein, the phrase "inhibitor of DHODH" means a compound or agent that inhibits the biological activity of DHODH. The biological activity of DHODH can be inhibited using a compound or agent that inhibits the enzymatic activity of DHODH, or a compound or agent that down regulates expression or availability of DHODH in a cell or organism (e.g. siRNA, shRNA). Many inhibitors of DHODH are known to those skilled in the art. For example, various inhibitors are described in: Leban et al. (2005) SAR, species specificity, and cellular activity of cyclopentene dicarboxylic acid amides as DHODH inhibitors, *Bioorganic & Medicinal Chemistry Letters* 15(21): 4854-4857; and Fritzson et al. (2010) Inhibition of human DHODH by 4-Hydroxycoumarins, fenamic acids, and N-(alkylcarbonyl) anthranilic acids identified by structure-guided fragment selection *Chem Med Chem* 5(4): 608-617; Kulkarni et al. (2010) 4SC-101 a novel small molecule dihydroorotate dehydrogenase inhibitor, suppresses systemic lupus erythematosus in MRL-(Fas)lpr mice *Am J Pathol.* 176(6):2840-7;

Various DHODH inhibitors have been disclosed for the treatment or prevention of autoimmune diseases, immune and inflammatory diseases, destructive bone disorders, malignant neoplastic diseases, angiogenic-related disorders, viral diseases, and infectious diseases. See for example WO2010083975; WO2011138665; WO200137081; WO2009133379; WO 2009021696; WO200 082691; WO2009029473; WO2009153043; US2009209557; US2009 062318; US2009082374; WO2008097180; W02QQ8Q77639; US2008027079; US2007 299U4; US2007027193; US2007224672; WO2007149211; JP2007015952; WO2006 044741; WO2006001961; WO2006051937; WO2006038606; WO2006022442; US2006 199856; WO2005075410; U.S. Pat. No. 7,074,831; WO2004056797; U.S. Pat. No. 7,247,736; WO2004056747; WO 2004056746; JP2004099586; WO2003097574; WO2003030905; WO2003006425; WO2003 006424; US2003203951; WO2002080897; U.S. Pat. No. 7,176,241; U.S. Pat. No. 7,423,057; WO2001024785; U.S. Pat. No. 6,841,561; WO9945926; WO9938846; WO9941239; EP767167 and U.S. Pat. No. 5,976,848, each of which are herein incorporated by reference in their entirety. For additional reviews and literature regarding DHODH inhibitors see *Bio & Med. Chem. Letters,* 20(6), 2010, pages 1981-1984; *Med. Chem.* 2009, 52, 2683-2693; *J. Med. Chem.* 2008, 51 (12), 3649-3653.

Figure 5:
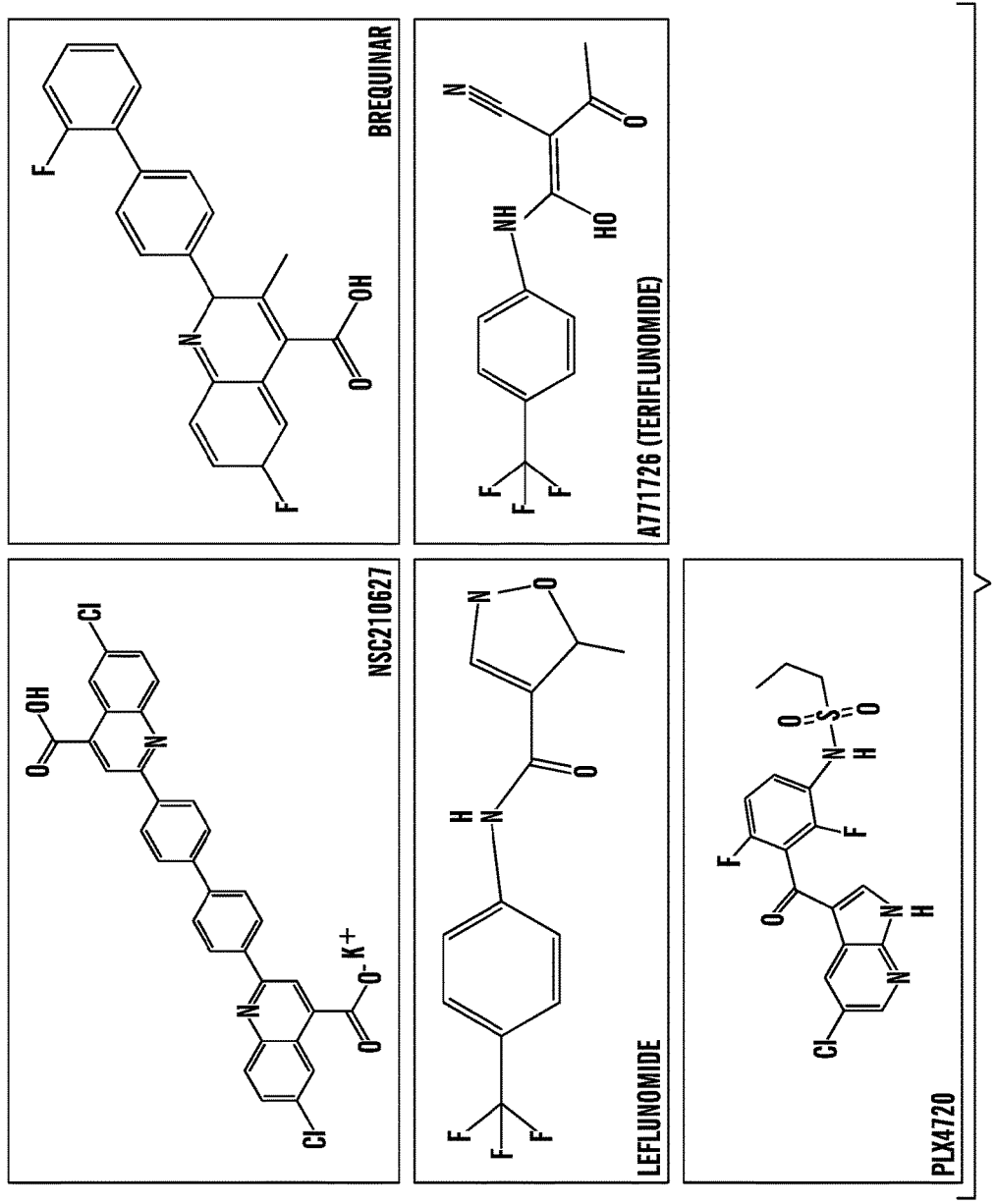
FIG. 5 shows chemical structures of DHODH inhibitors NSC210627, brequinar, leflunomide and A771726 (teriflunomide) and oncogenic BRAF inhibitor PXL4720.

For example, inhibitors include, but are not limited to, leflunomide, teriflunomide, brequinar (NSC 368390) (*Cancer Research* 1992, 52, 3521-3527), Dichloroallyl lawsone (*The Journal of Biological Chemistry* 1986, 261(32), 14891-14895; McKelvey et al. *Clin Pharmacol Ther.* 1979 May; 25(5 Pt 1):586-90.), Maritimus (F 778) (*Drugs of the Future* 2002, 27(8), 733-739) and Redoxal (*The Journal of Biological Chemistry* 2002, 277(44), 41827-41834). See also Example 1 and FIG. 5, which describes a compound of previously unknown function, NSC210627, with similarity to brequinar, a known inhibitor of DHODH.

Figure 21:
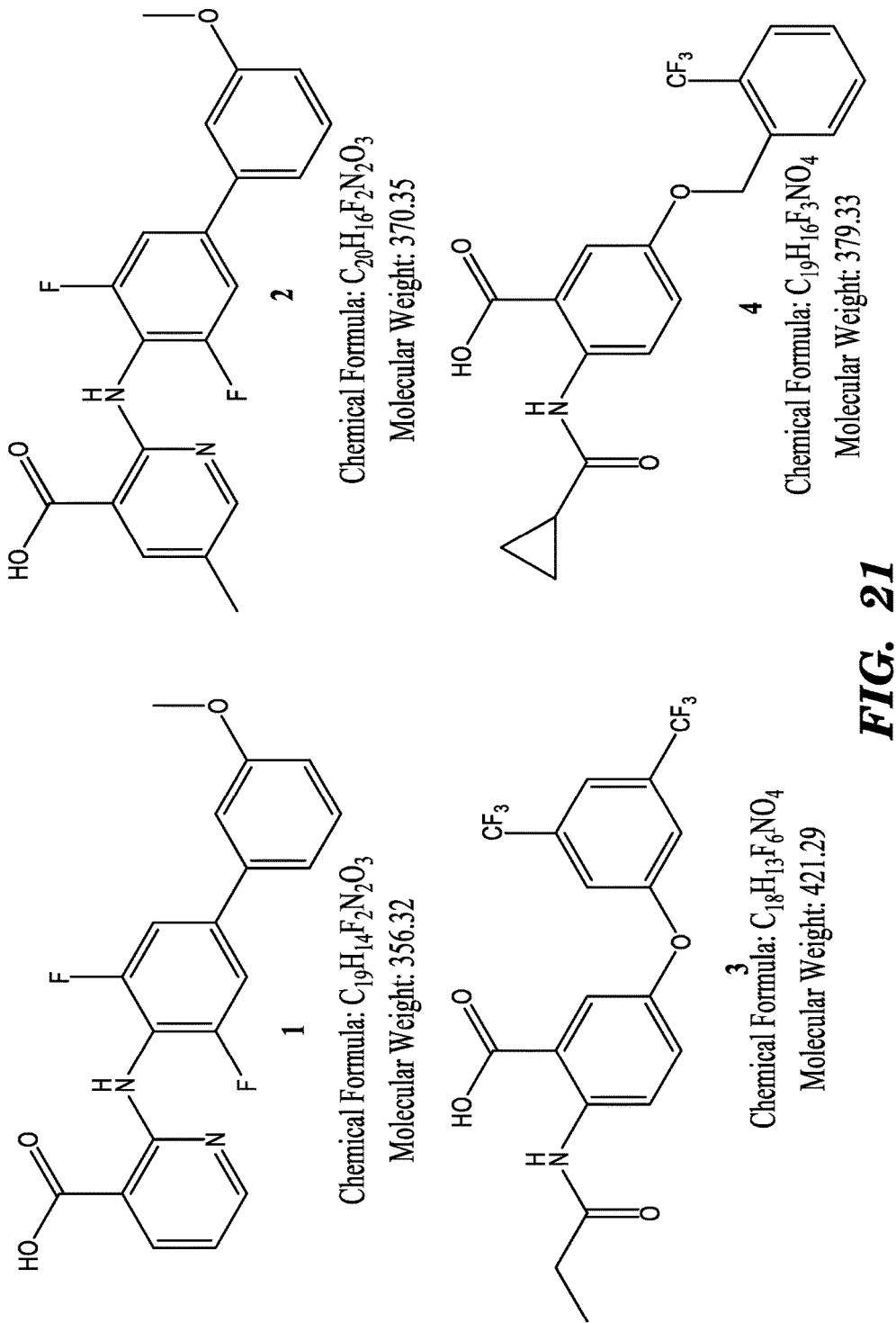
FIG. 21 shows the chemical structures of DHODH inhibitors Compound 1, Compound 2, Compound 3, and Compound 4, which are used in Example III. Synthesis of compound 1 and compound 2 is described in U.S. Patent Publication 2010/007898. Synthesis of compounds 3 and 4 is described in U.S. Pat. No. 7,074,831.
Figure 23:
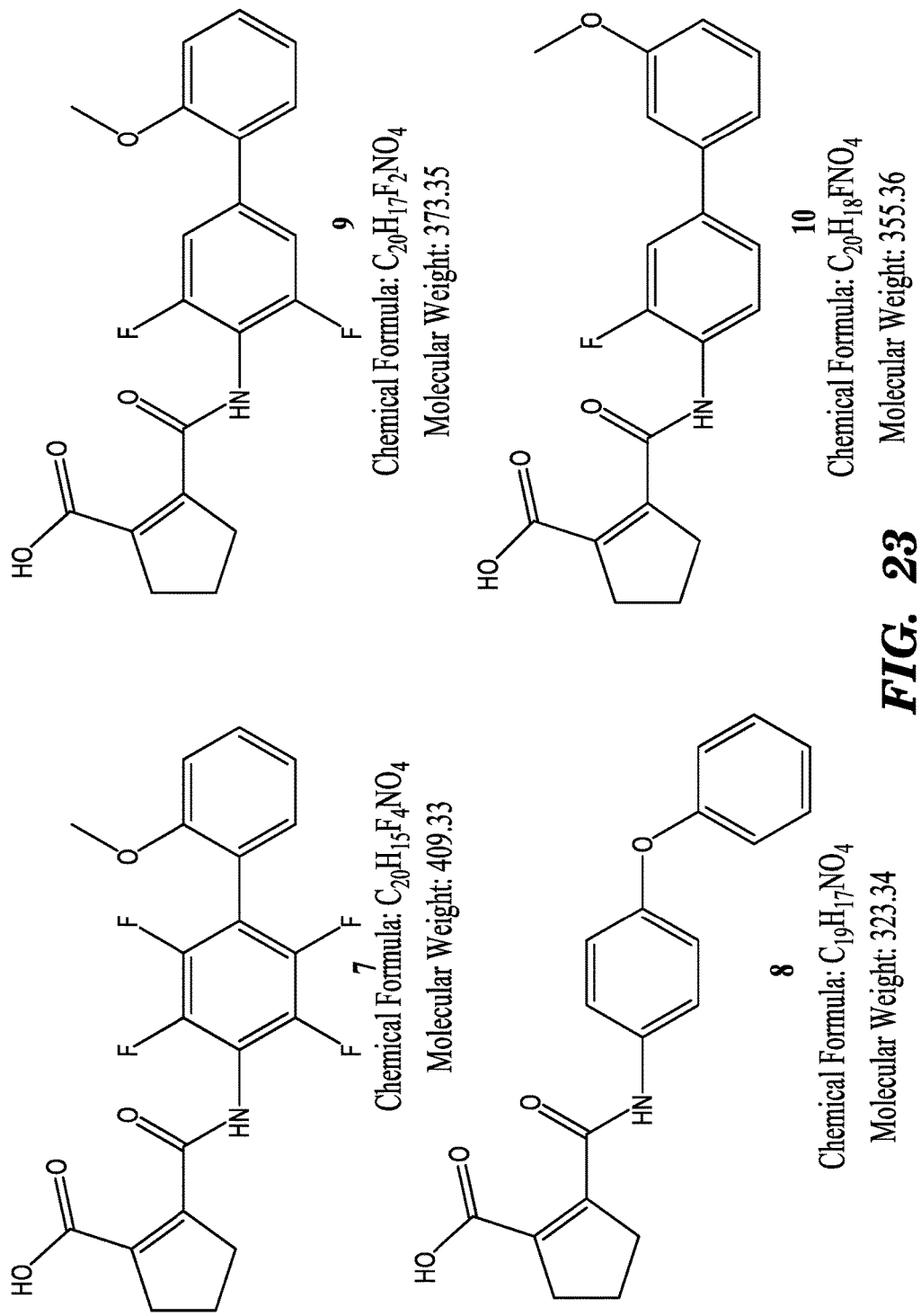
FIG. 23 shows the chemical structures of DHODH inhibitors: Compound 7, Compound 8, Compound 9, and Compound 10, which are used in Example III. Synthesis of these compounds is described in U.S. Patent Publication 2006/0199859 and in U.S. Pat. No. 7,176,241.

In one embodiment, the DHODH inhibitor is selected from the group consisting of $C_{19}H_{14}F_2N_2O_3$, compound 1; $C_{20}H_{16}F_2N_2O_3$, compound 2; $C_{18}H_{13}F_6NO_4$, compound 3; $C_{19}H_{16}F_3NO_4$, compound 4; $C_{19}H_{10}F_5NO_4S$, compound 5; $C_{19}H_{14}FNO_4S$, compound 6; $C_{20}H_{15}F_4NO_4$, compound 7; $C_{19}H_{17}NO_4$, compound 8; $C_{20}H_{17}F_2NO_4$, compound 9; and $C_{20}H_{18}FNO_4$, compound 10, each as depicted in FIG. 21, FIG. 22 and FIG. 23. Compound 1, Compound 2, Compound 3, and Compound 4, which are used in Example III. Synthesis of compound 1 and compound 2 is described in U.S. Patent Publication 2010/007898, which is herein incorporated by reference in its entirety. Synthesis of compounds 3 and 4 is described in U.S. Pat. No. 7,074,831, which is herein incorporated by reference in its entirety. FIG. 22 shows the chemical structures of DHODH inhibitors: Compound 5 and Compound 6, which are used in Example III. Synthesis of compound 5 and compound 6 is described in U.S. Patent Publication 2004/0192758, which is herein incorporated by reference in its entirety. FIG. 23 shows the chemical structures of DHODH inhibitors: Compound 7, Compound 8, Compound 9 and Compound 10, which are used in Example III. Synthesis of these compounds is described in U.S. Patent Publication 2006/0199859 and in U.S. Pat. No. 7,176,241, which are herein incorporated by reference in their entirety.

Leflunomide is sold under the trade name Arava (EP 0 780 128, WO 97/34600), and was the first DHODH inhibitor that reached the market place. Leflunomide is the prodrug of teriflunomide (A771726), which is the active metabolite that inhibits human DHODH with a moderate potency. In one specific embodiment, the inhibitor of DHODH is not leflonomide or its derivative A771726. In one embodiment, the inhibitor of DHODH is not maritumis.

In one embodiment, the inhibitor of DHODH is not $C_{19}H_{14}F_2N_2O_3$, compound 1 (FIG. 21). In one embodiment, the inhibitor of DHODH is not $C_{20}H_{16}F_2N_2O_3$, compound 2 (FIG. 21). In one embodiment, the inhibitor of DHODH is not $C_{18}H_{13}F_6NO_4$, compound 3 (FIG. 21). In one embodiment, the inhibitor of DHODH is not $C_{19}H_{16}F_3NO_4$, compound 4 (FIG. 21). In one embodiment, the inhibitor of DHODH is not $C_{19}H_{10}F_5NO_4S$, compound 5 (FIG. 22). $C_{19}H_{14}FNO_4S$, compound 6 (FIG. 22). In one embodiment, the inhibitor of DHODH is not $C_{20}H_{15}F_4NO_4$, compound 7 (FIG. 23). In one embodiment, the inhibitor of DHODH is not $C_{19}H_{17}NO_4$, compound 8 (FIG. 23). In one embodiment, the inhibitor of DHODH is not $C_{20}H_{17}F_2NO_4$, compound 9 (FIG. 23). In one embodiment, the inhibitor of DHODH is not $C_{20}H_{18}FNO_4$, compound 10 (FIG. 23).

Additional compounds or agents that inhibit DHODH expression or activity may be readily identified using known screening methods. In one embodiment, the compounds identified binds specifically to the DHODH polypeptide and inhibit its enzymatic activity. The ability of a compound to inhibit DHODH can be determined using enzymatic assays well known to those of skill in the art. Target validation models are known to those of skill in the art, e.g. Zameitat et al. (2007) Functional Expression of Human Dihydroorotate Dehydrogenase (DHODH) in pyr4 Mutants of Ustilago maydis Allows Target Validation of DHODH Inhibitors In Vivo *Appl. Environ. Microbiol.* 73(10) 3371-3379.

The term "agent" or "compound" as used herein and throughout the specification means any organic or inorganic molecule, including modified and unmodified nucleic acids such as antisense nucleic acids, RNAi, such as siRNA or shRNA, peptides, small molecules peptidomimetics, receptors, ligands, and antibodies. e.g. molecules and/or compositions that inhibit DHODH activity or inhibit BRAF activity. The compounds/agents include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies, or fragments thereof.

A compound/agent can be a nucleic acid RNA or DNA, and can be either single or double stranded. Example nucleic acid compounds include, but are not limited to, a nucleic acid encoding a protein inhibitor (e.g. transcriptional inhibitors), oligonucleotides, nucleic acid analogues (e.g. peptidenucleic acid (PNA), pseudo-complementary PNA (pc-PNA), locked nucleic acid (LNA) etc.), antisense molecules, ribozymes, small inhibitory or activating nucleic acid sequences (e.g. RNAi, shRNAi, siRNA, micro RNAi (mRNAi), antisense oligonucleotides etc.) A protein and/or peptide agent can be any protein that modulates gene expression or protein activity. Non-limiting examples include mutated proteins; therapeutic proteins and truncated proteins, e.g. wherein the protein is normally absent or expressed at lower levels in the target cell. Proteins can also be selected from genetically engineered proteins, peptides, synthetic peptides, recombinant proteins, chimeric proteins, antibodies, midibodies, minibodies, triabodies, diabodies, humanized proteins, humanized antibodies, chimeric antibodies, modified proteins and fragments thereof. A compound or agent that increases expression of a gene or increases the activity of a protein encoded by a gene is known as an activator or activating compound. A compound or agent that decreases expression of a gene or decreases the activity of a protein encoded by a gene is also known as an inhibitor or inhibiting compound.

The terms "polypeptide," "peptide" and "protein" refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acids.

In some embodiments, the methods of the invention are directed to a combination therapy wherein one component is administration of an effective amount of an inhibitor of BRAF oncogene (e.g. BRAF(V006E)), and a second component is administration of an effective amount of an inhibitor of DHODH.

As used herein the term "BRAF" refers to the serine/threonine kinase BRAF polypeptide as well as the gene encoding it. BRAF is known to transduce regulatory signals from RAS through MEK (MAPK kinase) to ERK. Sequences for BRAF genes and proteins are well known to those of skill in the art, e.g. the protein sequence for human wild type BRAF is found at GenBank accession no. NP_004324.2 (SEQ ID NO: 1). BRAF oncogenic mutations lead to constitutive activation of the RAS-RAF-mitogen activated protein kinase/ERK kinase (MEK)-extracellular signal regulated kinase (ERK) signaling pathway, which is essential for cell proliferation, differentiation and survival (Davies et al., *Nature* 417:949-54 (2002)); English et al., *Trends Pharmacol. Sci.* 23:40-5 (2002)). A complete cDNA for human BRAF is disclosed in Sithanandam, G., et al. complete coding sequence of a human B-raf cDNA and detection of B-raf protein kinase with isozyme specific antibodies *Oncogene* 5 (12), 1775-1780 (1990), see also GenBank accession No: NM_004333.4, (SEQ ID NO: 5).

As used herein, "oncogenic BRAF" refers to a BRAF gene/polypeptide that is aberrantly expressed or aberrantly active. This increase in expression or activity can result from a mutation(s) in BRAF, which constitutively activates the MEK/ERK or other pathways, or from a defect resulting in a detectable increase in BRAF expression or activity in cancer cell compared to a non-cancerous. In addition to mutations, such increased expression and/or activity may result from amplification of a wild-type BRAF nucleic acid, overexpression of a wild-type BRAF protein, e.g., by aberrant regulation of the BRAF regulatory region such as the promoter, overexpression or activation of BRAF due to aberrant regulation of an upstream regulator (e.g., RAS mutation, or inhibition of a BRAF inhibitor) or by stabilization of BRAF.

Oncogenic BRAF mutations have been identified in about 70% of malignant melanomas (Davies et al., *Nature* 417: 949-54 (2002)) and are implicated in the malignant growth of melanoma cells (Wellbrock et al., *Cancer Res.* 64:2338-42 (2004); Hingorani et al., *Cancer Res.* 63:5198-202 (2003)). The term "mutation" includes substitution, deletions, inversions, insertions, premature terminations and the like. A T1796A transversion in exon 15, which results in a V600E (also known as V599E) substitution in the BRAF kinase domain, accounts for about 90% of BRAF mutations detected in melanoma samples (Davies et al., supra). The V600E mutation increases BRAF kinase activity (Davies et al., supra; Dong et al., *Cancer Res.* 2003; 63: 3883-3885). Additional mutations of the BRAF gene in human cancer, include but are not limited to, ARG461ILE, ILE462SER, GLY463GLU, and LYS600GLU (Rajagopalan, H., et al. (Letter) *Nature* 418: 934, 2002), GLY465VAL and LEU596ARG (Naoki, K., et al., *Cancer Res.* 62: 7001-7003, 2002), and GLY468ARG, GLY468ALA and ASP593GLY (Lee, J. W., et al., *Brit. J Cancer* 89: 1958-1960, 2003), the references of which are each incorporated by reference in their entirety.

In one embodiment, the oncogenic BRAF to be inhibited in the combination therapy of the invention has a mutation selected from the group consisting of VAL600GLU (also named as VAL599GLU) (Davies et al. *Nature.* Jun. 27, 2002; 417(6892):949-54), ARG461ILE, ILE462SER, GLY463GLU, and LYS600GLU (Rajagopalan, H., et al. (Letter) *Nature* 418: 934, 2002), GLY465VAL and LEU596ARG (Naoki, K., et al., *Cancer Res.* 62: 7001-7003, 2002), and GLY468ARG, GLY468ALA and ASP593GLY (Lee, J. W., et al., *Brit. J Cancer* 89: 1958-1960, 2003), the references of which are each incorporated herein by reference in their entirety. In one embodiment, the inhibitor binds specifically to oncogenic BRAF polypeptide.

Any inhibitor of oncogenic BRAF (e.g. BRAFV600E) can be used in methods of the invention. As used herein, the phrase "inhibitor of oncogenic BRAF" means a compound or agent that inhibits the biological activity of a BRAF oncogene, mutated or aberrantly expressed wild type. Multiple BRAF inhibitors are well known to those of skill in the art. For example, BRAF has been a target of small-molecule therapies to treat cancer (See e.g. Halilovic E, and Solit D B, Therapeutic strategies for inhibiting oncogenic BRAF signaling. *Curr Opin Pharmacol* 2008; 8:419-26; McCubrey J A et al. Targeting the Raf/MEK/ERK pathway with small-molecule inhibitors. *Curr Opin Investig Drugs* 2008, 9:614-30; and Michaloglou et al., Peeper D S. BRAF(E600) in benign and malignant human tumors. *Oncogene* 2008; 27:877-95).

Raf inhibitors, such as BAY 43-9006 (sorafenib), are not selective for BRAF, with activity against multiple kinase targets (Wilhelm S M, et al. (2004) BAY 43-9006 exhibits broad spectrum oral antitumor activity and targets the RAF/MEK/ERK pathway and receptor tyrosine kinases involved in tumor progression and angiogenesis. *Cancer Res;* 64:7099-109). Other small-molecule BRAF inhibitors include RAF265, XL281, AZ628, GSK2118436, and GDC-0879: See ClinicalTrials.gov. A study to evaluate RAF265, an oral drug administered to subjects with locally advanced or metastatic melanoma. ClinicalTrials.gov identifier NCT00304525. Accessed Jan. 21, 2010; Schwartz et al. (2008). A phase I study of XL281, a potent and selective inhibitor of RAF kinases, administrated orally to patients with advanced solid tumors. 20th *Eur J Cancer* 6: 120, Abstract 383; and ClinicalTrials.gov. A phase I study to investigate the safety, pharmacokinetics, and pharmacodynamics of GSK2118436 in subjects with solid tumors. ClinicalTrials.gov identifier NCT00880321. Accessed Jan. 21, 2010; Montagut et al (2008) Elevated CRAF as a potential mechanism of acquired resistance to BRAF inhibition in melanoma *Cancer Res* 68:4853-61; and Hoeflich K P, et al (2009) Antitumor efficacy of the novel RAF inhibitor GDC-0879 is predicted by BRAFV600E mutational status and sustained extracellular signal-regulated kinase/mitogen-activated protein kinase pathway suppression. *Cancer Res;* 69: 3042-51.

BRAF inhibitors that have undergone clinical trials are described in Shepard et al. (2010) B-RAF Inhibitors: An Evolving Role in the Therapy of Malignant Melanoma *Current Oncology Reports* Volume 12, Number 3, which is herein incorporated by reference in its entirety.

RG7204 (formerly PLX4032) is a small-molecule inhibitor that inhibits BRAFV600E with a IC50 of 30 nmol/L (Sala E, et al. (2008) BRAF silencing by short hairpin RNA or chemical blockade by PLX4032 leads to different responses in melanoma and thyroid carcinoma cells. *Mol Cancer Res* 6: 751-9).

In one embodiment, the inhibitor of oncogenic BRAF (V600E) is Vemurafenib (also known as PLX4032, RG7204 or RO5185426, and marketed as Zelboraftm (Hoffman-La Roches (Madisin, Wis.)/Daiichi Sankyo (Parsippany, N.J.)). Vemurafenib is a selective inhibitor of BRAF(V600E), and is described in U.S. Pat. No. 7,863,288, herein incorporated by reference in its entirety.

In one embodiment, the inhibitor is a specific inhibitor of oncogenic BRAF(V600E) that is PLX4720 (Plexxikon Inc., Berkeley, Calif., USA) (Tsai J, Lee J T, Wang W, et al. Discovery of a selective inhibitor of oncogenic B-Raf kinase with potent antimelanoma activity. *Proc Natl Acad Sci* USA 2008; 105:3041-3046), see FIG. 5.

In addition, compounds that inhibit oncogenic BRAF (BRAF or mutated BRAF) expression or activity may be readily identified using screening methods well known to those of skill in the art (e.g. see US 2008/0072337). In one embodiment, compounds identified by the screening methods bind specifically to a BRAF nucleic acid or to BRAF polypeptide. In one embodiment, the compounds or agents antagonize BRAF and inhibit a downstream biological effect (e.g., inhibit the phosphorylation of MEK and ERK) that is associated with constitutive BRAF activity. In vivo or cell culture assays may be used to determine whether a test compound functions as an antagonist to inhibit BRAF in cells. For instance, cell culture assays may be used to measure a test compound's ability to modulate an activity, such as detecting inhibition of endogenous phospho-MEK levels, or increase sensitivity to chemotherapy, in tumor cells treated with a test compound. Such assays generally comprise contacting a cell that expresses BRAF or mutated BRAF with a test compound and comparing it to control cells not contacted with the test compound. Cell assays include those utilizing conventional, reporter gene-based assays, among others.

In one embodiment, the inhibitor of oncogenic BRAF is selected from the group consisting of Sorafenib (Bayer), RAF265 (Novartis), XL281 (BMS-908662, Bristol-Myers Squibb; Exelixis), AZ628 (Montagut et al (2008) *Cancer Res* 68:4853-61), GSK2118436 (GlaxoSmithKline,), GDC-0879 (Selleck Chemicals LLC, Houston, Tex.), PLX4032 (Vemurafenib, Plexxikon, Berkeley, Calif., USA), and PLX4720 (Difluorophenyl-sulfonamine, Plexxikon Inc., Berkeley, Calif., USA); and the inhibitor of DHODH is selected from the group consisting of: leflunomide, teriflunomide, brequinar, dichloroallyl lawsone, maritimus, redoxal and NSC210627.

In one specific embodiment, the combination therapy described herein comprises administration of an inhibitor of BRAF(V006E) that is PLX4720 and an inhibitor of DHODH that is leflunomide or teriflunomide. In another specific embodiment, the combination therapy described herein comprises administration of an inhibitor of BRAF (V006E) that is PLX4032 and an inhibitor of DHODH that is leflunomide or teriflunomide.

In another embodiment, the invention contemplates the practice of the method in conjunction with other therapies such as conventional chemotherapy, radiation therapy or surgery directed against solid tumors and for control of establishment of metastases. The administration of angiogenesis-inhibiting amounts of combination therapy may be conducted before, during or after chemotherapy, radiation therapy or surgery.

Pharmaceutical Compositions and Administration

Embodiments of the invention comprise administering to a subject an inhibitor of oncogenic BRAF and/or and inhibitor of DHODH for the treatment of melanoma. The administration of the DHODH inhibitor, or combination therapy comprising administration of a DHODH and a BRAF inhibitor, may be for either "prophylactic" or "therapeutic" purpose. When provided prophylactically, therapy is provided in advance of any symptom. The prophylactic administration of the therapy serves to prevent formation of melanoma. Prophylactic administration may be given to a patient with, for example, a family history of cancer, or a patient that has had a melanoma removed surgically. Alternatively, administration of the combination therapy may be given to a patient with rising cancer marker protein levels, for example melanoma markers described in PCT Publications WO 2008/141275, WO 2009/073513, or in U.S. Pat. No. 7,442,507

When provided therapeutically, the administration of the DHODH inhibitor, or combination therapy comprising administration of a DHODH inhibitor and a BRAF inhibitor, is provided at (or after) the onset of a symptom, or indication of melanoma.

For the combination therapy, the inhibitor of DHODH and the inhibitor of BRAF can be present in the same or different pharmaceutical composition. When administrated at different times, the inhibitor of DHODH and the inhibitor of BRAF can be administered within 5 minutes, 10 minutes, 20 minutes, 60 minutes, 2 hours, 3 hours, 4, hours, 8 hours, 12 hours, 24 hours of administration of the other. When the inhibitors are administered in different pharmaceutical compositions, routes of administration can be different.

The effective dosage range for the administration of the inhibitors depends upon the form of the inhibitor and its potency. It is an amount large enough to produce the desired effect in which symptoms of melanoma are ameliorated (e.g. inhibition of tumor growth). The phrase "therapeutically-effective amount" as used herein means that amount of inhibitory compound or composition comprising the inhibitor/s which is effective for producing the desired therapeutic effect, in at least a sub-population of cells, in a subject at a reasonable benefit/risk ratio applicable to any medical treatment. For example, an amount of a compound administered to a subject that is sufficient to produce a statistically significant, measurable change in at least one symptom of melanoma. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. There are preclinical melanoma models that are well known to those of skill in the art which can be used to determine therapeutically effective amounts of the compound or agents and to optimize administration regimes. See for example Yang et al. (2010) RG7204 (PLX4032), A selective BRAFV600E inhibitor, displays potent antitumor activity in preclinical melanoma models, *Cancer Research,* 70:5518-5527, which is herein incorporated by reference its entirety.

In one embodiment, a therapeutically effective amount of oncogenic BRAF inhibitor (e.g BRAF(V600E)) and/or DHODH inhibitor, inhibits melanoma tumor volume in a preclinical model by at least 5%, at least 10%, at least 20%, at least 30%, at least 40%, at least 50%, at least 60%, at least 70%, at least 80%, at least 90% and reduces at least one symptom of melanoma by at least 5%, at least 10%, at least 20%, at least 30%, at least 40%, at least 50%, at least 60%, at least 70%, at least 80%, or at least 90%. For example, tumor volumes in xenograft mice can be calculated using the following ellipsoid formula: $[D \times (d2)]/2$, in which D represents the large diameter of the tumor, and d represents the small diameter. Tumor volumes of treated groups are presented as percentages of tumor volumes of the control groups (% T/C) using the following formula: $100 \times [(T-T_0)/(C-C_0)]$, in which T represents mean tumor volume of a treated group on a specific day during the experiment, $T_0$ represents mean tumor volume of the same treated group on the first day of treatment, C represents mean tumor volume of a control group on the specific day during the experiment, and $C_0$ represents mean tumor volume of the same treated group on the first day of treatment. Percent tumor growth inhibition can be calculated as 100–% T/C, with >100% tumor growth inhibition representing regression. Survival can be calculated using a predefined cutoff volume of 2,000 mm$^3$ as a surrogate for mortality (See e.g. Yang et al. (2010), Supra).

In one embodiment a therapeutically effective amount of the DHODH inhibitor inhibits the enzymatic activity of DHODH by at least 5%, at least 10%, at least 20%, at least 30%, at least 40%, at least 50%, at least 60%, at least 70%, at least 80%, or at least 90% and reduces at least one symptom of melanoma by at least 5%, at least 10%, at least 20%, at least 30%, at least 40%, at least 50%, at least 60%, at least 70%, at least 80%, or at least 90%.

In one embodiment a therapeutically effective amount of the oncogenic BRAF inhibitor and/or DHODH inhibitor inhibits cellular proliferation in a preclinical model by at least 5%, at least 10%, at least 20%, at least 30%, at least 40%, at least 50%, at least 60%, at least 70%, at least 80%, or at least 90% and reduces at least one symptom of melanoma by at least 5%, at least 10%, at least 20%, at least 30%, at least 40%, at least 50%, at least 60%, at least 70%, at least 80%, or at least 90% Inhibition of cellular proliferation may be evaluated by 3-(4,5-dimethylthiazole-2-yl)-2,5-diphenyl-2H-tetrazolium bromide (MTT; Sigma) assay. For example cells can be plated in 96-well microtiter plates at a density of 1,000 to 5,000 cells per well in a volume of 180 μL. Twenty-four hours after cell plating, 20 μL of an appropriate compound/agent dilution can be added to plates in duplicate. The plates may then be assayed for proliferation 6 days after the cells were plated according to the procedure originally described by Mosmann, Rapid colomeric assay for cellular growth and survival: application to proliferation and cytotoxicity assays. *J. Immunol. Methods* 1883;65:55-63). Percent inhibition can then be calculated and the IC50 determined from the regression of a plot of the logarithm of the concentration versus percent inhibition by XLfit (version 4.2; IDBS) using a Dose-Response One-Site Model (#205) (see e.g. Yang et al. Supra)

The therapeutically effective dose can be estimated initially from a suitable cell culture or enzymatic assays (e.g. melanoma cell growth assays, phosphorylation assays, or DHODH enzymatic activity assays), then a dose of each compound and treatment regime may be formulated in animal models to achieve a circulating plasma concentration range that includes the IC50 as determined in cell culture.

For administration to a subject, the compounds or agents can be provided in pharmaceutically acceptable compositions. These pharmaceutically acceptable compositions comprise a therapeutically-effective amount of one or more of inhibitors, formulated together with one or more pharmaceutically acceptable carriers (additives) and/or diluents. The pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally (e.g. as a nasal spray or suppository); or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960. Guidance for formulations can be found in e.g. Remington: The Science and Practice of Pharmacy by Alfonso R. Gelmaro (Ed.) 20$^{th}$ edition: Dec. 15, 2000, Lippincott, Williams $ Wilkins, ISBN: 0683306472, and are briefly described below.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The amount of compound which can be combined with a carrier material to produce a single dosage form will generally be that amount of the compound which produces a therapeutic effect. Generally out of one hundred percent, this amount will range from about 0.1% to 99% of compound, preferably from about 5% to about 70%, most preferably from 10% to about 30%.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycocholate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethyl-ammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

As used herein, the term "administer" or "administering" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

Methods of delivering RNAi interfering (RNAi) agents (e.g., an siRNA), other nucleic acid modulators, or vectors containing modulatory nucleic acids, to the target cells (e.g., melanocytes) can include, for example directly contacting the cell with a composition comprising a modulatory nucleic acid, or local or systemic injection of a composition containing the modulatory nucleic acid. In one embodiment, nucleic acid agents (e.g. RNAi, siRNA, or other nucleic acid) are injected directly into a tumor. In some embodiments modulatory nucleic may be delivered by systemic administration, wherein the nucleic acid is complexed with, or alternatively contained within a carrier. Example carriers for modulatory nucleic acid compounds include, but are not limited to, peptide carriers, viral vectors, gene therapy reagents, and/or liposome carrier complexes and the like.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979) also U.S. Pat. Nos. 4,906,474, 4,925,673 and 3,625,214, and Jein, TIPS 19:155-157 (1998), the contents of which are hereby incorporated by reference.

In some embodiments, the compound/agents described herein for treatment of melanoma can be administered to a subject in combination with additional pharmaceutically active agents. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that a compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg etc. . . . . It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg etc.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity.

The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more. The pharmaceutical compositions can be administered during infancy (between 0 to about 1 year of life), childhood (the period of life between infancy and puberty) and during puberty (between about 8 years of life to 18 years of life). The pharmaceutical compositions can also be administered to treat adults (greater than about 18 years of life). A dose administered at least once, may be provided as a bolus, a continuous administration or sustained release. Multiple administration over a period of weeks or months may be preferable. It may also be preferable to administer the dose at least once/week and even more frequent administrations (e.g. daily). Subsequent doses may be administered as indicated.

In one embodiment, the inhibitor of DHODH (e.g. leflunomide) is administered to a subject using an administration regime that results in a steady state concentration of 70 mcg/mL, or 60 mcg/mL, or 50 mcg/mL, 40 mcg/mL, 30 mcg/ml, or 20 mcg/mL (Rozman, B. (2002) Clinical pharmacokinetics of leflunomide, *Clin. Pharmacokinetic*, 41:421-430). In one embodiment, the steady state concentration is 60 mcg/mL or less, 50 mcg/mL or less, 40 mcg/mL or less, 30 mcg/ml or less, or 20 mcg/mL or less.

In one embodiment, the inhibitor of DHODH (e.g. leflunomide) is administered at 100 mg daily for 3 days, followed by lower daily doses of 20 mg/ml for a sustained concentration of 60 mcg/mL.

In one embodiment, the inhibitor of BRAF (e.g. PLX4302) is administered at a dosage of 960 mg twice a day. In one embodiment, the inhibitor of BRAF (e.g. PLX4302) is administered at a dosage less than 900 mg twice a day, less than 850 mg twice a day, less than 800 mg twice a day, or less than 700 mg twice per day.

The efficacy of a given treatment regime for melanoma can be determined by the skilled clinician, for example by assessing physical indicators of melanoma, such as e.g., tumor size or lesion size, metastasis, tumor growth rate, etc. However, a treatment is considered "effective treatment," as the term is used herein, if any one or all of the signs or symptoms of the cancer are altered in a beneficial manner, e.g. improved or ameliorated by at least 10% following treatment with a compound or agent that inhibits BRAF and/or DHODH. Efficacy can also be measured by a failure of an individual to worsen as assessed by stabilization of tumor growth, hospitalization or need for medical interventions (i.e., progression of the melanoma is halted or at least slowed). Methods of measuring these indicators are known to those of skill in the art and/or described herein. Treatment includes in an individual includes: (1) inhibiting the disease, e.g., arresting, or slowing melanoma tumor or lesion growth; or (2) relieving the disease, e.g., causing regression of symptoms, reducing tumor or lesion size; and (3) preventing or reducing the likelihood of the development of melanoma, or preventing metastasis of the melanoma.

Screening Methods

In another aspect of the invention, methods of screening for compounds that are useful for treatment of melanoma are provided.

We have previously described a transgenic zebrafish melanoma model (Patton, E. E. et al. BRAF mutations are sufficient to promote nevi formation and cooperate with p53 in the genesis of melanoma. *Curr. Biol* 15, 249-54 (2005); U.S. 2008/0072337). Transgenic zebrafish expressing human BRAF(V600E) under the melanocyte-specific mitf promoter (mitf-BRAF(V600E)) develop melanoma at 4-12 months of age when crossed with p53−/− mutants. Herein, we determined, by gene expression analysis, that the melanoma cells adopted a fate similar to that of the BRAFV600E; p53−/− embryos (See Examples). We discovered that BRAF (V600E):p53−/− embryos exhibit an abnormal expansion in the number of crestin+ progenitors (marker of embryonic neural crest progenitors), and that in the adult BRAF (V600E):p53−/− virtually all tumor cells, but no normal cells, are positive for crestin. Crestin is normally downregulated after terminal differentiation of neural crest progenitors. Thus, we developed a screen for compounds useful for melanoma treatment that comprises screening for inhibitors of neural crest progenitors during embryogenesis, e.g. screening for inhibitors of the crestin+ lineage.

Methods of screening for agents that inhibit melanoma growth are provided. The method comprises: (a) contacting a zebrafish embryo with a test agent for a period of time (e.g. hours, days, or weeks), (b) rinsing the embryos of step (a); and (c) assaying the number of neural crest progenitors as compared to a control zebrafish embryo that has not been contacted with the test agent, wherein a reduced number of neural crest progenitors indicates that the compound is capable of inhibiting melanoma growth.

In one embodiment, the method further comprises the step of measuring inhibition of melanoma growth, e.g. in a transgenic melanoma zebrafish model, or in a melanoma proliferation assay, or mouse xenograft melanoma model (See e.g. Examples and U.S. patent application publication 2008/0072337).

The embryos may be contacted at any time of embryonic development. In one embodiment, the embryos are contacted with an agent at approximately 20%, 30%, 40%, 50%, 60%, or 70% epiboly.

In one embodiment, the zebrafish embryos used in the screen are wild type (wt) zebrafish embryos.

In one embodiment, inhibition of neural crest progenitors is scored by monitoring for inhibition of crestin expression in cells of the neural crest of the embryo. Crestin expression can be monitored by any means known to those of skill in the art, including but not limited to in situ hybridization with a crestin riboprobe. When monitoring expression of crestin by ISH the method further comprises the step of fixing the embryos prior to performing ISH using means well known to those of skill in the art (e.g. fixing in PFA and methanol). Expression can be scored using visualization, or other means known to those of skill in the art, e.g. manual scoring may comprises assigning a score within a range of 1 (no crestin staining) to 3 (no change in crestin) to 5, a marked increase in crestin, e.g. compounds having a score of 2 or less may be considered to inhibit the number of crestin$^+$ cells.

In one embodiment the zebrafish embryos are of mitfa-GFP transgenic zebrafish (express green fluorescent protein (GFP) operably linked to mitfa melanocyte specific promoter), and inhibition of neural crest progenitors is scored by monitoring for inhibition of the number of melanocytes along the neural crest of the embryo, e.g. by determining the amount of GFP expression in the neural crest, e.g. by visual scoring or computerized means.

In one embodiment, inhibition of neural crest progenitors is scored by monitoring for inhibition of sox10 expression, or dct expression in cells of the neural crest of the embryo.

The methods of screening described herein, can be performed as high throughput assays. For example a plurality of embryos may be contacted with a plurality of compounds or agents, e.g. in a multi-well format, and the step of assaying the number of neural crest progenitors may be atomized, e.g. using automated in situ hybridization or fluorescence imaging. Compounds showing inhibition of neural crest progenitors may then be selected.

An exemplary assay may involve plating wild type zebrafish embryos in multi-well plates in appropriate media, e.g. at a density of about 10 embryos per well, and at about 50% epiboly, adding the test agent to the wells. Any concentration of test agent can be used. In one embodiment, the test agent concentration ranges from, 1 uM to 50 uM, 0.1 nm to 1000 mM, or e.g. 1 uM to 1 mm, or more. High concentrations may be toxic to the embryos, which can easily be determined by testing and the concentration can be adjusted to minimize toxicity. 24 hours after treatment the cells embryos are rinsed of test drug and fixed for in situ hybridization, e.g. of crestin, sox10, dct, edn, etc. Compounds resulting in statistically significant inhibition of neural crest progenitor cells are selected, and are optionally tested for quantitation of inhibition of melanoma growth in other assays, e.g. % inhibition of melanocyte proliferation (See Examples), or tumor inhibition studies, e.g. using xenograft mice. Means for plating and manipulating zebrafish are well known to those of skill in the art, see e.g. Kaufman, C. K., white, R. M. & Zon, L. chemical genetic screening in zebrafish embryo. *Nat. Protoc.* 4, 1422-1432 (2009). This is merely an exemplary assay, there are multiple means well known to those of skill in the art to monitor neural crest progenitor cell formation that are suitable for use in the screening assay.

In an alternative embodiment, the zebrafish embryo used in the screening methods described herein, has been genetically manipulated to express a nucleic acid encoding a mutant human BRAF and a mutant tumor suppressor and/or protooncogene, e.g. mitf-BRAF(V600E); p53−/−, or other oncogenic BRAF zebrafish melanoma models. Such models are described in detail in U.S. patent application publication 2008/0072337, which is herein incorporated by reference in its entirety.

As used herein, the term "test compound" refers to compounds and/or compositions that are to be screened for their ability to inhibit the number of neural crest progenitors. The test compounds can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the test compound is a small molecule.

As used herein, the term "small molecule" refers to in organic or organic compounds. However, small molecules typically are characterized in that they contain several carbon-carbon bonds, and have a molecular weight of less than 5000 Daltons (5 kD), preferably less than 3 kD, still more preferably less than 2 kD, and most preferably less than 1 kD. In some cases it is preferred that a small molecule has a molecular weight equal to or less than 700 Daltons.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used. Compound libraries are well known and readily available in the art. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

In the methods of the invention, the compounds/agents are typically provided free in solution, however the compounds/or agent may be in complex with solid forms.

In some embodiments, the test compound inhibits neural crest progenitors by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control.

Definitions

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, the term "IC50" refers to the concentration of an inhibitor that produces 50% of the maximal inhibition of activity or expression measurable using the same assay in the absence of the inhibitor. The IC50 can be as measured in vitro or in vivo. The IC50 can be determined by measuring activity using a conventional in vitro assay (e.g. protein activity assay, or gene expression assay).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains.

The present invention may be as defined in any one of the following numbered paragraphs.

1. A method for treating melanoma in a subject comprising administering to a subject in need thereof a therapeutically effective amount of an inhibitor of dihydroorotate dehydrogenase (DHODH).

2. The method of para. 1, wherein the inhibitor of dihydroorotate dehydrogenase (DHODH) is selected from the group consisting of: leflunomide, teriflunomide, brequinar, dichloroallyl lawsone, maritimus, redoxal and NSC210627, or a derivative thereof.

3. A method for treating melanoma in a subject comprising administering to a subject in need thereof a therapeutically effective amount of an inhibitor of dihydroorotate dehydrogenase (DHODH) and an effective amount of an inhibitor of oncogenic BRAF.

4. The method of para. 3, wherein the inhibitor of oncogenic BRAF is selected from the group consisting of: a small molecule, a nucleic acid RNA, a nucleic acid DNA, a protein, a peptide, and an antibody.

5. The method of any of para.'s 1-4, wherein the inhibitor of dihydroorotate dehydrogenase is selected from the group consisting of: a small molecule, a nucleic acid RNA, a nucleic acid DNA, a protein, a peptide, and an antibody.

6. The method of any of para.'s 3-5, wherein the oncogenic BRAF is BRAF(V600E).

7. The method of any of para.'s 3-6, wherein the inhibitor of oncogenic BRAF is selected from the group consisting of: Sorafenib, RAF265, XL281, AZ628, GSK2118436, GDC-0879, PLX4032, and PLX4720.

8. The method of any of para.'s 3-5, wherein the inhibitor of dihydroorotate dehydrogenase (DHODH) is selected from the group consisting of leflunomide, teriflunomide, brequinar, dichloroallyl lawsone, maritimus, redoxal and NSC210627.

9. The method of any of para.'s 3-6, wherein the inhibitor of oncogenic BRAF is PLX4032 and the inhibitor of dihydroorotate dehydrogenase (DHODH) is leflunomide, or a derivative thereof.

10. The method of any of para.'s 3-6, wherein the inhibitor of oncogenic BRAF is PLX4720 and the inhibitor of dihydroorotate dehydrogenase (DHODH) is leflunomide, or a derivative thereof.

11. The method of any of para.'s 3-10, wherein the inhibitor of oncogenic BRAF and inhibitor of dihydroorotate dehydrogenase (DHODH) are administered to the subject sequentially or simultaneously.

12. A method of screening for an agent that inhibits melanoma growth comprising (a) contacting a zebrafish embryo with a test agent for a period of time,
  (b) rinsing the test agent from the embryos of step (a); and
  (c) assaying the number of neural crest progenitors as compared to a control zebrafish embryo that has not been contacted with the test agent,
  wherein a reduced number of neural crest progenitors indicates that the compound is capable of inhibiting melanoma.

13. The method of para. 12, wherein the reduced number of neural progenitors is due to their differentiation to melanocytes (e.g. a measured using melanocyte markers or assessing terminal differentiation)

14. The method of paras. 12-13, wherein the zebrafish embryo is a wild type zebra fish embryo.

15. The method of any of para.'s 12-14, wherein the zebrafish embryo is a transgenic zebra fish embryo.

16. The method of para. 15, wherein the transgenic zebrafish expresses green fluorescent protein operably linked to the melanocyte mitfa promoter.

17. The method of any of para.'s 1-16, wherein the number of neural crest progenitors is assayed by monitoring crestin expression.

18. The method of any of para.'s 1-17, wherein the number of neural crest progenitors is assayed by monitoring sox10 expression.

19. The method of any of para.'s 1-18, wherein the number of neural crest progenitors is assayed by monitoring dct expression.

20. Use of an effective amount of an inhibitor of dihydroorotate dehydrogenase (DHODH) for the manufacture of a medicament for treatment of melanoma.

21. The use of para. 20, wherein the inhibitor of dihydroorotate dehydrogenase (DHODH) is selected from the group consisting of: leflunomide, teriflunomide, brequinar, dichloroallyl lawsone, maritimus, redoxal and NSC210627, or a derivative thereof.

22. Use of an effective amount of an inhibitor of dihydroorotate dehydrogenase (DHODH) and an effective amount of an inhibitor of oncogenic BRAF for the treatment of melanoma.

23. The use of para. 22, wherein the inhibitor of oncogenic BRAF is selected from the group consisting of: a small molecule, a nucleic acid RNA, a nucleic acid DNA, a protein, a peptide, and an antibody.

24. The use of any of para.'s 19-23, wherein the inhibitor of dihydroorotate dehydrogenase is selected from the group consisting of: a small molecule, a nucleic acid RNA, a nucleic acid DNA, a protein, a peptide, and an antibody.

25. The use of any of the para.'s 21-24, wherein the oncogenic BRAF is BRAF(V600E).

26. The use of any of para.'s 21-25, wherein the inhibitor of oncogenic BRAF is selected from the group consisting of: Sorafenib, RAF265, XL281, AZ628, GSK2118436, GDC-0879, PLX4032, and PLX4720.

27. The use of any of para.'s 21-26, wherein the inhibitor of dihydroorotate dehydrogenase (DHODH) is selected from the group consisting of leflunomide, teriflunomide, brequinar, dichloroallyl lawsone, maritimus, redoxal and NSC210627.

28. The use of any of para.'s 21-27, wherein the inhibitor of oncogenic BRAF is PLX4032 and the inhibitor of dihydroorotate dehydrogenase (DHODH) is leflunomide, or a derivative thereof.

29. The use of any of para.'s 21-28, wherein the inhibitor of oncogenic BRAF is PLX4720 and the inhibitor of dihydroorotate dehydrogenase (DHODH) is leflunomide, or a derivative thereof.

30. The method of any of para.'s 21-29, wherein the inhibitor of oncogenic BRAF and inhibitor of dihydroorotate dehydrogenase (DHODH) are administered to the subject sequentially or simultaneously.

All references described herein, in the Examples and throughout the Specification, are incorporated herein by reference in their entirety.

EXAMPLES

Example I

Figure 1B:
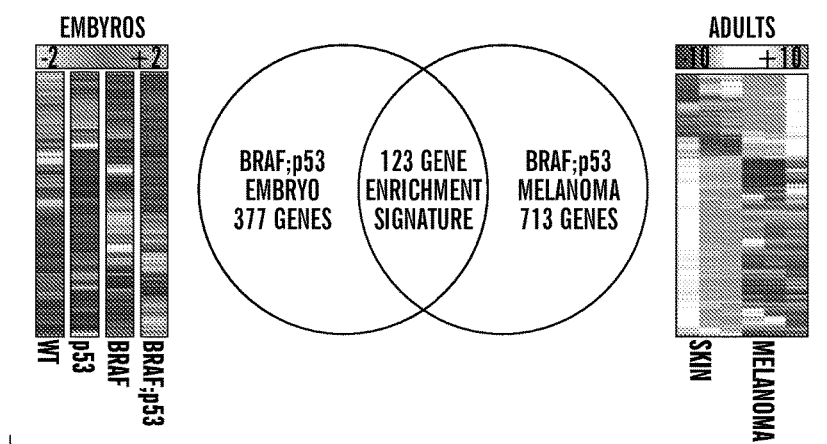

In melanoma, it is unknown to what extent $BRAF^{V600E}$ mutations depend upon transcriptional programs present in the developmental lineage of tumor initiation. These programs may be therapeutic targets when combined with $BRAF^{V600E}$ inhibition. We have utilized zebrafish embryos to identify small molecule suppressors of neural crest progenitors which give rise to melanoma. Transgenic zebrafish expressing human $BRAF^{V600E}$ under the melanocyte-specific mitf promoter (mitf-$BRAF^{V600E}$) develop melanoma at 4-12 months of age when crossed with $p53^{-/-}$ mutants (FIG. 1a). As the mitf promoter drives $BRAF^{V600E}$ starting at 16 hours post fertilization (hpf), overlapping with other markers such as sox10, events that occur early in embryogenesis are analogous to those occurring at tumor initiation. To gain insight into initiating events, we compared gene expression profiles of BRAF$^{V600E}$;p53$^{-/-}$ embryos to BRAF$^{V600E}$; p53$^{-/-}$ melanomas using Gene Set Enrichment Analysis (GSEA) (FIG. 1b). This revealed a 123 gene overlap signature, notable for markers of embryonic neural crest progenitors (crestin, sox10, ednrb) and melanocytes (tyr, dct) (data not shown). This is similar to that of a multipotent neural crest progenitor, and suggested that the melanoma adopted this fate.

Figure 1C:
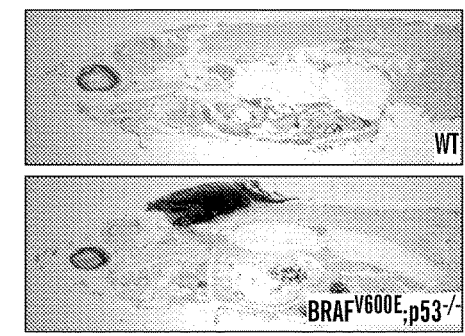
Figure 9A:
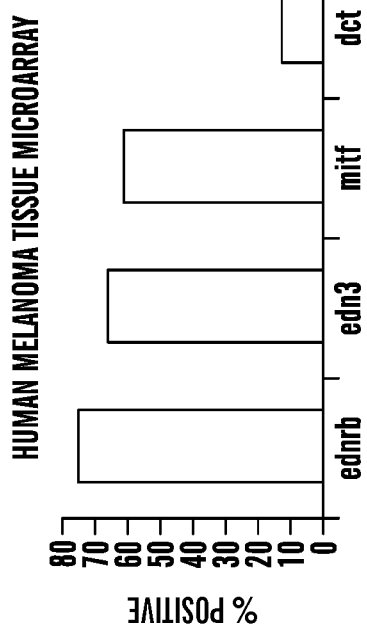
FIGS. 9a to 9b, show a graph of a human melanoma tissue microarray (n=70 samples) which was analyzed for markers of neural crest progenitors (ednrb, edn3) and melanocyte progenitors (mitf, dct). The majority of human melanomas are positive for neural crest markers but only a fraction express more differentiated markers.
Figure 9B:
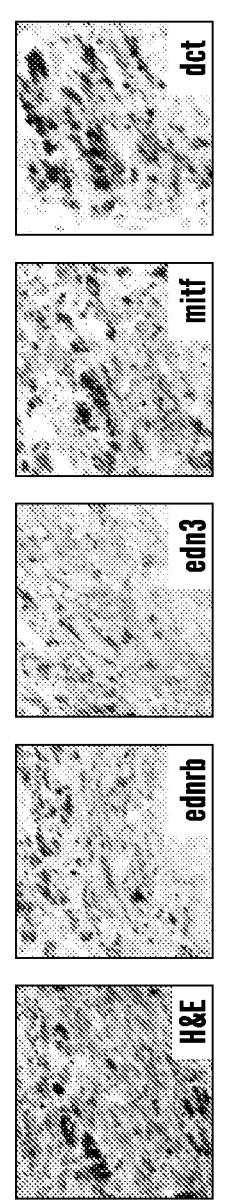

We analyzed alterations in embryonic neural crest development using in situ hybridization (ISH). At 24 hpf, BRAF$^{V600E}$;p53$^{-/-}$ embryos exhibit an abnormal expansion in the number of crestin$^+$ progenitors, along with an increase in other markers from the 123 gene signature such as spry4 and rab3il1 and eden1 (data not shown). Hema toxylin & Eosin (H & E) and crestin ISH on zebrafish melanoma from the dorsum of the fish. Although only a small fraction of the tumor shows pigmented cells, virtually the entire tumor mass was positive for the neural crest marker crestin (data not shown). By 72 hpf, crestin aberrantly persists within the head, tail and dorsal epidermis only in BRAF$^{V600E}$;p53$^{-/-}$ embryos and is absent in non tumor borne strains (data not shown). crestin, a zebrafish specific gene[2], is normally downregulated after terminal differentiation of neural crest progenitors[3], suggesting that activated BRAF$^{V600E}$ promotes maintenance of multipotency in neural crest progenitors, which become expanded during tumorigenesis. In adult BRAF$^{V600E}$;p53$^{-/-}$ melanomas, virtually all tumor cells, but no normal cells, were positive for crestin (FIG. 1c). Only 10-15% of the melanoma cells are pigmented (FIG. 9), consistent with the concept that adult zebrafish melanomas retain a progenitor-like state. A human melanoma tissue array showed similar findings: 75.0% were positive for the neural crest progenitor gene ednrb, but 12.8% for the melanocyte lineage marker dct (FIG. 9), in agreement with findings that most human melanomas express the neural crest marker sox10[4]. These data indicate that the majority of human melanomas reflect events that lead to the maintenance of a neural crest progenitor phenotype[5].

Figure 2A:
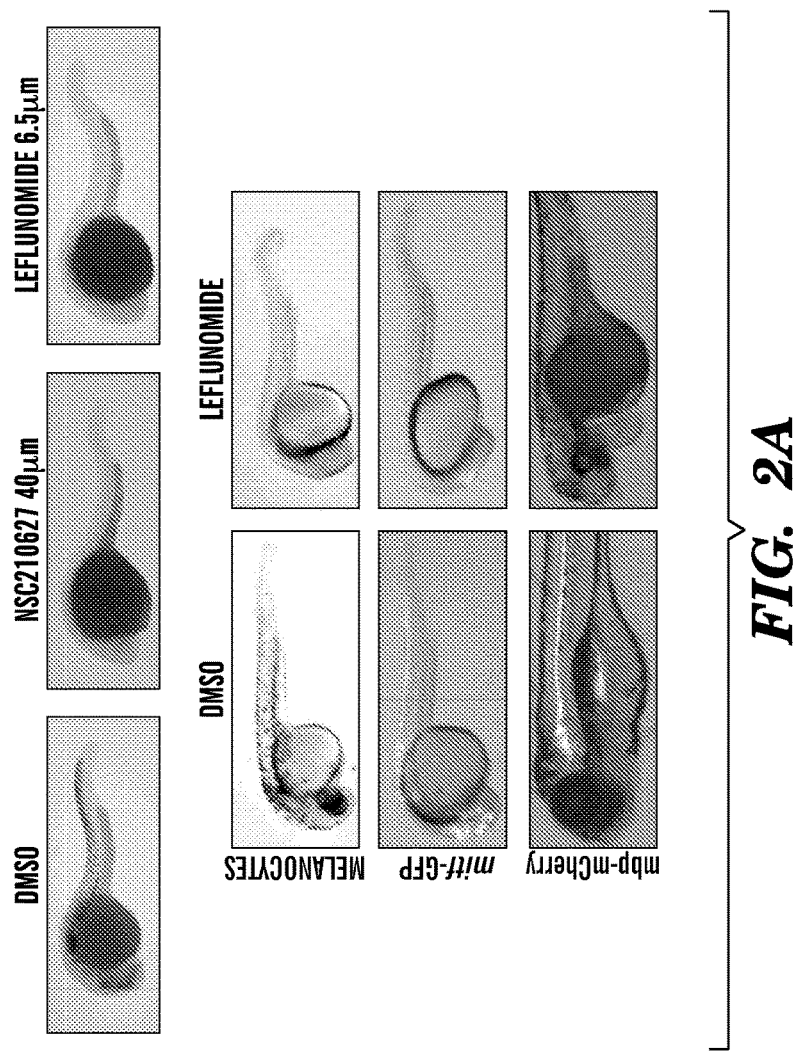
FIGS. 2a to 2b show ISH staining in Zebrafish. A chemical genetic screen to identify suppressors of neural crest development.
Figure 10:
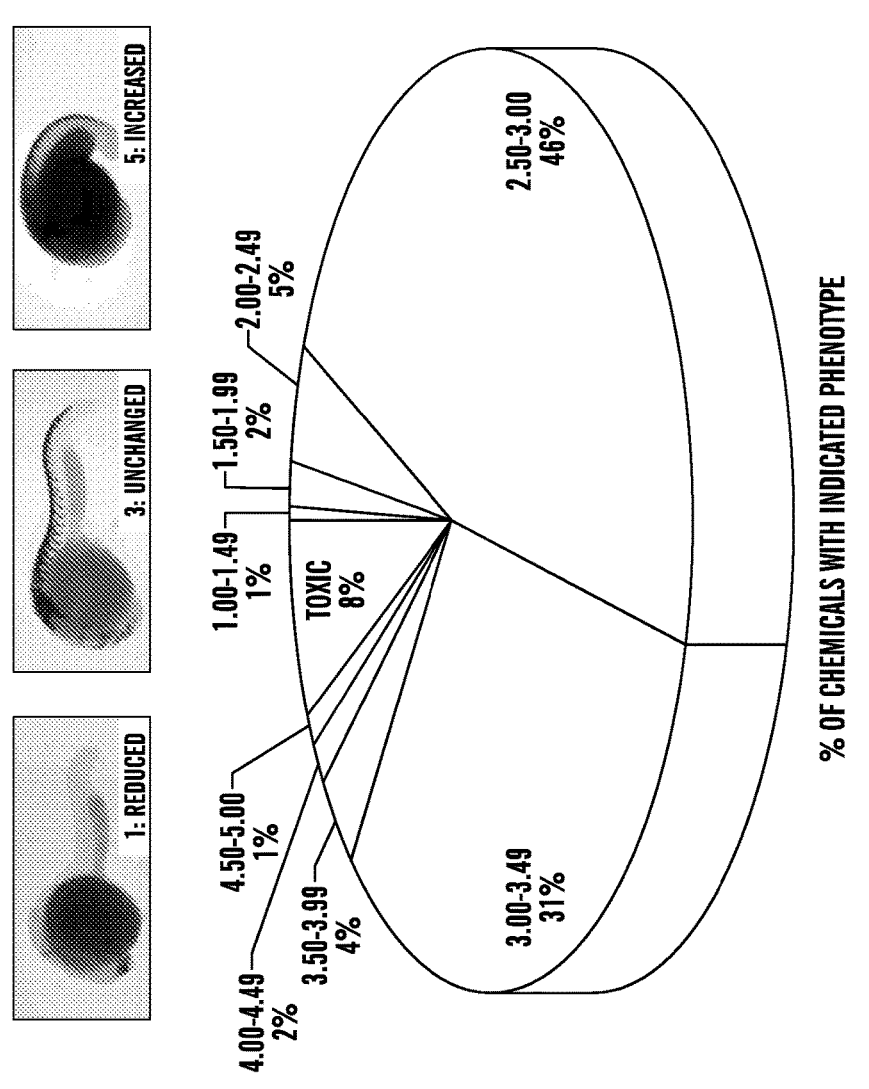
FIG. 10 shows cumulative results of the chemical screen described in the Methods section. 2000 chemicals were screened, and positive "hits" were those with a staining score of less than 2 (i.e. 3%). Representative examples of each score are shown on top. The percentage of chemicals resulting in a given score are shown below.
Figure 11:
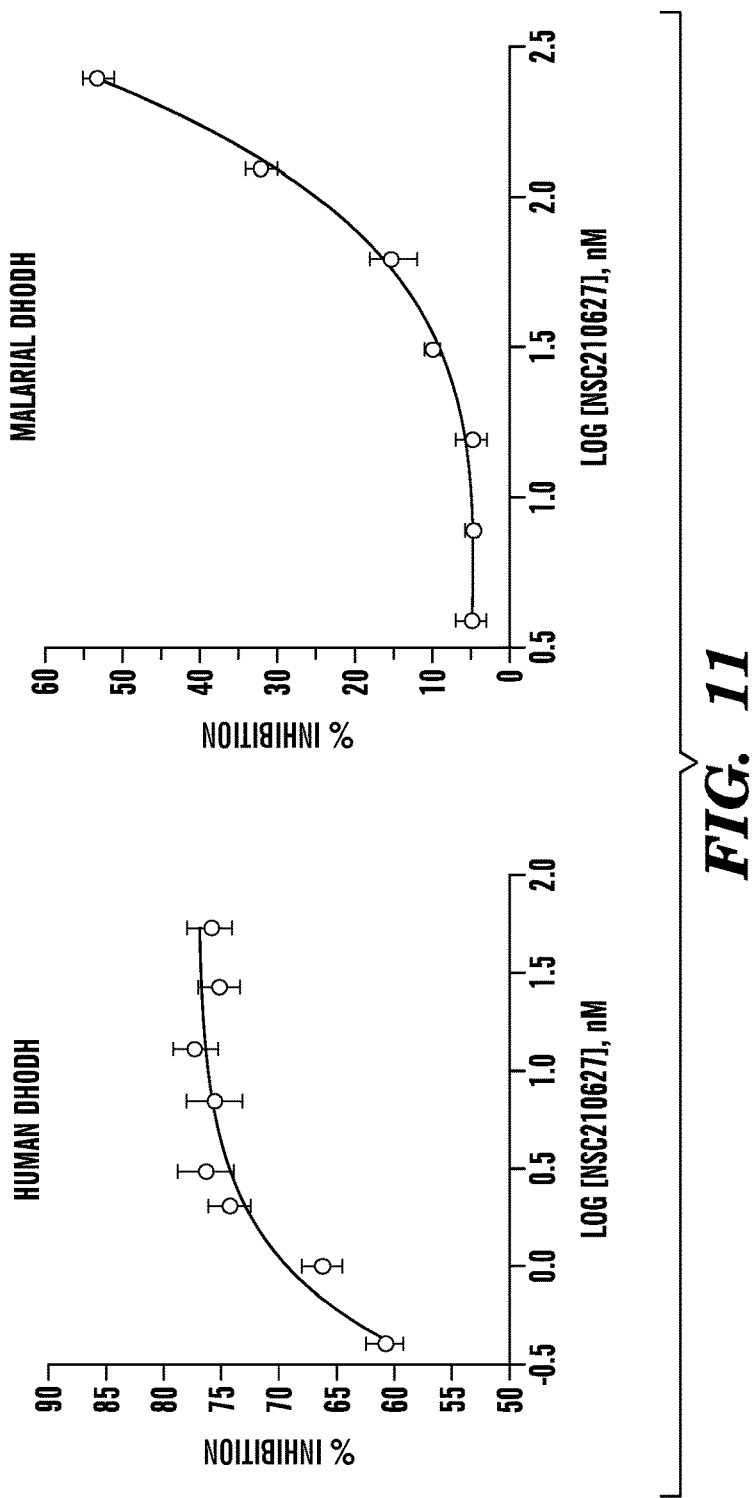
FIGS. 11 shows graphs depicting enzymatic inhibition. The effect of NSC210627 on purified human and malarial DHODH. This demonstrates a strong inhibition of both enzymes, at lower concentrations in the human versus malarial forms. Error bars are mean+/−SEM of n=3 replicates.

We hypothesized that chemical suppressors of neural crest progenitors would have utility in treatment of melanoma. We screened 2,000 chemicals to identify inhibitors of the crestin$^+$ lineage during embryogenesis. Most chemicals (90%) had minimal effect or were toxic (FIG. 10). NSC210627, a molecule of unknown function, strongly abrogated expression of crestin (FIG. 2a, left and middle). The chemoinformatic Discoverygate algorithm[6] revealed similarity between NSC210627 and brequinar (FIG. 5), an inhibitor of dihydroorotate dehydrogenase (DHODH)[7]. NSC210627 inhibited DHODH activity in vitro (FIG. 11). Leflunomide, a structurally distinct DHODH inhibitor[8], phenocopied NSC210627 (FIG. 2a, right) and was used for further studies given its availability.

Figure 2B:
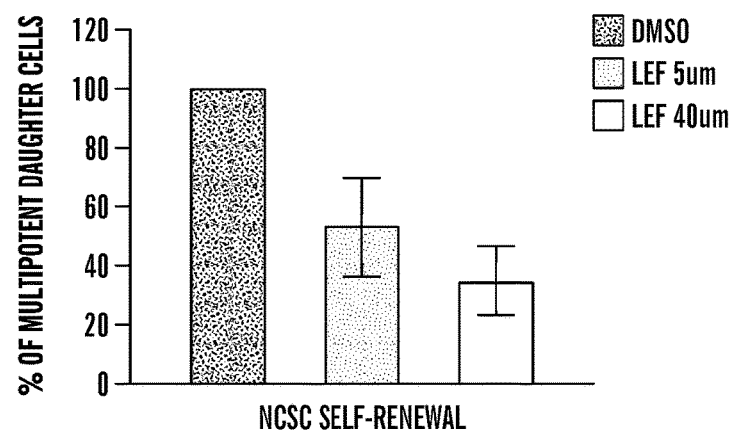
Figure 12:
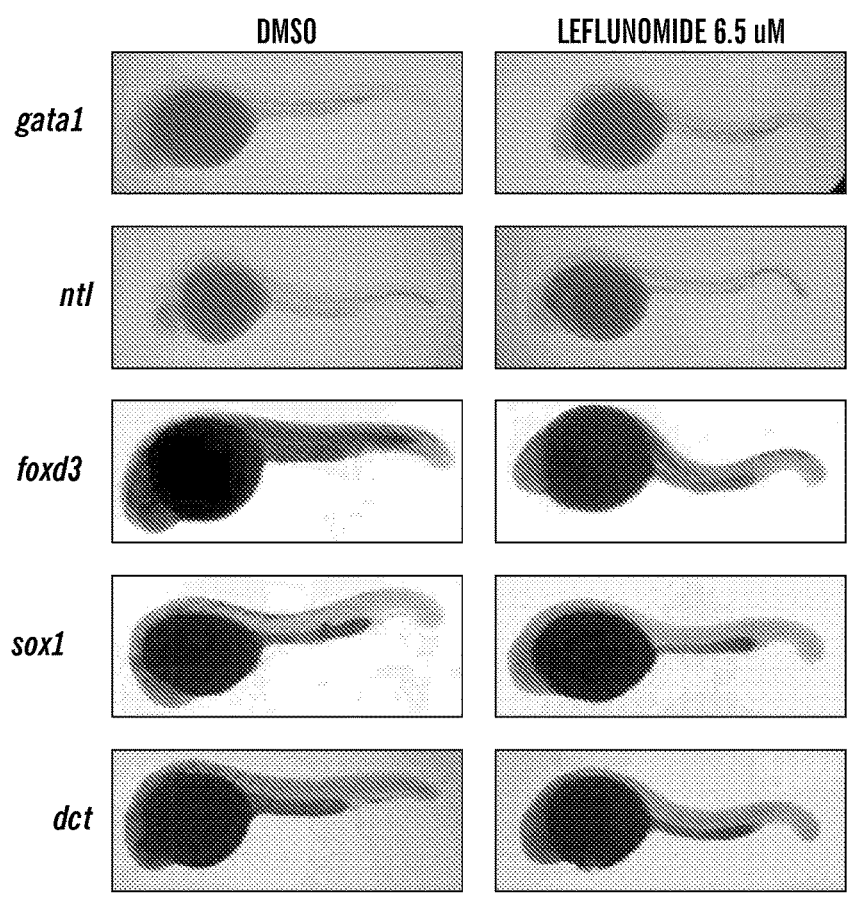
FIG. 12 shows in situ hybridization for neural crest and non-neural crest lineages in the presence of leflunomide. No significant difference is seen in intensity for the mesoderm marker nt1 (although the pattern of expression is altered in some embryos) and blood marker gata1. A disruption in the pattern of foxd3 expression, and absence of sox10 and dct expression confirms broad defects in neural crest development in the presence of leflunomide.

We examined neural crest derivatives affected by leflunomide. Treated zebrafish embryos were devoid of pigmented melanocytes at 36-48 hpf (FIG. 2a-2b) and iridophores (data not shown) at 72 hpf. DHODH inhibition led to a loss of ventral melanocytes in stage 38 Xenopus embryos (data not shown) [Leflunomide treatment (2.5 uM) from 5-72 hpf showed a reduction of reflective iridophores on the surface of the eye. Also microphthalmia was induced by leflunomide. Melanocytes were present in this animal due to the lower dose of leflunomide used (data not shown). Also seen was a reduction of ventral melanocytes in Xenopus embryos treated with the DHODH inhibitor NSC210627) data not shown)]. Leflunomide led to a nearly complete loss of mitf-GFP+ cells at 24 hpf (FIG. 2a-2b), reduction of myelin basic protein (mbp)-mCherry glial cells, and jaw cartilage disruption at 72 hpf (FIG. 2a-2b and data not shown). Leflunomide reduced expression of sox10 and dct while leaving other lineages such as blood and notochord less affected (FIG. 12). Microarray analysis of leflunomide treated embryos showed downregulation of 49% of the genes upregulated in the 123-gene melanoma signature, and over half of those are neural crest related (data not shown).

Figure 6A:
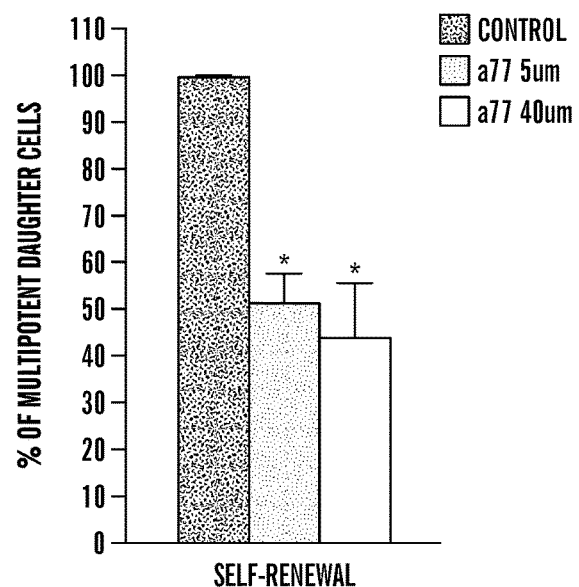
FIGS. 6a to 6c: The effects the leflunomide derivative A771726, on rat neural crest stem cells.
Figure 6B:
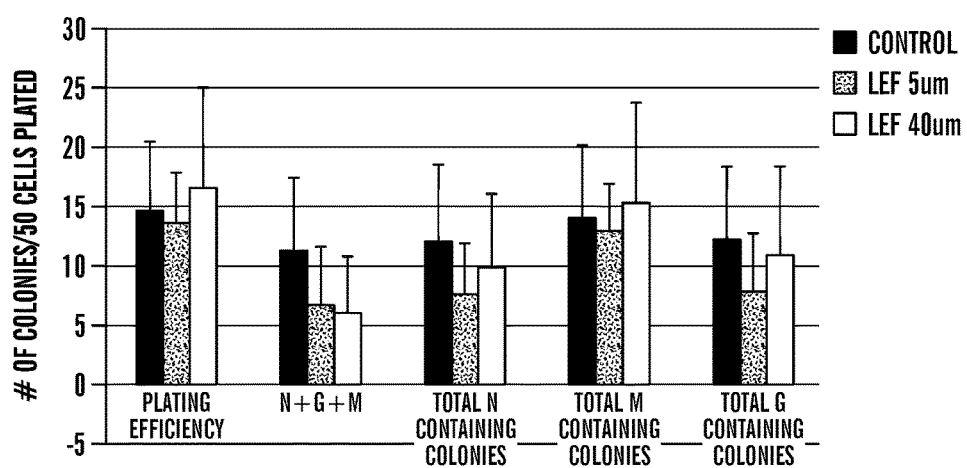
Figure 6C:
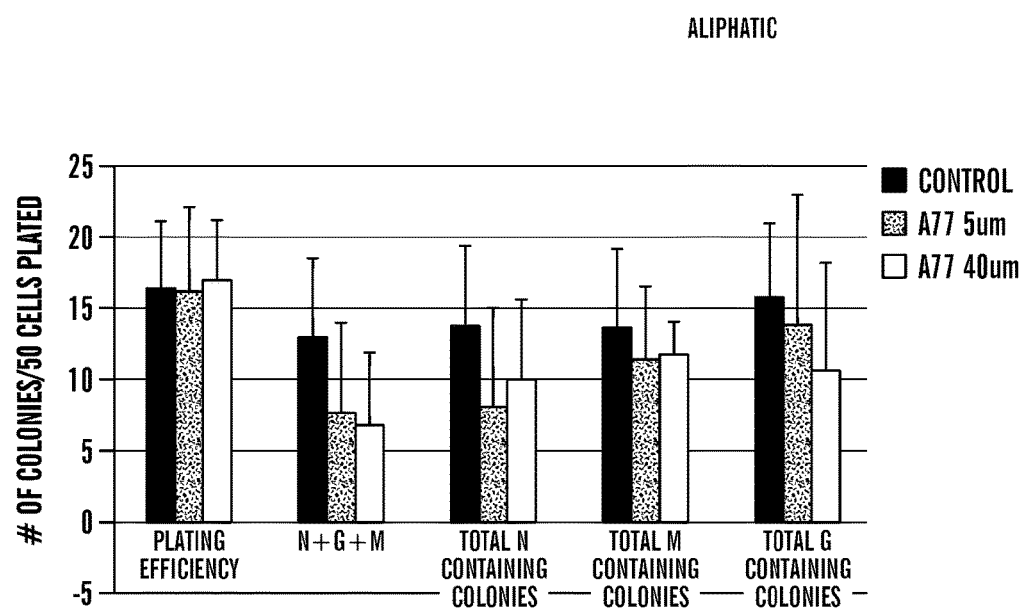
Figure 7B:
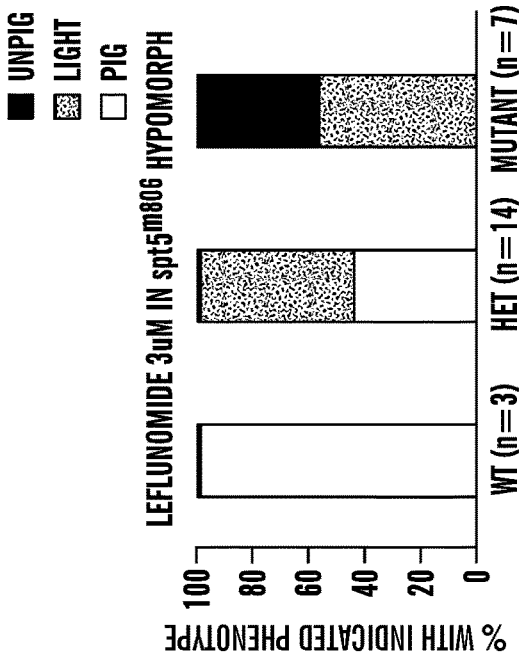
FIGS. 7a to 7d show graphs of the effect of low-doses of leflunomide on pigmentation in the spt5$_{m806}$ hypomorphic mutant. Quantification of the effect described in FIG. 3a, in which 3, 4 or 5 uM leflunomide was applied to a spt5$^{m806}$ hypomorphic incross.
Figure 7A:
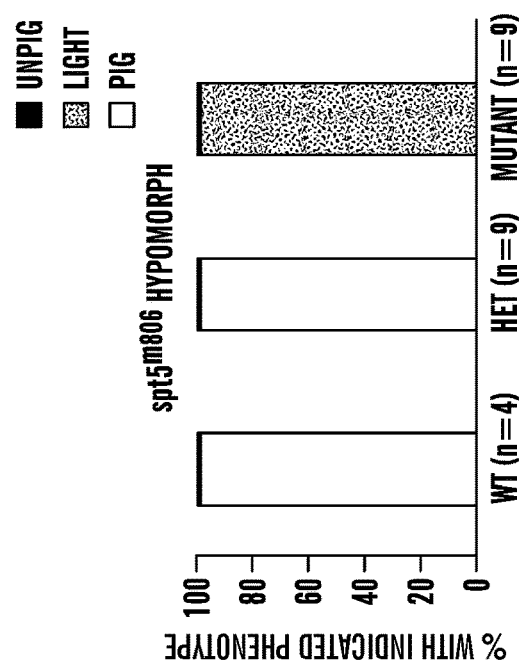
Figure 7C:
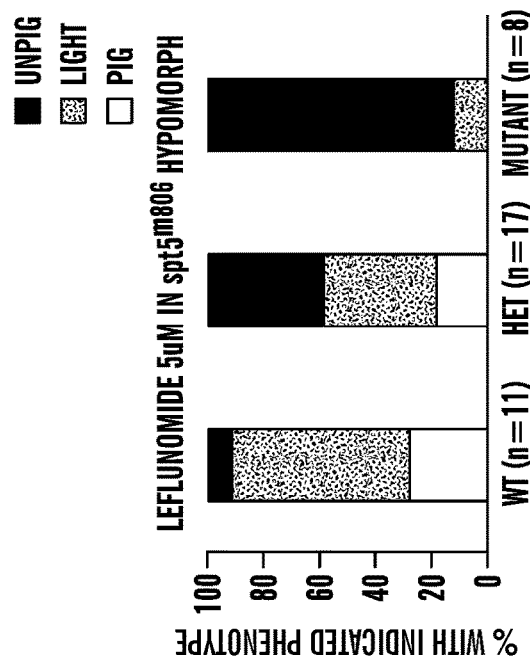
Figure 7D:
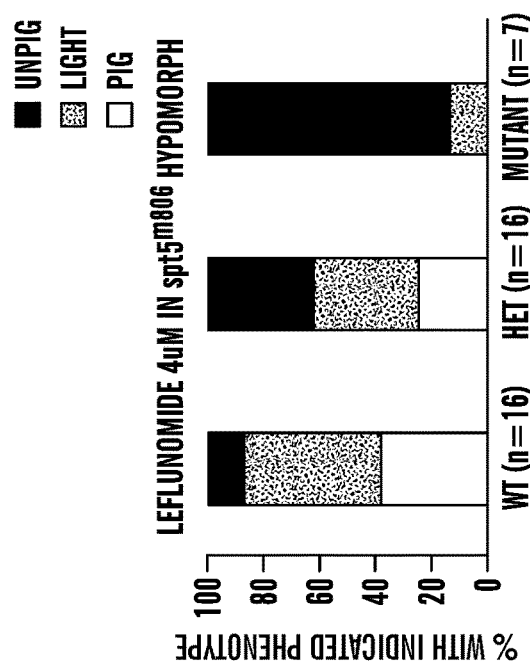

The loss of multiple neural crest derivatives suggested that leflunomide acts on neural crest stem cells. We tested leflunomide, and its derivative A771726, on neural crest stem cells (NCSCs) isolated from the fetal (E14.5) rat gut[9,10]. Both reduced the number of self-renewing NCSCs from primary stem cell colonies to 27+/−5.35% and 35+/− 6.16% of controls (p<0.0003 and p<0.00007, t-test, FIG. 6a). Colony size was reduced compared to controls (by 18% and 24%, respectively, p<0.02, t-test) but there was no effect on differentiation or survival of specific progeny (FIG. 6b, FIG. 6c). These results demonstrate that DHODH inhibitors negatively regulate NCSC self-renewal and affect NCSCs from multiple species.

Figure 3A:
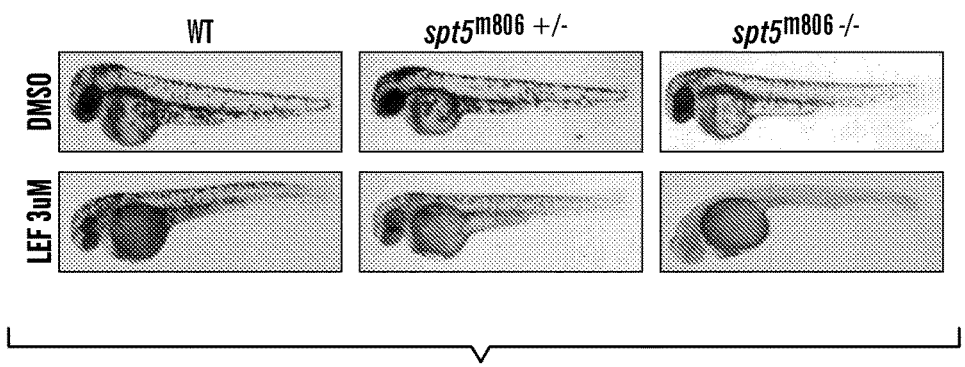
FIGS. 3a to 3c show that DHODH inhibition modulates transcriptional elongation.
Figure 13A:
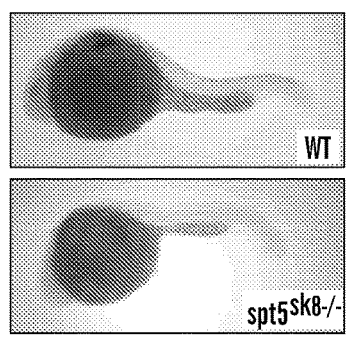
FIGS. 13a to 13c show in situ hybridization and graphs.
Figure 13B:
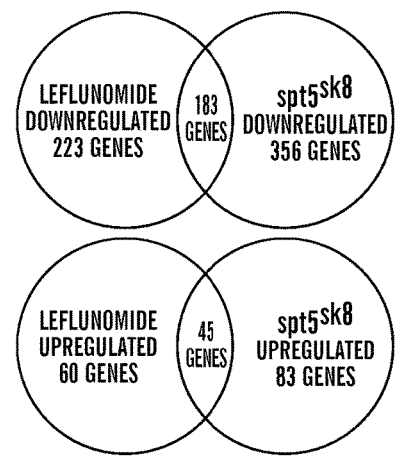

DHODH is the fourth step in the synthesis of pyrimidine nucleotides (NTPs)[11]. We noted striking morphological similarity between leflunomide treated embryos and the spt5/spt6 mutants[12], suggesting that leflunomide acted to suppress transcriptional elongation. We found a lack of crestin expression and pigmented melanocytes (similar to leflunomide) in the spt5$^{sk8}$ null mutant (FIG. 13a). The expression profiles of 24 hpf spt5$^{sk8}$ mutants and leflunomide treated embryos[13] were nearly identical; of 223 genes downregulated after leflunomide treatment, 183 of these were similarly downregulated in spt5$^{sk8}$ (data not shown and FIG. 13b) including neural crest genes (crestin, sox10, mitf) and members of the notch pathway (her2, dlb). We examined the interaction of DHODH with spt5 using low-doses of leflunomide (3-5 uM) incubated with the hypomorphic spt5$^{m806}$ mutant (which has only mild melanocyte defects)[14] and then analyzing the number of pigmented melanocytes. spt5$^{m806}$ embryos showed enhanced sensitivity to leflunomide (FIG. 3a and FIG. 7); at 3 uM, 99% of mutant embryos had few or no melanocytes compared to 0% of wild type embryos (Kruskal-Wallis, p=0.000018). These data confirm that DHODH inhibition impacts transcriptional elongation, consistent with previous data demonstrating that reduction in nucleotide pools in vitro leads to defects in elongation[15].

Figure 13C:
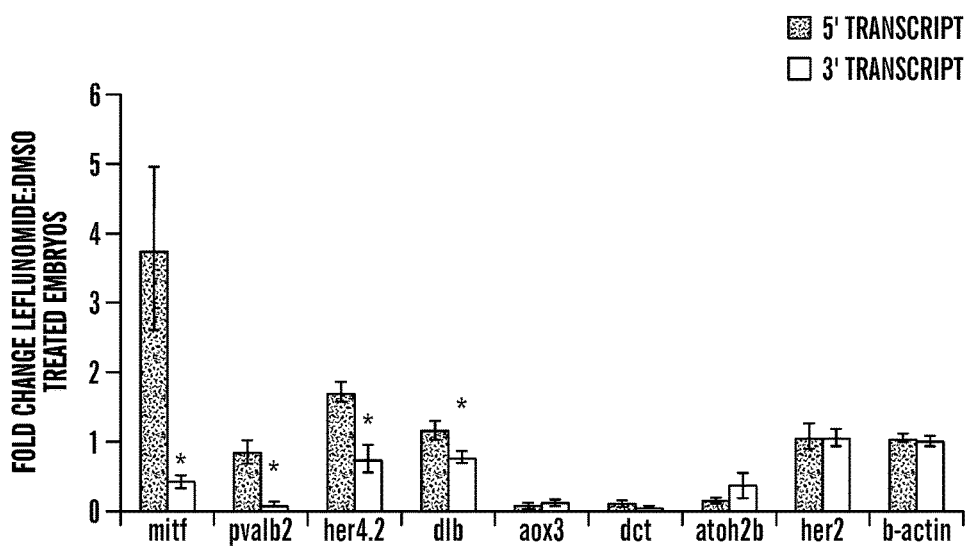

We assessed whether leflunomide specifically caused defects in the transcriptional elongation of genes required for neural crest development using qRT-PCR (FIG. 13c and data not shown). Leflunomide caused no change or an increase of 5' transcript abundance, but a significant downregulation of 3' transcripts of mitf (5':3.75+/−1.19 vs. 3': 0.39+/−0.07 fold, p<0.05), and dlb (5':1.13+/−0.14 vs. 3':0.74+/−0.07 fold, p<0.05), but not in control genes such as beta-actin (5':1.03+/−0.07 vs. 3':0.99+/−0.06 fold, p=NS, t-test). In the presence of leflunomide, transcription is initiated normally, but these transcripts accumulate and do not undergo productive elongation.

Figure 3B:
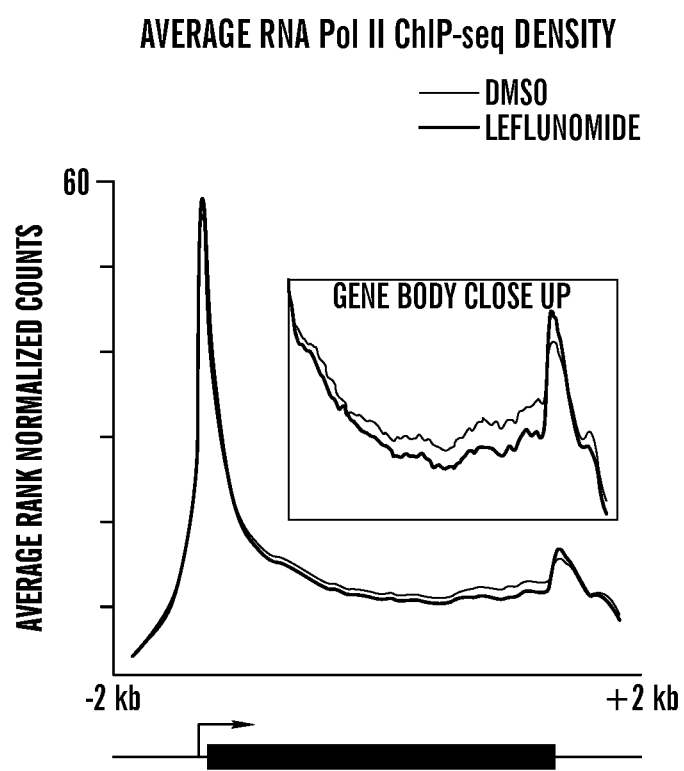
Figure 3C:
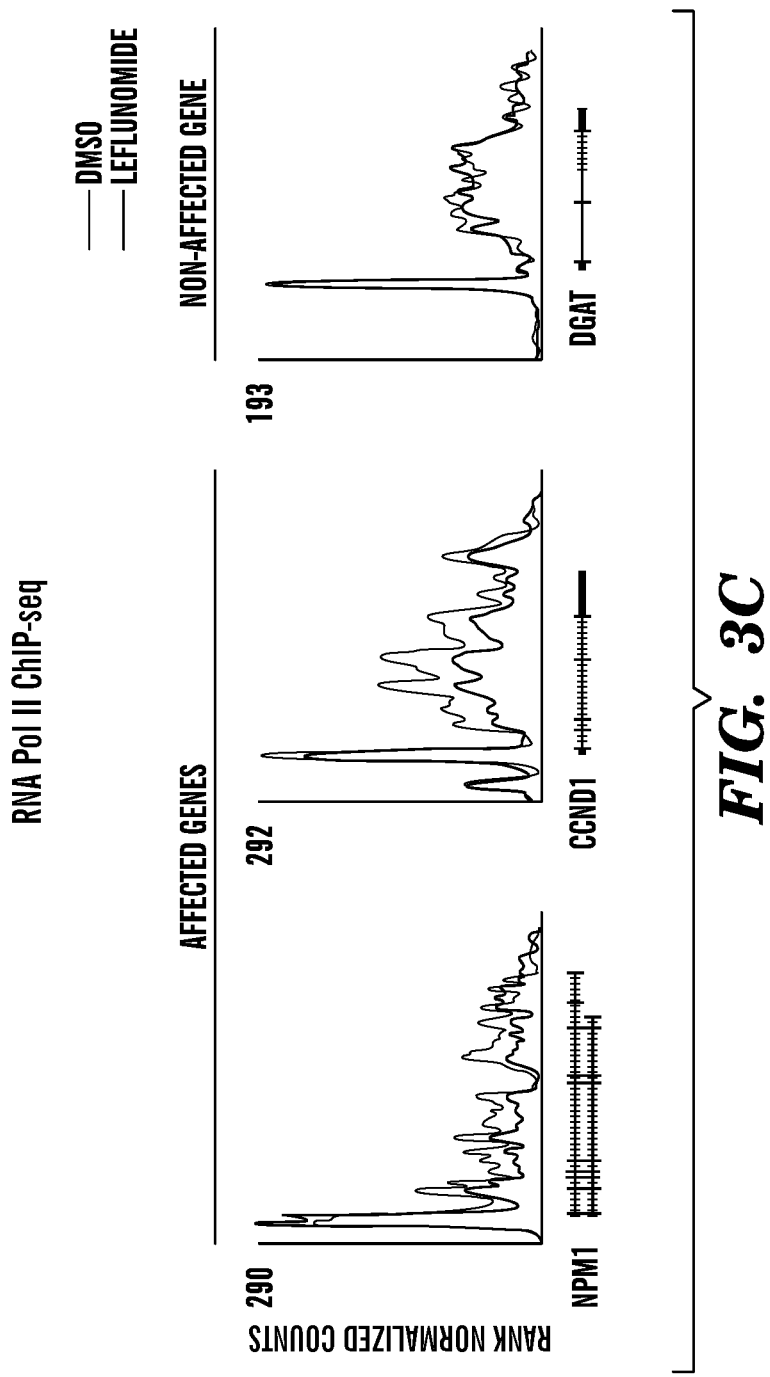
Figure 14A:
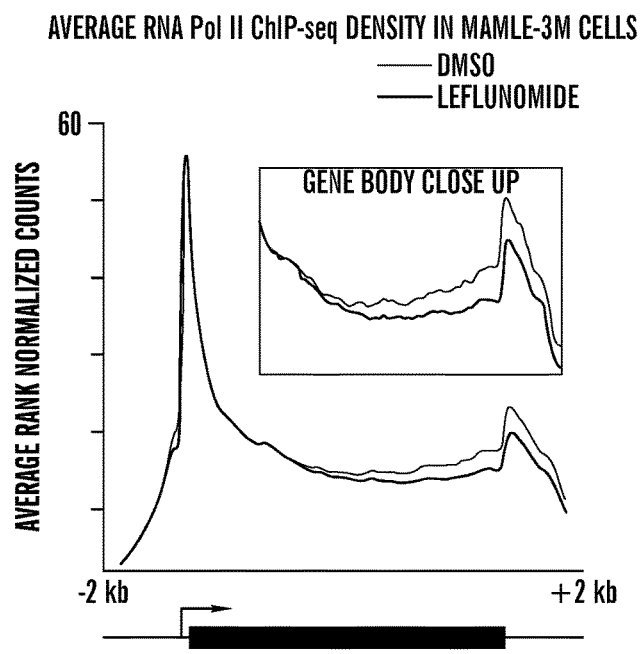
FIGS. 14a to 14b show metagene analysis graphs. ChIP-seq results in melanoma MAMLE-3M cells. Data are the same as that described in FIG. 3b,3c (A375 melanoma cells).
Figure 14B:
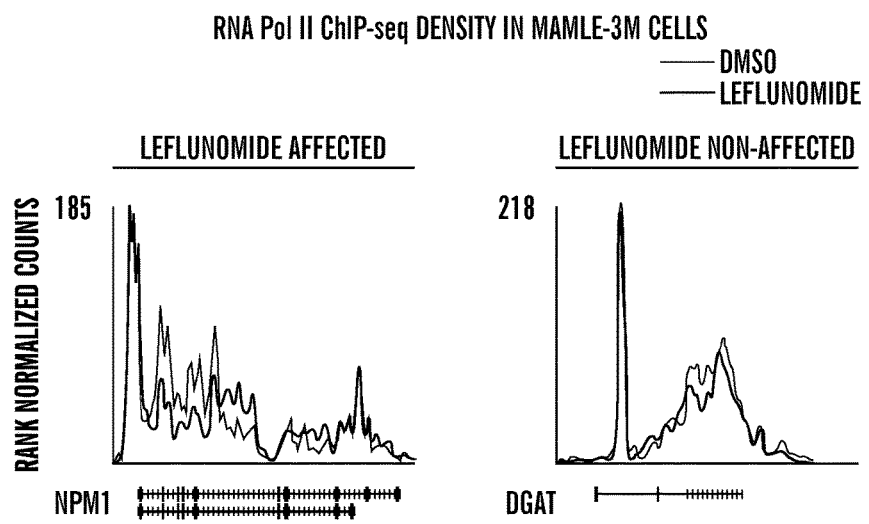

To confirm that this mechanism is conserved in human melanoma, we performed chromatin immunoprecipitation using an antibody to RNA polymerase II (Pol II), followed by sequencing (ChIP-seq). Transcriptional elongation was measured using the traveling ratio, TR[16], where the ratio of Pol II density in the promoter-proximal region is compared to the gene body. In both A375 and MAMLE-3M cells, leflunomide caused a significant inhibition of transcriptional elongation (measured as an increase in the TR), particularly for genes with an initially low TR<7.5. For example, in A375, the TR increased by >1.3 fold in 21.3% of loci; in MAMLE-3M, this was 36.3% of loci (data not shown). Examination of pol II occupancy using metagene analysis at a variety of fold-change cutoffs (FIG. 3b [A375], FIG. 14 [MAMLE-3M], and data not shown) revealed no defect in transcription initiation, but a decrease in elongation pronounced at the 3' end of genes such as Npm1 and Ccnd1 (FIG. 3c). Ingenuity Pathway Analysis on the loci affected in both cell lines revealed a strong enrichment for c-Myc targets and pathway members[17] (data not shown). c-Myc, in addition to its requirement in neural crest development,[18] was recently shown to be a potent regulator of transcriptional pause release in ES cells[16]. Our data suggests the regulation of c-Myc target genes at the transcriptional elongation level is an operative mechanism in neural crest-derived melanoma as well. Taken together, the genetic and biochemical data demonstrate that leflunomide acts to modulate transcriptional elongation in both neural crest development and human melanoma.

Figure 4A:
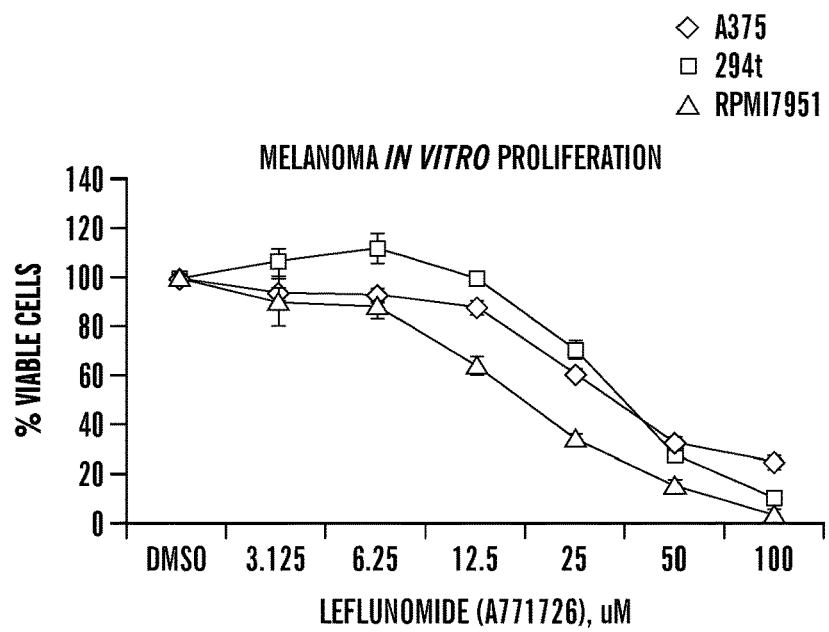
FIGS. 4a to 4c show graphs. DHODH blockade suppresses melanoma growth in concert with BRAF$^{V600E}$ inhibition.
Figure 4B:
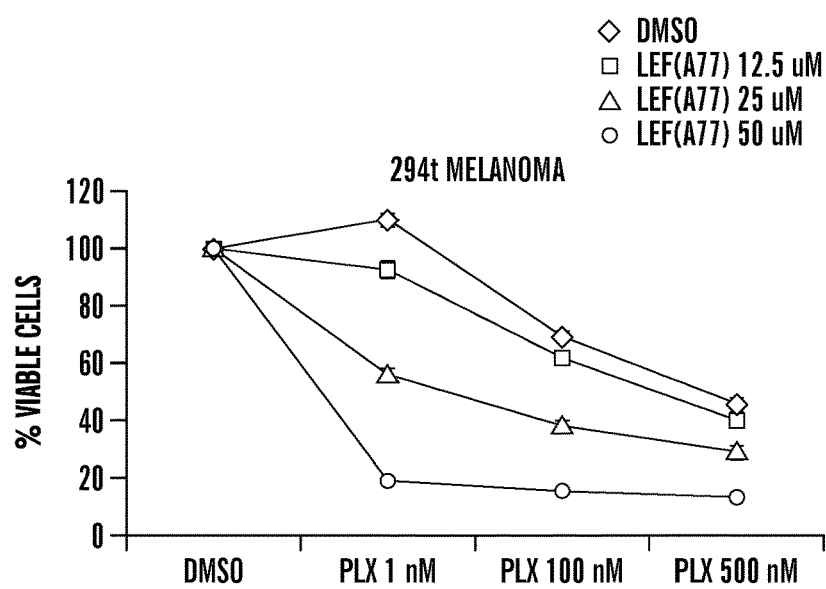
Figure 15A:
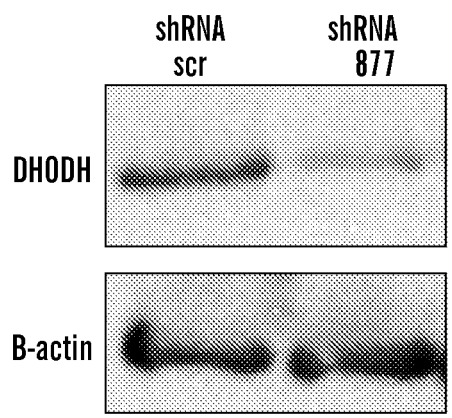
FIGS. 15a to 15c show a Western blot and graphs.
Figure 15B:
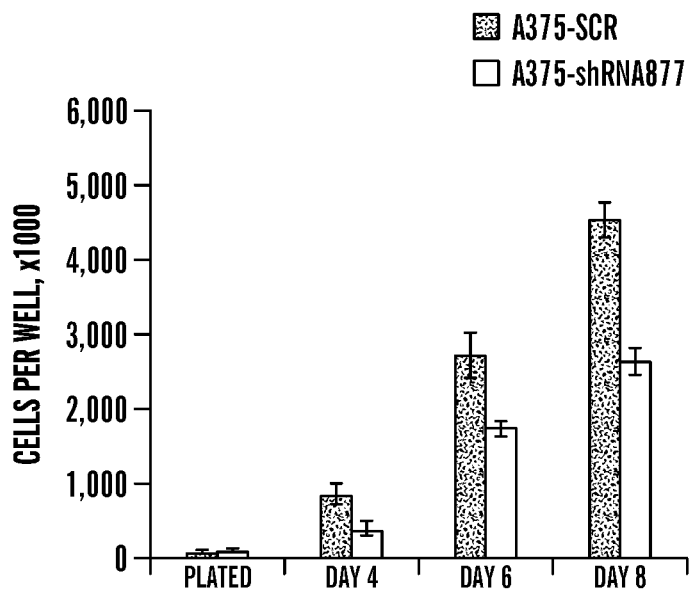
Figure 15C:
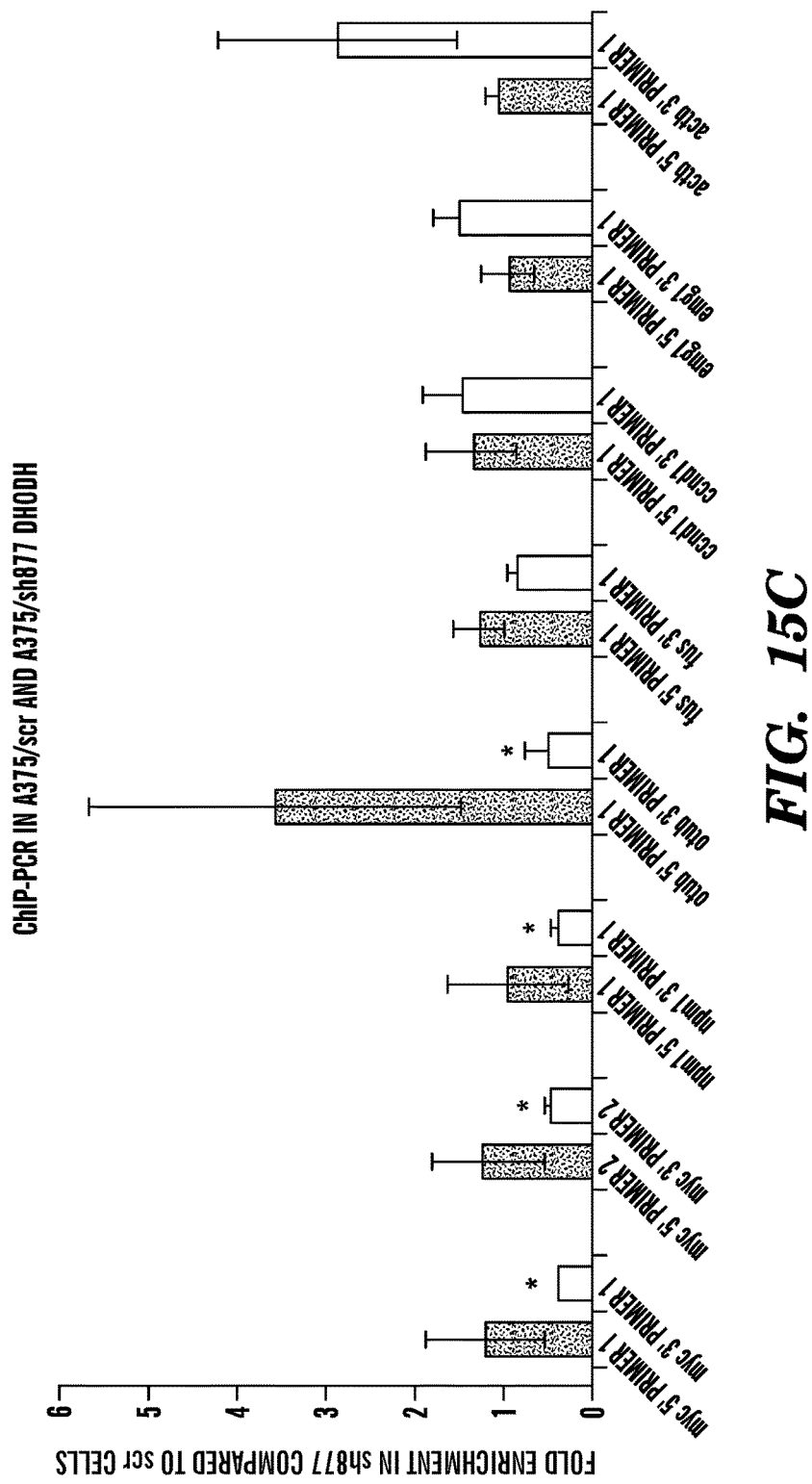

Given the effect of DHODH inhibition on neural crest development, we tested its effects on melanoma growth. A771726 caused a dose-dependent decrease in proliferation of human melanoma cell lines (A375, Hs.294t, RPMI7951; FIG. 4A). Similarly, an shRNA against DHODH led to a 57.7% decrease in proliferation of A375 cells, as well as a decrease in elongation as measured by ChIP-PCR (FIG. 15). Microarray analysis of the A375 cell line treated with leflunomide revealed downregulation of genes required for neural crest development (i.e. snai2) and members of the notch pathway (e.g. hes6, jag1), consistent with the effects in embryos (data not shown).

Figure 8A:
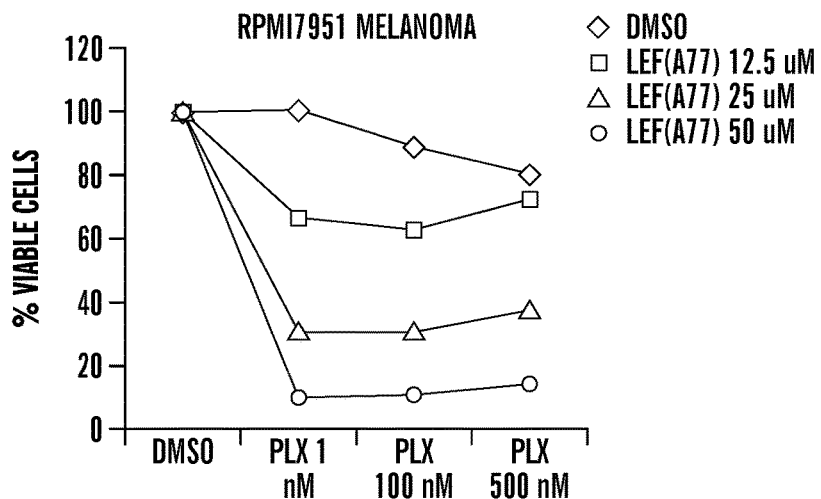
FIGS. 8a to 8d show graphs.
Figure 8B:
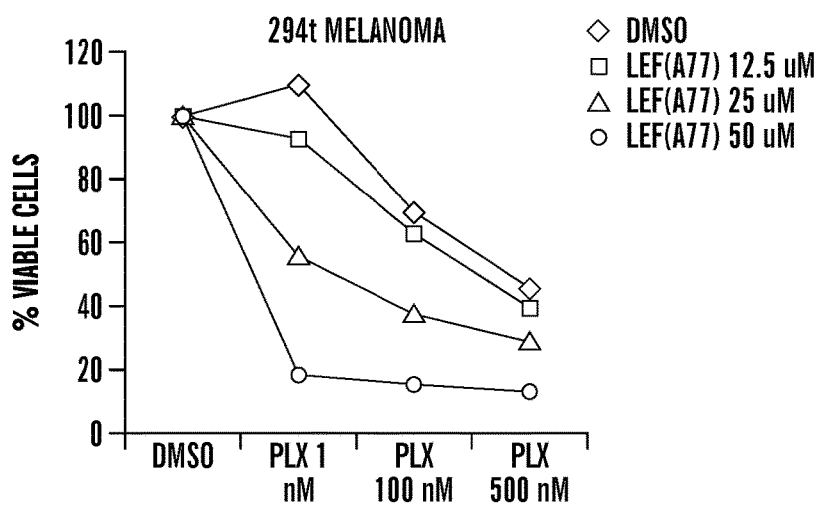
Figure 8C:
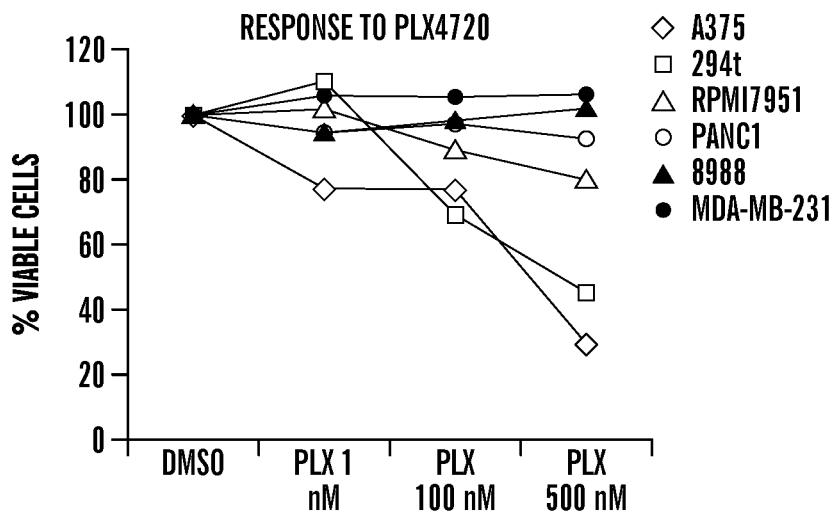
Figure 8D:
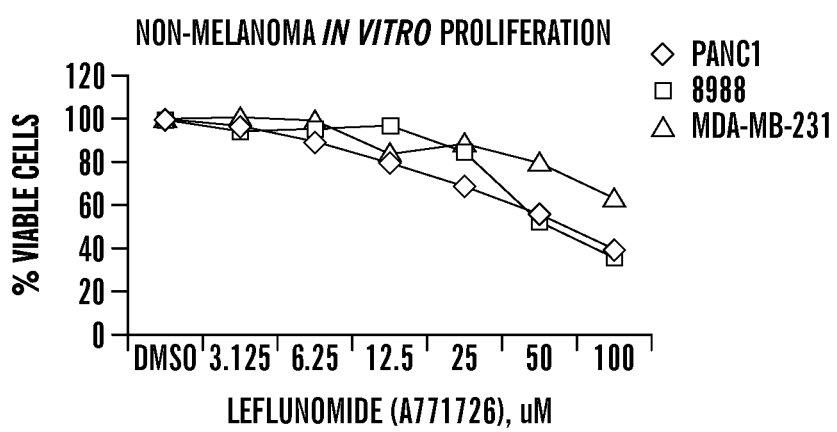

NTP production is regulated at the level of carbamoyl-phosphate synthetase (CAD)[19], the enzyme upstream of DHODH. CAD is phosphorylated by MAP kinase[20], which would be activated in melanoma due to the $BRAF^{V600E}$ mutation. We reasoned that combined blockade of $BRAF^{V600E}$ and DHODH would cooperate to suppress melanoma growth. We measured melanoma proliferation utilizing the $BRAF^{V600E}$ inhibitor PLX4720[21] together with A771726 (FIG. 4b, FIG. 4c and FIG. 8a, FIG. 8b), and found that the combination led to a cooperative suppression of melanoma growth. PLX4720 had no effect in non-melanoma cell lines ($BRAF^{WT}$, FIG. 8c). A771726 demonstrated mild antiproliferative activity but was less potent in these cells (FIG. 8d).

Figure 4C:
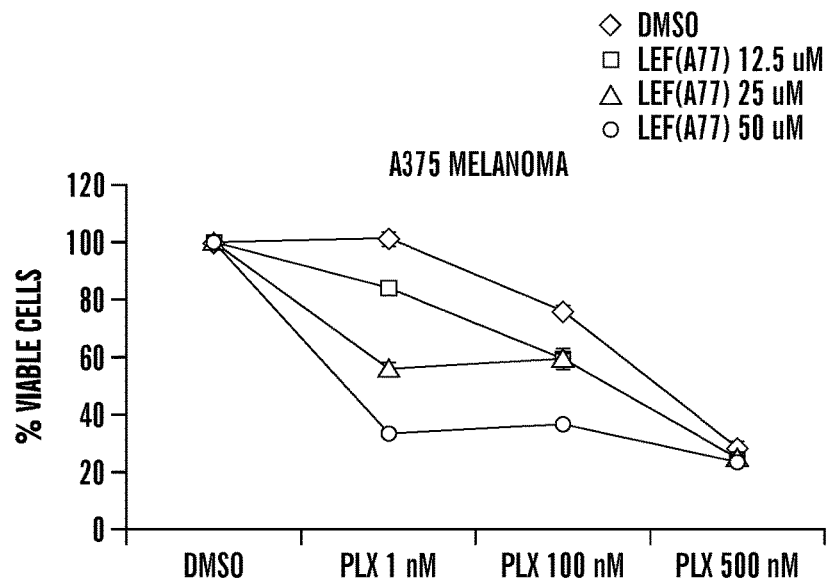
Figure 4D:
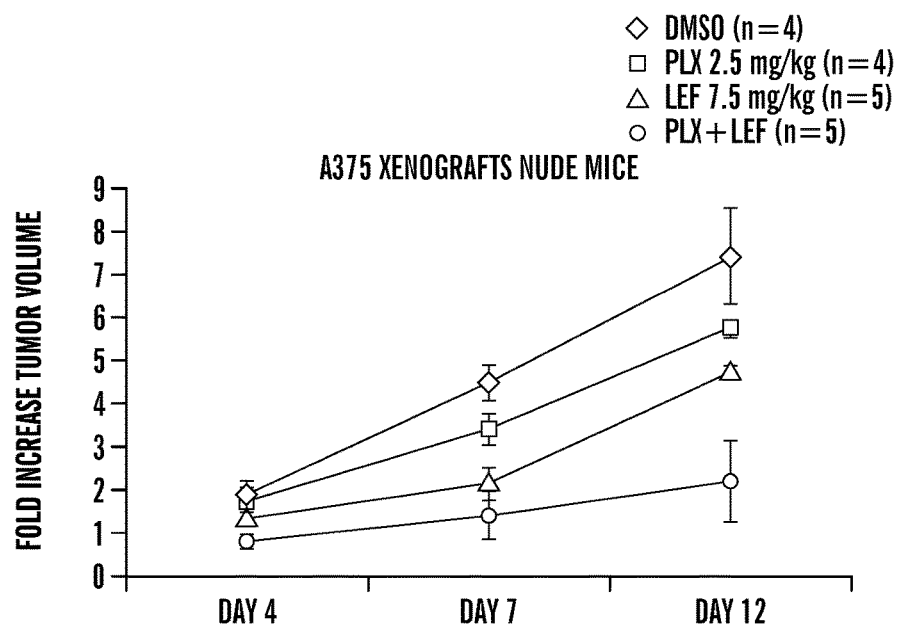
FIG. 4d, After subcutaneous transplantation of A375 cells (3×10$^5$) into nude mice, both leflunomide and PLX4720 impair tumor progression, with the combination showing a nearly complete abrogation of tumor growth and in 2/5 animals complete tumor regression. (*p=0.036 DMSO vs. PLX; p=0.006 DMSO vs. LEF; *p=0.006 PLX or LEF vs. PLX/LEF; PLX vs. LEF: p=NS, ANOVA followed by Tukey post-hoc analysis). Values shown are mean+/−SEM of n=3-5 replicates, as shown.
Figure 16:
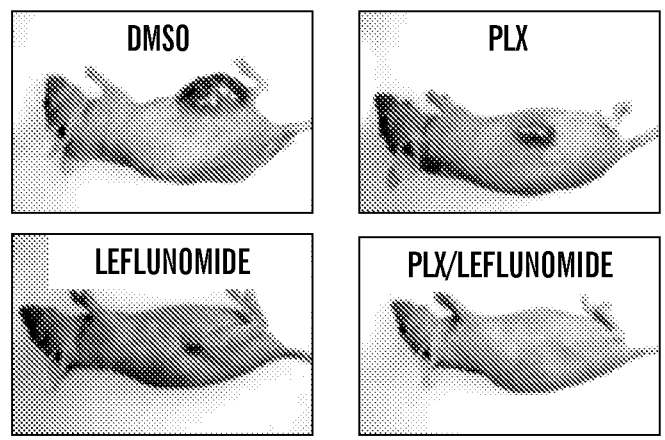
FIG. 16 show mice after treatment with inhibitors. Representative examples of mice after treatment with DMSO, PLX alone, leflunomide alone or the combination. See FIG. 4 for quantification.
Figure 17:
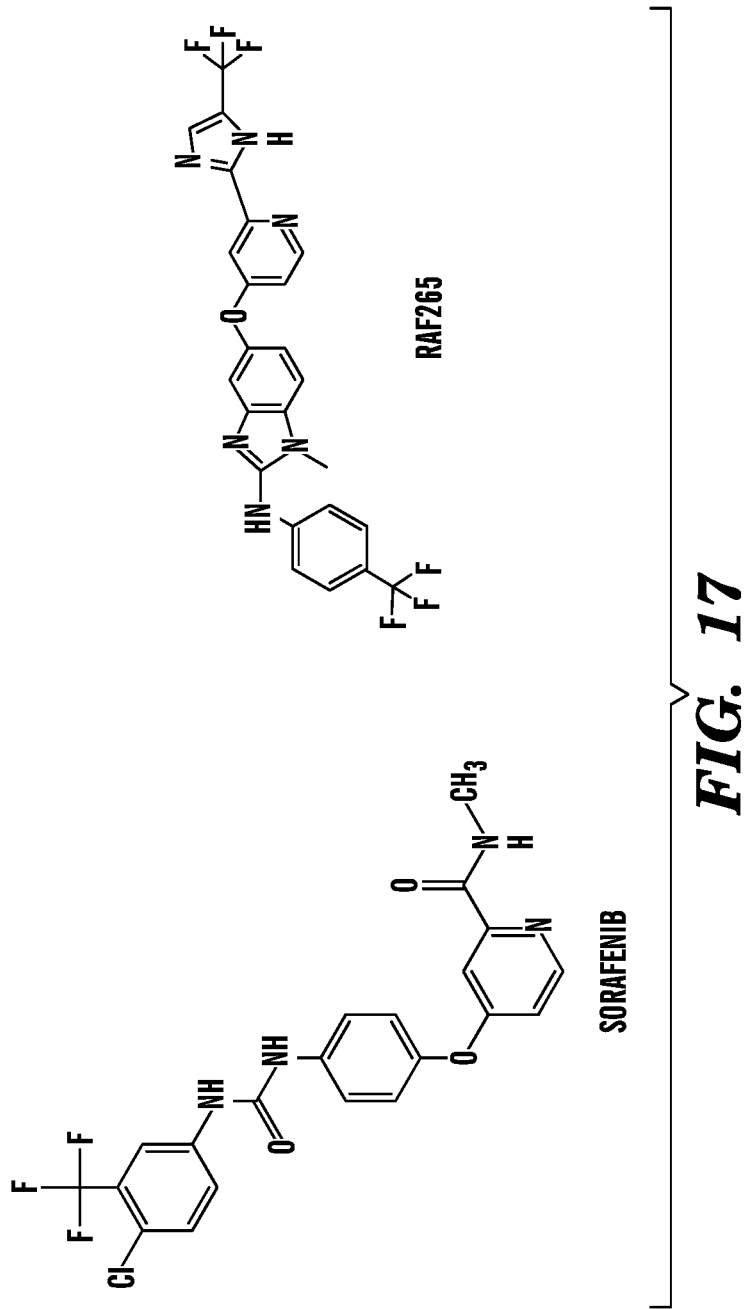
FIG. 17 shows the chemical structures of Sorafenib (Bayer) and RAF265.
Figure 18:
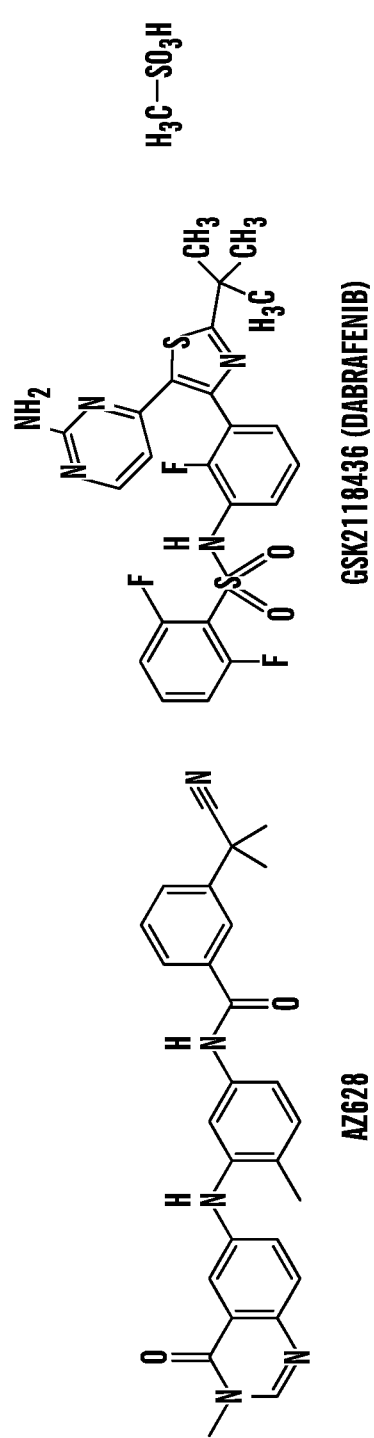
FIG. 18 shows the chemical structures of AZ628, and GSK2118463.
Figure 19:
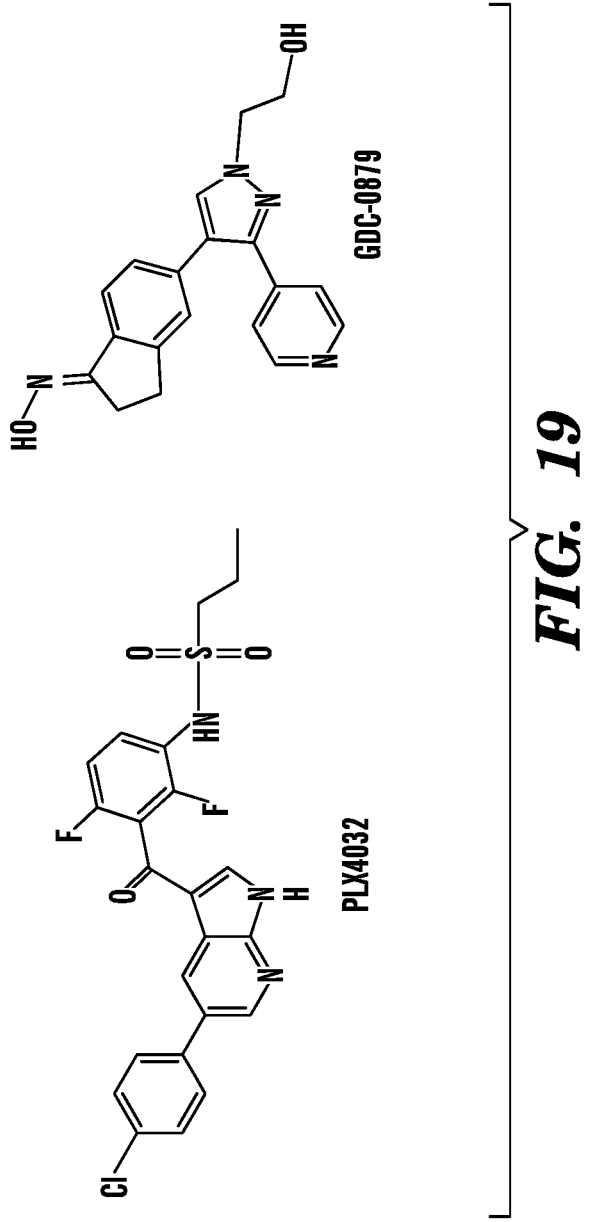
FIG. 19 shows the chemical structures of PLX4032 and GDC-0879.
Figure 20:
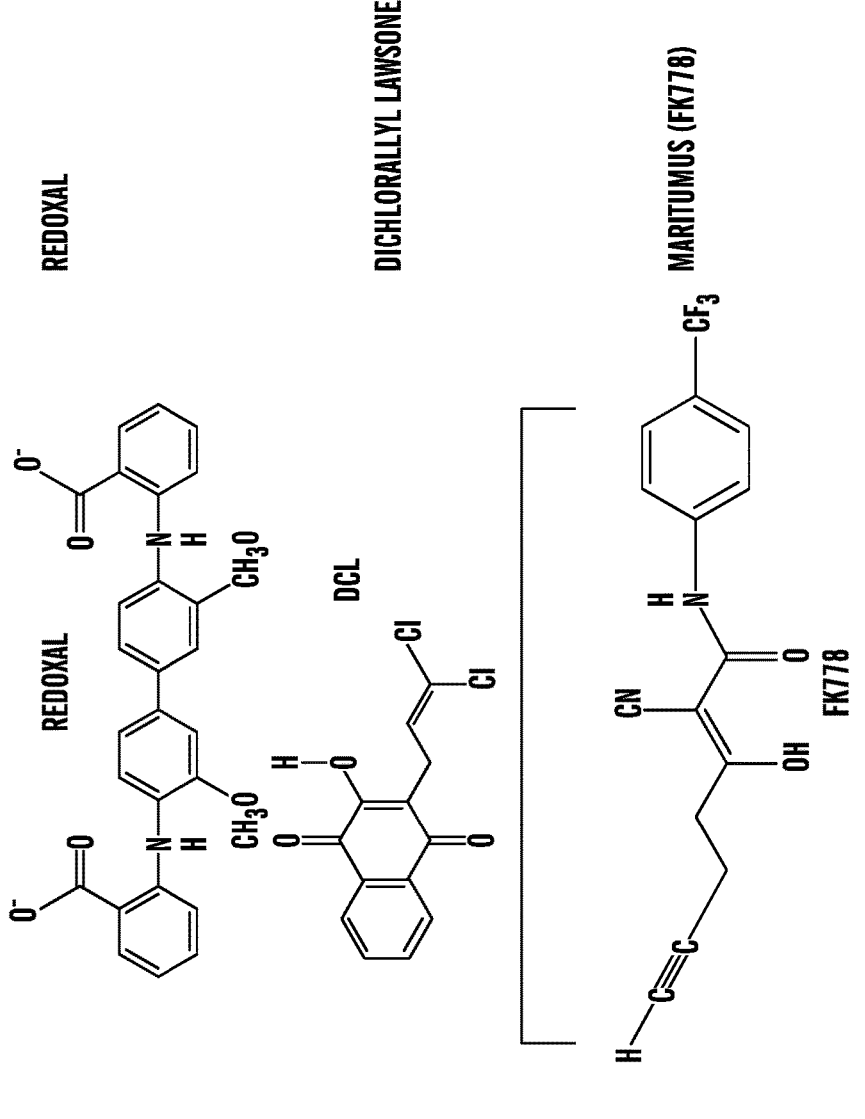
FIG. 20 shows the chemical structures of DHODH inhibitors dichloroallyl lawsone, maritumus (see U.S. Pat. No. 7,256,008), and redoxal.

We examined the in vivo effects of leflunomide and PLX4720 using xenografts of A375 melanoma cells transplanted into nude mice (FIG. 4c and FIG. 16). At 12 days post-treatment, DMSO tumors grew 7.4+/−1.3-fold, compared to 5.7+/−0.16-fold with PLX4720 and 4.7+/−0.12-fold with leflunomide. The combination of PLX4720 and leflunomide led to an enhanced abrogation of tumor growth, with only 2.2+/−0.9-fold growth, and in 40% of animals led to nearly complete tumor regression (p<0.001, PLX/LEF vs. PLX or LEF alone, ANOVA followed by Tukey's LSD). At clinically meaningful doses, we find that an inhibitor of embryonic neural crest development, leflunomide, blocks in vivo tumor growth in combination with the oncogenic $BRAF^{V600E}$ inhibitor PLX4720.

Our data suggest that inhibition of DHODH abrogates transcriptional elongation of genes required for both neural crest development and melanoma growth, including mitf and myc targets. Although DHODH inhibition would be expected to lead to ubiquitous defects, human mutations in DHODH cause Miller's syndrome[22], a craniofacial disorder similar to syndromes with defects in neural crest development. Our data support recent findings that elongation factors are important for both neural crest development[23] and cancer growth[24]. Developmental regulators of transcriptional elongation have recently been identified in hematopoiesis[25], and identification of such factors in the neural crest awaits further study.

Chemical genetic approaches in zebrafish and Xenopus allow for identification of molecules that require in vivo contexts for the expression of relevant phenotypes[26]. Inhibition of DHODH may provide a unique in vivo mechanism for modulating transcriptional elongation. Leflunomide is a well-tolerated arthritis drug in humans[27], and our data suggest it would be most effective incombination with a $BRAF^{V600E}$ inhibitor. This may help to overcome resistance to $BRAF^{V600E}$ inhibitors[28]. As an increasing number of genomic changes are identified in cancer, the challenge is to target these in concert with lineage-specific factors to uncover therapeutic synergy. Our approach to identifying lineage-specific suppressors in zebrafish embryos can be generalized to other cell types, with direct relevance to human cancer.

Methods Summary

Microarray analysis was performed on 4 groups of 72 hpf embryos: 1) WT, 2) mitf-$BRAF^{V600E}$, 3) $p53^{-/-}$ or 4) mitf-$BRAF^{V600E}$;$p53^{-/-}$ Arrays were similarly performed on adult mitf-$BRAF^{V600E}$;$p53^{-/-}$ melanomas and adjacent skin. The transcriptional signature of the melanomas was used in GSEA to identify genes significantly enriched in the mitf-$BRAF^{V600E}$;$p53^{-/-}$ embryos. This signature (123 genes), enriched for markers of the neural crest, were concordantly up/downregulated in both $BRAF^{V600E}$;$p53^{-/-}$ embryos and tumors. In situ hybridization (ISH) for crestin (a pan NC marker) and other NC genes, was examined in embryos (24-72 hpf) and adult tumors. Chemical screening was performed to identify suppressors of the crestin+ lineage by treating wild-type embryos from 50% epiboly to 24 hpf, followed by robotic ISH. Two inhibitors of DHODH abrogated crestin expression: NSC210627 and leflunomide. The latter was used for further studies due to more widespread availability. The effect of leflunomide on zebrafish embryonic neural crest development was assessed by scoring for embryonic melanocytes, iridophores, and glial cells. Leflunomide was further assessed for its ability to affect multipotent self-renewal of purified $p75^+\alpha_4^+$ rat neural crest stem cells. The effects of leflunomide on transcriptional elongation in the neural crest was tested using the $spt5^{m806}$ allele, and measuring pigmentation in response to 3-5 uM leflunomide. Elongation in melanoma cells was assayed by ChIP-Seq using an antibody to RNA Polymerase II and measuring the traveling ratio. Leflunomide was tested for anti-melanoma effects in human melanoma cells lines in the presence or absence of the $BRAF^{V600E}$ inhibitor PLX4720. In vitro proliferation assays were performed using the CellTiterGlo system (Promega). In vivo effects were tested by treatment of established A375 xenografts by daily intraperitoneal dosing of PLX4720 alone, leflunomide alone or the combination, and tumor growth rate measured on day 4, 7 and 12.

Generation of Zebrafish Lines

Wild-type strains used in these studies were the Tu variety. The $p53^{-/-}$ and transgenic mitf-$BRAF^{V600E}$ lines were established as previously described[29,30]. Double homozygous animals were genotyped using PCR primers for WT BRAF (Forward: TGCTCTTGACCTCAGACTGG (SEQ ID NO:6), Reverse: CCTCAATAAACAC-CCTACGG)(SEQ ID NO:7), BRAF V600E (Forward: GAGGCTTTGTCGAATCGGACCGGTG (SEQ ID NO:8), Reverse: TTGAACAGAGCCTGGCCCGGCT) (SEQ ID NO:9), and p53 (Forward: TGTGTCTGTCCATCTGTT-TAACAGTCA (SEQ ID NO:10), Reverse: GATAGC-CTAGTGCGAGCACACTCTT) (SEQ ID NO:11), The four genotypes used for the microarray analyses were produced by incrossing of each respective line.

RNA Preparation

Embryos: Fertilized eggs were collected immediately after mating, and placed at 28.5 C. Chorions were removed by pronase solution (2.5 mg/ml in E3 water), and embryos allowed to grow until either 24 hpf or 3 dpf. Clutches containing ~50 embryos were homogenized in Trizol, RNA precipitated with chloroform/isopropanol, DNaseI treated and the cleaned up using RNEasy columns. RNA was then utilized for Affymetrix Zebrafish Genome chips.

Adults: A single melanoma was dissected from the head, dorsum or tail of an adult $BRAF^{V600E};p53^{-/-}$ fish (~6 months of age). Extraneous tissue was removed. Simultaneously, the melanized skin directly adjacent to each given tumor was excised and acted as the comparator for that given fish. Tissues were prepared identically to the embryo RNA preparations.

Microarray Analysis $BRAF^{V600E};p53^{-/-}$ signature: To identify genes enriched between the $BRAF^{V600E};p53^{-/-}$ embryos and tumors, we initially identified genes that were at least 5-fold up or downregulated in the melanomas compared to the adjacent melanized skin. Significant genes were identified with Welch's T-test followed by Benjamini-Hochberg F D R at a q value <0.05. The top 200 up or down regulated genes were then used as the gene signature for GSEA (version 2), queried against the entire gene set (15,617 genes) for WT, p53, BRAF or $BRAF^{V600E};p53^{-/-}$ embryos. Genes that were significantly enriched in the $BRAF^{V600E};p53^{-/-}$ embryos compared to the other 3 strains were identified using weighting enrichment, the Signal2Noise ranking metric, and per-mutation=1000.

Leflunomide and spt5 signature: Tu embryos were treated with 6.5 uM leflunomide from 50% epiboly to 24 hpf, and then chorions removed and RNA extracted as above. Gene that were 2-fold up or downregulated by leflunomide were identified and then significance assessed by Welch's T-test followed by Benjamini-Hochberg FDR. This yielded 223 downregulated and 60 upregulated genes, which were then used in GSEA against a previously published spt5 (sk8) null mutant signature. Genes enriched between the leflunomide treatment and spt5 null mutants were identified using the same GSEA algorithm as above.

A375 signature: A375 cells were treated with 25 uM leflunomide for 3 days, and RNA then isolated using Trizol as above. Expression analysis was performed using Illumina WG6 v3 arrays, and the data was analyzed using Illumina Genome Studio. Genes significantly affected by leflunomide are those with an Illumina difference score of +/−30 or greater, which corresponds to a p value<0.001.

Chemical Screening Methodology

The screen was performed essentially as previously described[31]. In brief, WT embryos were collected, staged and then plated at a density of 10 embryos per well in a well-well tissue culture plate in 200 ul of E3 water. At 50% epiboly, 100 ul of a 3x chemical stock was added to each well using a Hamilton liquid handling robot, yielding a final 1x concentration. For the majority of the chemicals in the library, this yielded a concentration of ~33 uM. The libraries used were the BIOMOL 480, Sigma LOPAC 1280, and selected additional compounds obtained through the Children's Hospital Boston Chemical Screening facility. Compounds known to affect pigmentation in Xenopus were obtained from a screen previously described[32,33]. After treatment, embryos were rinsed in E3 water, pronase treated to remove chorions, washed 4x in E3 and 1x in PBT, and then fixed in 4% PFA for 24 hours. Fixed embryos were changed to 100% methanol 24 h later, and kept until the time of ISH.

Embryos underwent automated ISH using a Biolane HTI robot with a crestin riboprobe as previously described[31]. All wells were manually scored by eye, assigning a score within a range of 1 (no crestin staining) to 3 (no change in crestin) to 5 (marked increase in crestin). Note was also taken of chemicals that affected migratory patterns in both A-P and D-V directions, and overall morphology. Approximately 7% of chemicals were generally toxic, 2.2% showed a decrease in crestin, and 1% showed an increase in crestin. All hits were validated in larger, independent clutches of 100-200 embryos using chemicals obtained from independent suppliers.

In Vitro DHODH Assay

The DHODH activity assay monitored the reduction of 2,6-dichloroindophenol (DCIP) and was conducted in 50 μl of 100 mM HEPES (pH 8.0) containing 150 mM NaCl, 5% glycerol, 0.05% Triton X-100, 175 μM L-DHO, 18 μM decylubiquinone (CoQD), and 95 μM DCIP, arrayed in a 384-well format. The concentrations of enzymes used were as follows: P. falciparum 12.5 nM, human 7 nM. Following a 20 minute incubation at room temperature the absorbance was measured at 600 nm (Envision, PerkinElmer). A sigmoidal dose-response curve was generated by plotting % inhibition as a function of the log of compound concentration (range: 1.5 nM to 30 μM), and an IC50 value representing the concentration at which inhibition was half-maximal was determined.

Zebrafish Neural Crest Assay

For melanocyte assays, embryos were treated with leflunomide 5-6.5 uM from 50% epiboly until 48 hpf, at which point melanocytes along the dorsal axis and ventral pathways were assessed using visual scoring. The mitf-GFP transgenic was scored at 24 hpf, as this is the point of maximal GFP intensity. For the iridophore, mbp-mCherry and jaw cartilage experiments, the embryos were treated with 2.5 uM leflunomide to allow them to live beyond 48 hpf.

Rat Neural Crest Stem Cell Assays

Adherent Culture of NCSC

Enteric NCSCs from the fetal (E14.5) rat gut were isolated using flow cytometry to select the 1%-2% of cells expressing the highest levels p75 and α4 integrin as previously described[9]. Cells were plated at clonal density in two wells/treatment and cultured in self-renewal medium for 8 days in LEF, A771726 or the vehicle (DMSO) followed by differentiation medium+/−LEF, A771726 or DMSO for 6 days. Cultures were fixed in 4% PFA then stained with antibodies against peripherin, GFAP, and SMA to identify neurons (N), glia (G) and myofibroblasts (M) respectively (U=unstained cells). A total of 3 to 4 independent experiments were performed, and differences measured by ANOVA followed by Bonferonni posthoc comparison. Self-renewal medium contains: DMEM-low glucose, 15% Chick Embryo Extract (CEE), Penn/Strep (P/S), 1% N2 supplement, 2% B27 supplement, 110 nM Retinoic Acid, 50 μM 2-mercaptoethanol 20 ng/ml bFGF, and 20 ng/ml IGF-1. Differentiation medium is the same except it contains 1% CEE, 10 ng/ml bFGF and no IGF-1. Differences between groups were calculated using ANOVA followed by posthoc Sheffe.

Non-Adherent Culture of NCSC

Dissociated fetal rat gut cells were plated at clonal density in non-adherent conditions in self-renewal medium with LEF, a77 or DMSO for 10 days[10]. Three to five primary neurospheres per treatment were individually re-plated in adherent conditions with LEF, a77 or DMSO and after three days were dissociated into a single cell suspension using trypsin and collagenase IV. Dissociated cells from each neurosphere were re-plated in non-adherent conditions without LEF or a77 and after 10 days, the number of secondary neurospheres were counted and compared. To assess the number of multipotent primary and secondary neurospheres, a subset of neurospheres were plated adherently for 8 days in self-renewal medium followed by 6 days in differentiation medium. Cultures were fixed in 4% PFA and stained with antibodies against peripherin, GFAP, and SMA to identify neurons (N), glia (G) and myofibroblasts (M) respectively. A total of 5 independent experiments were analyzed, and the number of multipotent secondary neurospheres on a given day are normalized to the DMSO control wells, and differences calculated by ANOVA.

spt5 Hypomorphic Experiments

The $spt5^{m806}$ allele was used to assess whether leflunomide interacted with the elongation machinery. This allele has only a mild pigment defect on its own. Heterozygous $spt5^{m806}$ adults were incrossed, and embryos then collected and treated with leflunomide 3, 4 or 5 uM, as above. Embryos were scored at 48 hpf for pigmentation, scored as "unpigmented", "light", or "fully pigmented" as compared to untreated wells. Individual embryos were then genotyped for the $spt5^{m806}$ mutation as previously described[14]. Kruskall-Wallis analysis was used to detect a difference between the genotyped groups.

5'-3' Transcriptional Elongation Assays

Embryos were treated with DMSO or leflunomide 6.5 uM from 50% epiboly until 24 hpf, and then RNA prepared as above. Primers were designed to the noted genes, situated at the very 5' end or 3' end of the gene, situated in the UTR if annotated. qRT-PCR was then performed using SYBR Green, and each primer pair was normalized to an average of the Ct value for the 5' beta-actin and 3' beta-actin primers. Fold-change was calculated using the delta-delta Ct method, and all values are expressed relative to the DMSO control, after log 2 transformation. Differences between groups were assessed using t-tests. Primer sequences available upon request.

RNA Pol II ChIP-Seq Analysis Following Leflunomide Treatment

Chromatin Immunoprecipitation

RNA Pol II ChIP-seq analysis was done in A375 and MAMLE-3M cells with and without Leflunomide treatment as described in[16]. In brief, A375 and MAMLE-3M cells were grown as described above and treated with 25 uM (A375) or 50 uM (MAMLE-3M) leflunomide (dissolved in DMSO) or DMSO alone for 72 hours. Cells were cross-linked for 10 minutes with the addition of one-tenth of the volume of 11% formaldehyde solution (11% formaldehyde, 50 mM Hepes pH7.3, 100 mM NaCl, 1 mM EDTA pH8.0, 0.5 mM EGTA pH8.0) to the growth media followed by two washes with PBS. Cells were scraped and frozen in liquid nitrogen. 100 ul of Dynal magnetic beads (Sigma) were blocked with 0.5% BSA (w/v) in PBS. Magnetic beads were bound with 10 ug of total Pol II antibody (Rpb1 N-terminus, Santa Cruz sc-899). Unbound antibody was washed away following an overnight incubation at 4° C. Crosslinked cells were lysed with lysis buffer 1 (50 mM Hepes pH7.3, 140 mM NaCl, 1 mM EDTA, 10% glycerol, 0.5% NP-40, and 0.25% Triton X-100) and washed with lysis buffer 2 (10 mM Tris-HCl pH8.0, 200 mM NaCl, 1 mM EDTA pH8.0 and 0.5 mM EGTA pH8.0). Cells were resuspended and sonicated in sonication buffer (50 mM Tris-HCl pH7.5, 140 mM NaCl, 1 mM EDTA, 1 mM EGTA, 1% Triton X-100, 0.1% Na-deoxycholate, 0.1% SDS) for 8 cycles at 30 seconds each on ice (18 watts) with 60 seconds on ice between cycles. Sonicated lysates were cleared and incubated overnight at 4° C. with magnetic beads bound with antibody to enrich for DNA fragments bound by the indicated factor. Beads were washed three times with sonication buffer, one time with sonication buffer with 500 mM NaCl, one time with LiCl wash buffer (20 mM Tris pH8.0, 1 mM EDTA, 250 mM LiCl, 0.5% NP-40, 0.5% Na-deoxycholate) and one time with TE. DNA was eluted in elution buffer. Cross-links were reversed overnight. RNA and protein were digested using RNAse A and Proteinase K, respectively and DNA was purified with phenol chloroform extraction and ethanol precipitation. The purified DNA from A375+Leflunomide, A375+DMSO, A375 input DNA, Mamle+Leflunomide, Mamle+DMSO and Mamle input DNA samples were then used for preparation of Illumina sequencing libraries.

Sample Preparation

Purified DNA was prepared for sequencing according to a modified version of the Illumina/Solexa Genomic DNA protocol. Fragmented DNA was prepared by repairing the ends and adding a single adenine nucleotide overhang to allow for directional ligation. A 1:30 dilution (in water) of the Adaptor Oligo Mix (Illumina) was used in the ligation step. A subsequent PCR step with limited (18) amplification cycles added additional linker sequence to the fragments to prepare them for annealing to the Genome Analyzer flow-cell. The amplified library was size selected by separation on a 2% agarose gel and a band between 150-300 bp (representing shear fragments between 50 and 200 nt in length and ~100 bp of primer sequence) was excised. The DNA was purified from the agarose and this DNA library was subsequently used for polony generation and sequencing.

Polony Generation and Sequencing

The DNA library (2-4 pM) was applied to the flow-cell (8 samples per flow-cell) using the Cluster Station device from Illumina. The concentration of library applied to the flow-cell was calibrated such that polonies generated in the bridge amplification step originate from single strands of DNA. Multiple rounds of amplification reagents were flowed across the cell in the bridge amplification step to generate polonies of approximately 1,000 strands in 1 μm diameter spots. Double stranded polonies were visually checked for density and morphology by staining with a 1:5000 dilution of SYBR Green I (Invitrogen) and visualizing with a microscope under fluorescent illumination. Validated flow-cells were stored at 4° C. until sequencing.

Flow-cells were removed from storage and subjected to linearization and annealing of sequencing primer on the Cluster Station. Primed flow-cells were loaded into the Illumina Genome Analyzer 1G. After the first base was incorporated in the Sequencing-by-Synthesis reaction the process was paused for a key quality control checkpoint. A small section of each lane was imaged and the average intensity value for all four bases was compared to minimum thresholds. Flow-cells with low first base intensities were re-primed and if signal was not recovered the flow-cell was aborted. Flow-cells with signal intensities meeting the minimum thresholds were resumed and sequenced for 26 or 32 cycles.

Solexa Data Analysis

Images acquired from the Illumina/Solexa sequencer were processed through the bundled Solexa image extraction pipeline, which identified polony positions, performed base-calling and generated QC statistics. Sequences were aligned using ELAND software to NCBI Build 36 (UCSC hg18) of the human genome. Only sequences that mapped uniquely to the genome with zero or one mismatch were used for further analysis. When multiple reads mapped to the same genomic position, a maximum of two reads mapping to the same position were used. Analysis methods were derived from previously published methods[34-37]. Each read was extended 100 bp, towards the interior of the sequenced fragment, based on the strand of the alignment. The number of ChIP-Seq reads across the genome, in 25 bp bins within a 1 kb window surrounding each bin (+/−500 bp) was tabulated. The 25 bp genomic bins that contained statistically significant ChIP-Seq enrichment was identified by comparison to a Poissonian background model. Assuming background reads are spread randomly throughout the genome, the probability of observing a given number of reads in a 1 kb window can be modeled as a Poisson process in which the expectation can be estimated as the number of mapped reads multiplied by the number of bins (40) into which each read maps, divided by the total number of bins available (estimated at 70%). Enriched bins within 1 kb of one another were combined into regions.

The Poissonian background model assumes a random distribution of background reads, however we have observed deviations from this expectation. Some of these non-random events can be detected as sites of apparent enrichment in negative control DNA samples and can create many false positives in ChIP-Seq experiments. To remove these regions when determining enriched regions, we compared genomic bins and regions that meet the statistical threshold for enrichment to a set of reads obtained from Solexa sequencing of DNA from whole cell extract (WCE) in matched cell samples. We required that enriched bins and enriched regions have five-fold greater ChIP-Seq density in the specific IP sample, compared with the control sample, normalized to the total number of reads in each dataset. This served to filter out genomic regions that are biased to having a greater than expected background density of ChIP-Seq reads. For comparison of Pol II occupancy following Leflunomide treatment with a control dataset, rank normalization was used to normalize the datasets being compared. This normalization method is described in[38]. Briefly, a quantile normalization method was used for analysis. For each dataset compared, the genomic bin with the greatest ChIP-Seq density was identified. The average of these values was calculated and the highest signal bin in each dataset was assigned this average value. This was repeated for all genomic bins from the greatest signal to the least, assigning each the average ChIP-Seq signal for all bins of that rank across all datasets.

Traveling Ratio Calculation

Traveling ratios (TR) were calculated as described in[16]. Briefly, TR compares the ratio between Pol II density in the promoter and in the gene body region. The promoter region is defined as −300 bp to +300 bp relative to the TSS and the gene body is defined as the remaining length of the gene plus 2500 bp relative to the gene end. We chose to use the gene body plus the 2.5 kb after the gene end in our TR calculations because we have noticed both here and in Rahl et al, that changes in elongating Pol II density are most pronounced just after the end of the gene, presumably in the transcription termination region.

Meta Gene Analysis

In order to quantify the effects of Leflunomide treatment on the promoter and gene body regions, we first created density vectors for all genes. The densities in the promoter, gene body, and gene end region were placed into 360 bins to create a density vector. 80 fixed width bins for the −2000 to 0 promoter region, 200 variable bins equally dividing the length of the gene, and 80 fixed bins for the 0 to +2 kb after transcript end region. For each gene, the promoter density vector was defined as the density in the 12 bins upstream of the TSS plus the density in the 6 variable length bins downstream. The gene body density vector was defined as the density in the last 160 variable length bins comprising the gene plus the 80 fixed width bins after the gene end.

To quantify the effects of Leflunomide treatment, the matrix of density vectors for a given gene set in either DMSO or Leflunomide treated cells was compared using a Welch's t-test. This was performed for genes with TR changes at various fold-change cut offs in both A375 and MAMLE cells, with comparison of pol II in the promoter or gene body of loci at each fold change cutoff.

The method used here is a variation of the analysis used in Rahl et al, and is more sensitive due to the fact that gene densities are treated as vectors rather than mean values.

Prediction of c-Myc Target Gene Enrichment in ChIP-Seq Data

The genes most inhibited in elongation were entered into Ingenuity Pathway Analysis (IPA) software as per manufacturer's instructions. Pathway analysis, which included the myc module, was performed as part of standard IPA analysis. For identification of c-myc target genes contained within Supplemental Table 4, we utilized the data found in[17].

ChIP-PCR

ChIP for RNA polymerase II was carried out as above using A375-scramble and A375-shRNA#877 cells. For the shRNA against DHODH, we utilized TRNC clone TRCN0000025839 (sequence: CCGGCGATGGGCTGATT-GTTACGAACTCGAGTTCGTAACAATCAGC-CCATCGTTTTT (SE ID NO:12). A375 cells were infected with 200 ul of viral supernatant in 2 ml of media with protamine, and cells selected with puromycin. Cells were grown to 60% confluency and crosslinked and harvested with formaldehyde. ChIP DNA was obtained for both IgG control as well as pol II (Santa Cruz sc-899). PCR primers were designed based on the peaks seen in ChIP-Seq data from the DMSO and leflunomide assays. qPCR using SYBR GreenER (Invitrogen) was performed for 50 cycles with an extension/read time of 60 seconds at 60 C. The fold enrichment for the sh877 compared to scramble cells was calculated as $2^{\wedge}[(C_tPol2-C_tIgG)_{scramble}-(C_tPol2-C_tIgG)_{sh877}]$.

In Vitro Melanoma Proliferation Assays

Human melanoma cell lines (A375, RPMI7951, Hs.294T, MAMLE-3M) were obtained from the American Type Culture Collection. The 8988 cell line was provided by Alec Kimmelman at Dana Farber, and the PANC1 and MDA-231-MB lines were provided by Rania Hartouche at Harvard. Cells were cultured in DMEM/10% FCS at 37 C, 5% $CO_2$. For proliferation assays, 96-well clear bottom plates were used to plate cells at a density of 5,000 cells/well (RPMI7951 and A375) or 10,000 cells/well (MAMLE-3M-3M and Hs.294T) in 100 ul containing indicated concentrations of A771726 or PLX4720 or DMSO. All conditions were tested in triplicate. Media was changed at day 2, and proliferation rate was measured at day 4 using the CellTiterGlo assay kit (Promega). All values are expressed are the % of luciferase relative to the DMSO control well. Differences between groups were statistically analyzed using a generalized linear ANOVA model taking into account factors of PLX4720, A771726 and dose. IC50's were calculated using a log-logistic model.

For proliferation assays in the A375-scramble and A375-sh877 cells, 50,000 cells were plated on day 0 and grown for the indicated time in puromycin containing media. Cells were harvested (in triplicate) and counted with a hemocytometer on days 4, 6 and 8.

In Vivo Xenograft Studies

The A375 cell line was chosen for xenografts based on prior experience with PLX4720 in this line. Cells were grown to 60-70% confluence, trypsinized and $3.5 \times 10^5$ cells were transplanted into the right flank of nude mice in a volume of 200 ul. Tumors were allowed to develop for 2 weeks (day 0) at which time daily intraperitoneal dosing of either DMSO, PLX4720 2.5 mg/kg, Leflunomide 7.5 mg/kg or both PLX4720/Leflunomide was begun. Tumors were measured with digital calipers on day 4, 7 and 12 and growth rate was compared to the tumor size on day 0. Growth rates were compared between DMSO, PLX, LEF or PLX4720 using ANOVA with repeated measures to identify significant interactions. For the day 12 data, differences between the groups were compared using ANOVA followed by posthoc Tukey's least-squared difference.

Human Tissue Array

Human melanoma array ME 1001 (US Biomax) was stained using antibodies to ednrb (Abcam ab1921), edn3 (PTG Inc. 10674-1-AP), mitf (Abcam 3201) or dct (Sigma HPA010743). Melanomas were scored by an independent pathologist (SG) for reactivity to given antibody. In some cases, tumors stained for multiple antibodies in different areas of the same tumor, and these were scored as positive for each individual antigen.

All the references cited below and cited throughout the specification, are herein incorporated by reference in their entirety.

EXAMPLE REFERENCES

1. Davies, H. et al. Mutations of the BRAF gene in human cancer. *Nature* 417, 949-954 (2002).
2. Rubinstein, A. L., Lee, D., Luo, R., Henion, P. D. & Halpern, M. E. Genes dependent on zebrafish cyclops function identified by AFLP differential gene expression screen. *Genesis*. 26, 86-97 (2000).
3. Luo, R., An, M., Arduini, B. L. & Henion, P. D. Specific pan-neural crest expression of zebrafish Crestin throughout embryonic development. *Dev. Dyn.* 220, 169-174 (2001).
4. Bakos, R. M. et al. Nestin and SOX9 and SOX10 transcription factors are coexpressed in melanoma. *Exp. Dermatol.* 19, e89-94 (2010).
5. Boiko, A. D. et al. Human melanoma-initiating cells express neural crest nerve growth factor receptor CD271. *Nature* 466, 133-137 (2010).
6.
7. McLean, J. E., Neidhardt, E. A., Grossman, T. H. & Hedstrom, L. Multiple inhibitor analysis of the brequinar and leflunomide binding sites on human dihydroorotate dehydrogenase. *Biochemistry* 40, 2194-2200 (2001).
8. Kaplan, M. J. Leflunomide Aventis Pharma. *Curr. Opin. Investig Drugs* 2, 222-230 (2001).
9. Bixby, S., Kruger, G. M., Mosher, J. T., Joseph, N. M. & Morrison, S. J. Cell-intrinsic differences between stem cells from different regions of the peripheral nervous system regulate the generation of neural diversity. *Neuron* 35, 643-656 (2002).
10. Molofsky, A. V. et al. Bmi-1 dependence distinguishes neural stem cell self-renewal from progenitor proliferation. *Nature* 425, 962-967 (2003).
11. Loffler, M., Jockel, J., Schuster, G. & Becker, C. Dihydroorotat-ubiquinone oxidoreductase links mitochondria in the biosynthesis of pyrimidine nucleotides. *Mol. Cell. Biochem.* 174, 125-129 (1997).
12. Keegan, B. R. et al. The elongation factors Pandora/Spt6 and Foggy/Spt5 promote transcription in the zebrafish embryo. *Development* 129, 1623-1632 (2002).
13. Krishnan, K., Salomonis, N. & Guo, S. Identification of Spt5 target genes in zebrafish development reveals its dual activity in vivo. *PLoS One* 3, e3621 (2008).
14. Guo, S. et al. A regulator of transcriptional elongation controls vertebrate neuronal development. *Nature* 408, 366-369 (2000).
15. Wada, T. et al. DSIF, a novel transcription elongation factor that regulates RNA polymerase II processivity, is composed of human Spt4 and Spt5 homologs. *Genes Dev.* 12, 343-356 (1998).
16. Rahl, P. B. et al. c-Myc regulates transcriptional pause release. *Cell* 141, 432-445 (2010).
17. Chen, Y. et al. Integration of genome and chromatin structure with gene expression profiles to predict c-MYC recognition site binding and function. *PLoS Comput. Biol.* 3, e63 (2007).
18. Hong, S. K., Tsang, M. & Dawid, I. B. The mych gene is required for neural crest survival during zebrafish development. *PLoS One* 3, e2029 (2008).
19. Aoki, T., Morris, H. P. & Weber, G. Regulatory properties and behavior of activity of carbamoyl phosphate synthetase II (glutamine-hydrolyzing) in normal and proliferating tissues. *J. Biol. Chem.* 257, 432-438 (1982).
20. Graves, L. M. et al. Regulation of carbamoyl phosphate synthetase by MAP kinase. *Nature* 403, 328-332 (2000).
21. Tsai, J. et al. Discovery of a selective inhibitor of oncogenic B-Raf kinase with potent antimelanoma activity. *Proc. Natl. Acad. Sci. U.S.A.* 105, 3041-3046 (2008).
22. Ng, S. B. et al. Exome sequencing identifies the cause of a mendelian disorder. *Nat. Genet.* 42, 30-35 (2010).
23. Nguyen, C. T., Langenbacher, A., Hsieh, M. & Chen, J. N. The PAF1 complex component Leo1 is essential for cardiac and neural crest development in zebrafish. *Dev. Biol.* 341, 167-175 (2010).
24. Mueller, D. et al. Misguided transcriptional elongation causes mixed lineage leukemia. *PLoS Biol.* 7, e1000249 (2009).
25. Bai, X. et al. TIF1 gamma controls erythroid cell fate by regulating transcription elongation. *Cell* 142, 133-143 (2010).
26. Wheeler, G. N. & Brandli, A. W. Simple vertebrate models for chemical genetics and drug discovery screens: lessons from zebrafish and *Xenopus*. *Dev. Dyn.* 238, 1287-1308 (2009).
27. Schiff, M. H., Strand, V., Oed, C. & Loew-Friedrich, I. Leflunomide: efficacy and safety in clinical trials for the treatment of rheumatoid arthritis. *Drugs Today (Barc)* 36, 383-394 (2000).
28. Flaherty, K. T. et al. Inhibition of mutated, activated BRAF in metastatic melanoma. *N. Engl. J. Med.* 363, 809-819 (2010).
29. Berghmans, S. et al. Tp53 Mutant Zebrafish Develop Malignant Peripheral Nerve Sheath Tumors. *Proc. Natl. Acad. Sci. U.S.A.* 102, 407-412 (2005).
30. Patton, E. E. et al. BRAF mutations are sufficient to promote nevi formation and cooperate with p53 in the genesis of melanoma. *Curr Biol* 15, 249-54 (2005).

31. Kaufman, C. K., White, R. M. & Zon, L. Chemical genetic screening in the zebrafish embryo. *Nat. Protoc.* 4, 1422-1432 (2009).
32. Tomlinson, M. L., Rejzek, M., Fidock, M., Field, R. A. & Wheeler, G. N. Chemical genomics identifies compounds affecting *Xenopus laevis* pigment cell development. *Mol. Biosyst* 5, 376-384 (2009).
33. Tomlinson, M. L. et al. A chemical genomic approach identifies matrix metalloproteinases as playing an essential and specific role in *Xenopus* melanophore migration. *Chem. Biol.* 16, 93-104 (2009).
34. Mikkelsen, T. S. et al. Genome-wide maps of chromatin state in pluripotent and lineage-committed cells. *Nature* 448, 553-560 (2007).
35. Johnson, D. S., Mortazavi, A., Myers, R. M. & Wold, B. Genome-wide mapping of in vivo protein-DNA interactions. *Science* 316, 1497-1502 (2007).
36. Marson, A. et al. Connecting microRNA genes to the core transcriptional regulatory circuitry of embryonic stem cells. *Cell* 134, 521-533 (2008).
37. Guenther, M. G. et al. Aberrant chromatin at genes encoding stem cell regulators in human mixed-lineage leukemia. *Genes Dev.* 22, 3403-3408 (2008).
38. Bilodeau, S., Kagey, M. H., Frampton, G. M., Rahl, P. B. & Young, R. A. SetDB1 contributes to repression of genes encoding developmental regulators and maintenance of ES cell state. *Genes Dev.* 23, 2484-2489 (2009).

Example II

Example guidance for a Phase II trial to test the efficacy of a combination therapy of the combination therapy of BRAF inhibitor PLX4032 and leflunomide.

We have found Leflunomide to block neural crest cell fate by inhibiting transcriptional elongation, wherein a reduced number of neural crest progenitors leading to a decrease in the number of differentiated melanocyte cells unexpectedly indicated that the compound is capable of inhibiting melanoma. The targets of these events include c-myc and mitf (FIG. 9, FIG. 13) directed genes. Prior to this finding, it was not obvious and was unexpected that Leflunomide could be utilized in therapies to treat melanoma given its previous use as an anti-arthritic agent predicated on its ability to target lymphocytes (See e.g., Fox et al., (1999) Mechanism of Action for Leflunomide in Rhuematoid Arthritis, *Clinical immunology* 93(3): 198-208). Non-lymphocytes were previously believed to be unaffected because of their ability to meet their ribonucleotide needs utilizing the salvage pyrimidine pathway. Melanoma is a non-lymphocyte derived cancer characterized by uncontrolled growth of melanocytes. Thus, the combination of the Leflunomide, which attacks melanoma cell fate, coupled to BRAF-inhibitor that targets cell proliferation is a novel and non-obvious combination aimed to treat melanoma. Furthermore, the fact that only subclinical dosing are required points to unexpected synergy, which renders this invention both a more effective and safer therapy than current approaches.

To undertake a phase II trial testing the efficacy of the neural crest stem cell inhibitor leflunomide will be used in combination with the BRAF inhibitor PLX4032. Such a clinical trial will be the first to target BRAF (e.g. cell proliferation) and to target melanoma cell fate using leflunomide. We are the first to show that Leflunomide blocks neural crest cell fate by inhibiting transcriptional elongation (e.g. inhibiting c-myc and mitf (FIG. 9, 13) directed genes.)

Combination therapies that include BRAF inhibitors will be particularly important for treating melanoma, especially within the context of developing long term responses. PLX40321 (Tsai, J. et al. Discovery of a selective inhibitor of oncogenic B-Raf kinase with potent antimelanoma activity. *Proc. Natl. Acad. Sci. U.S.A.* 105, 3041-3046 (2008)), and GSK211843616 (Kefford, R. A. et al. Phase I/II study of GSK2118436, a selective inhibitor of oncogenic mutant BRAF kinase, in patients with metastatic melanoma and other solid tumors. *J. Clin. Oncol.* 27, Abstract 8503 (2010)), the first generation of highly selective BRAF inhibitors, have completed phase II and (in the case of PLX4032) phase III testing; both have demonstrated unprecedented short-term efficacy in patients with metastatic melanoma that harbors a BRAF mutation. Approximately 60% of patients achieve objective responses early in the course of therapy, and approximately 90% of all patients realize some degree of tumor regression. However, most responses are not long-lasting and the overall median progression-free survival (PFS) is 6 to 7 months for all patients treated. Very few patients (3-5%) achieve complete responses, but when they do occur they are more long lasting. Thus, one metrics for judging improvement in outcome for the combination regimen with BRAF inhibitors is to improve the duration of response (PFS) or increase the percentage of patients with complete responses, by a statistically significant amount. It is expected that the combination of BRAF inhibitor PLX4032 and leflunomide will significantly improve PFS, or significantly increase the percent of patients with complete responses.

For controls, tumor biopsy samples before, during and at progression using single-agents PLX and GSK2118436 will be taken and analyzed; and compared to the combination therapy of the phase II trial that combines leflunomide and PLX.

Leflunomide is given to patients with arthritis, at doses that produce steady state concentrations exceeding those used in our preclinical studies. Thus, we will start with the FDA-approved dose of leflunomide (Kaplan, M. J. Leflunomide Aventis Pharma. Curr. Opin. Investig Drugs 2, 222-230 (2001)). We expect that doses much smaller than those required for therapeutic efficacy in arthritis patients will be needed for therapeutic efficacy in melanoma treatment. We will also start with the standard dose of PLX in our proposed trial. Given the efficacy of the combination in preclinical studies, we expect that doses smaller than those required for therapeutic efficacy in arthritis patients will be needed for therapeutic efficacy in melanoma treatment.

An example dose and administration regime follows: Within 6-12 hours of a single dose, leflunomide is metabolized into a single active metabolite that has a long half-life (~2 weeks). Therefore, when leflunomide is given in 3 daily loading doses (100 mg daily for 3 days), followed by lower daily doses (20 mg per day), it produces steady-state concentrations of approximately 60 mcg/mL (Rozman, B. Clinical pharmacokinetics of leflunomide. Clin. Pharmacokinet 41, 421-430 (2002)). Neither the parent compound nor the active metabolite is metabolized by CYP450 isoenzymes, so there is very little possibility of a drug-drug interaction with PLX. In placebo-controlled clinical trials with use of leflunomide in arthritis patients, the only treatment-related adverse event that was more prevalent for leflunomide than with placebo was elevation of liver transaminase. While this is also seen with PLX, it is rarely dose limiting. We thus have a low concern for leflunomide contributing to the toxicity of PLX. As is standard practice, we will monitor liver transaminases in our patients using means well known to those of skill in the art.

The primary endpoint of the proposed phase II trial that combines leflunomide with PLX will be PFS; we expect improvement in median PFS from 7 months (observed in phase I, II and III trials with single-agent PLX) to 10 months or more. Assuming 90% power and a type I error of 5%, this would require 43 patients. Our secondary clinical endpoint is complete response. We will use 90% power to detect an increase in complete rate to 12% or higher. A critical secondary endpoint will be the determination of pharmacodynamic effects of leflunomide in patients' tumors: to accomplish this, patients will start leflunomide as a single-agent for two weeks, before initiating PLX. Of the 43 patients to be accrued, we will require that 20 patients have tumors (cutaneous, subcutaneous or palpable lymph node metastases) that can be biopsied before and during treatment with use of a core needle or 3-4 mm punch biopsy. The remaining 23 patients may be accrued independently of the ability to perform biopsies, and once enrolled, only patients with tumors that can be biopsied will be accrued for the remainder of the trial. Biopsies will be performed before the initiation of treatment and between days 10-14 of single-agent leflunomide treatment.

Example III Additional Compounds for the Treatment of Melanoma

We assessed the ability of multiple DHODH inhibitors for their ability to treat melanoma both in vitro and in vivo: $C_{19}H_{14}F_2N_2O_3$, compound 1; $C_{20}H_{16}F_2N_2O_3$, compound 2; $C_{18}H_{13}F_6NO_4$, compound 3; $C_{19}H_{16}F_3NO_4$, compound 4; $C_{19}H_{10}F_5NO_4S$, compound 5; $C_{19}H_{14}FNO_4S$, compound 6; $C_{20}H_{15}F_4NO_4$, compound 7; $C_{19}H_{17}NO_4$, compound 8; $C_{20}H_{17}F_2NO_4$, compound 9; and $C_{20}H_{18}FNO_4$, compound 10. FIG. 21 shows the chemical structures of DHODH inhibitors compounds 1-4.

Compounds 1 and 2 were synthesized as described in U.S. Patent Publication 2010/007898 and compounds 3 and 4 were synthesized as described in U.S. Pat. No. 7,074,831, each of which are herein incorporated by reference in their entireties. FIG. 22 show the chemical structures of DHODH inhibitors for compounds 5 to 10. Synthesis of compound 5 and compound 6 is described in U.S. Patent Publication 2004/0192758, which is herein incorporated by reference in its entirety. Compounds 7-10 are described in U.S. Patent Publication 2006/0199859, and in U.S. Pat. No. 7,176,241, which are herein incorporated by reference in their entirety.

Figure 24A:
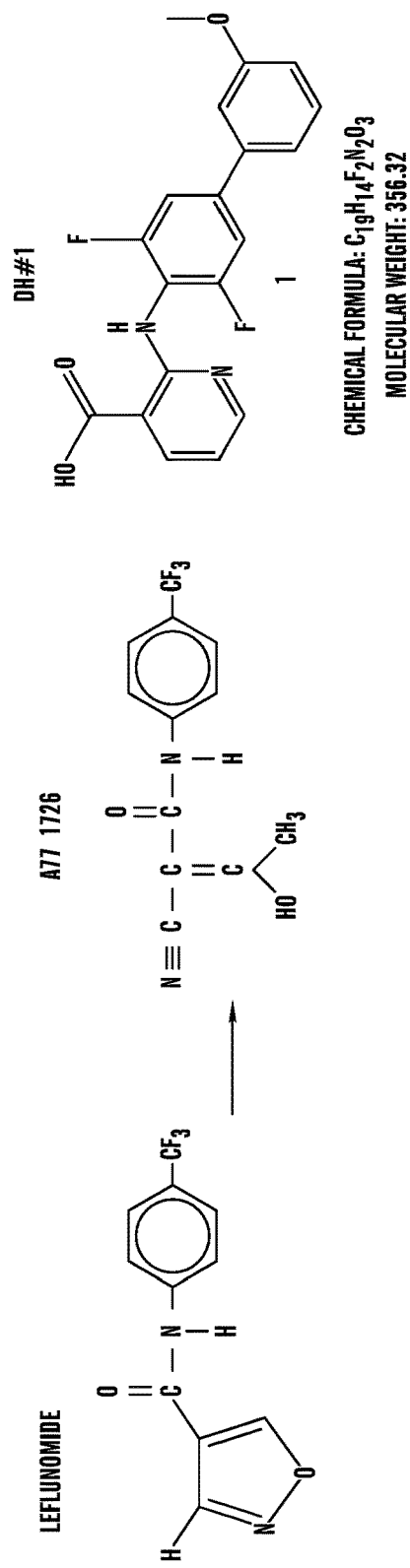
FIGS. 24a to 24b show chemical structures and in situ hybridization (ISH) staining in Zebrafish.
Figure 24B:
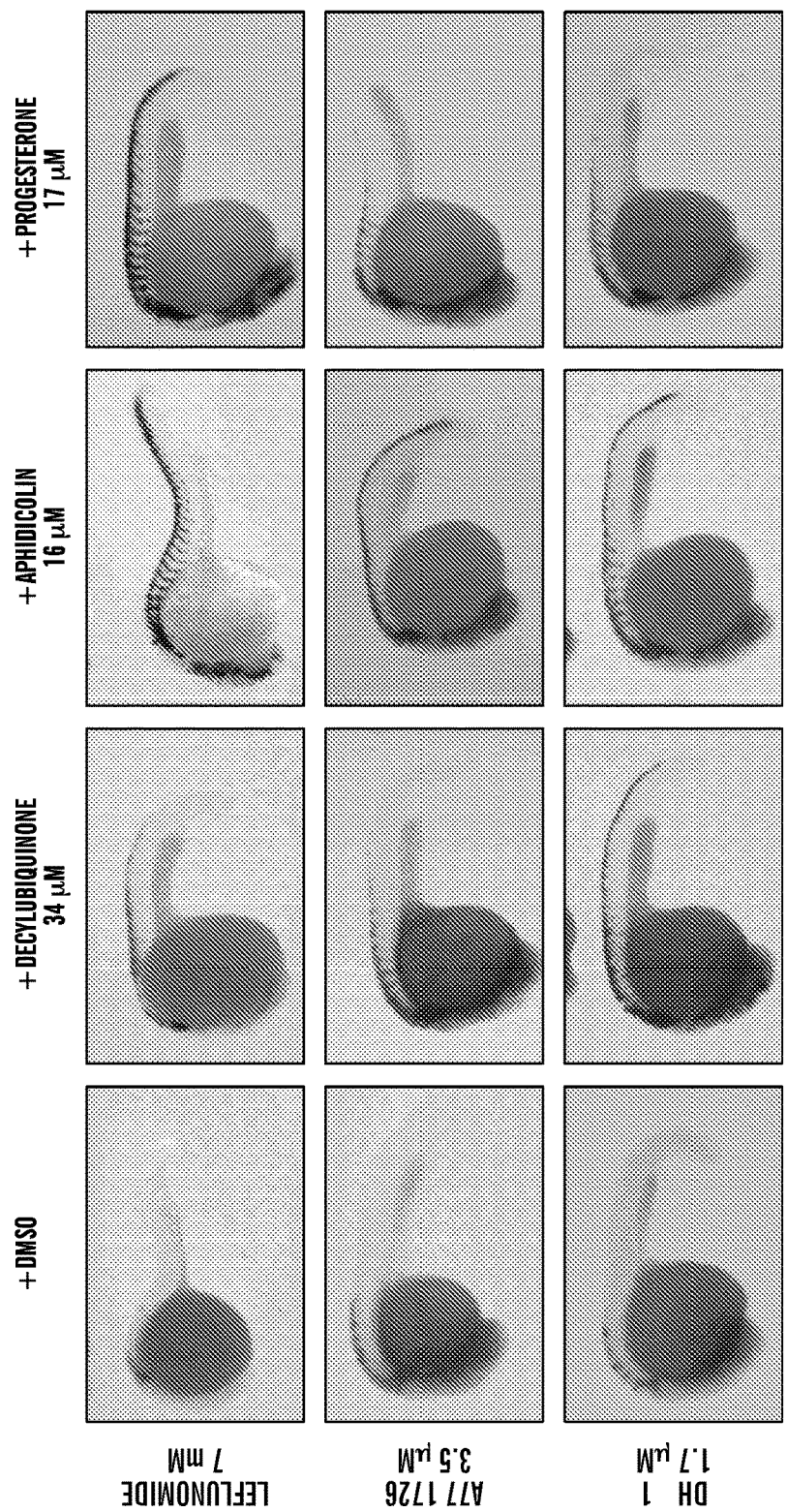

We used in situ hybridization (ISH) staining in Zebrafish embryos to monitor the suppression of neural crest progenitors in the presence of the various compounds as a means to assess the efficacy of the compounds in treatment of melanoma. FIG. 24 shows the chemical structures of leflunomide and its active metabolite A77126, and a structurally different DHODH inhibitor compound 1 (inhibitor DH#1). FIG. 24b shows the effect of compound 1, leflunomide, and A77126, on Zebrafish embryos on neural crest development, in the presence of DMSO, Decylubiquinone, Aphiadicolin, or Progesterone. ISH staining indicates that each of these inhibitors (leflunomide, A771726, or DH #1) leads to reduction in expression of the neural crest, depicted by an in situ hybridization for the neural crest marker crestin. However, chemicals including decylubiquinone, aphidicolin, and progesterone suppress these drugs and lead to a rescue of the neural crest population.

Figure 25A:
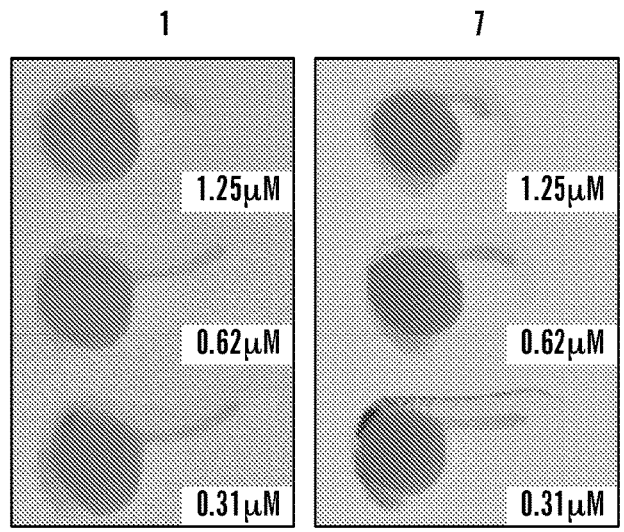
FIGS. 25a to 25b show in situ hybridization (ISH) staining in Zebrafish embryos to monitor neural crest development in the presence of compound 1, compound 7, leflunomide, compound 5 and compound 6 (See FIGS. 21-23 for compound structure and formula). Different concentrations of the DHODH inhibitors and in situ for crestin revealed compound 1 and compound 7 (FIG. 25a (#1 and #7) impair crestin expression at lower doses compared to leflunomide and compounds 5 and 6, FIG. 25b #5 and #6, respectively. The compounds showed varied strength in their ability to inhibit neural crest development, the effect of compound 1>compound 7>leflunomide, which is approximately the same as compounds 5 and 6.
Figure 25B:
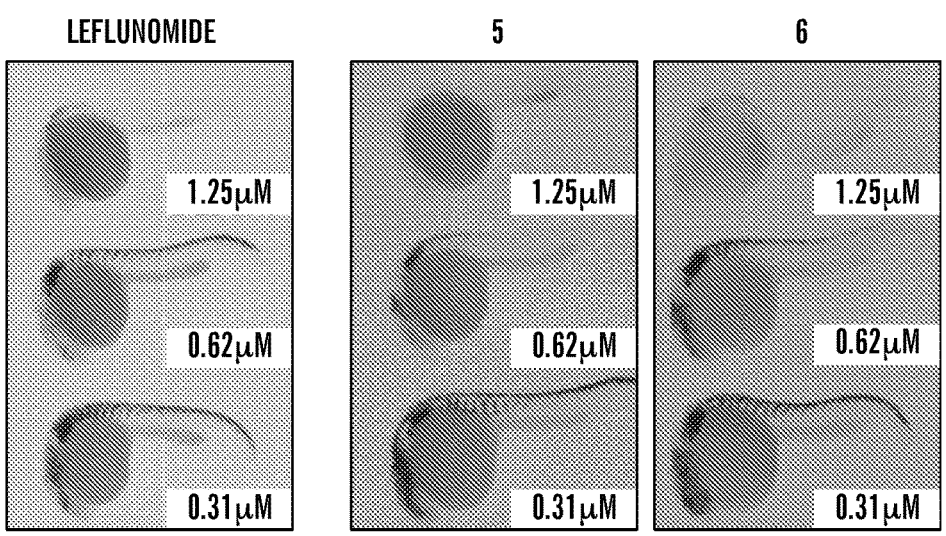

The efficacy of compound 1, compound 7, leflunomide, compound 5 and compound 6, was also determined by in situ hybridization (ISH) staining in Zebrafish embryos by monitoring neural crest development in the presence of the compounds (See FIGS. 25a to 25b; FIGS. 21-23 for compound structure and formula). Different concentrations of the DHODH inhibitors and in situ for crestin revealed compound 1 and compound 7 (FIG. 25a (#1 and #7) impair crestin expression at lower doses compared to leflunomide and compounds 5 and 6, FIG. 25b #5 and #6, respectively. The compounds showed varied strength in their ability to inhibit neural crest development, e.g. the effect of compound 1>compound 7>leflunomide, which is approximately the same as compounds 5 and 6.

Figure 26:
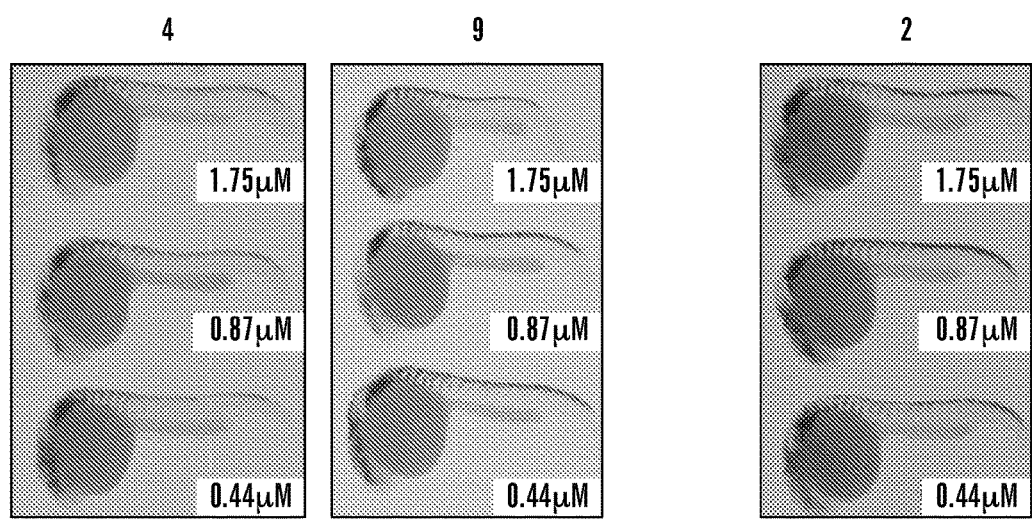
FIG. 26 shows in situ hybridization (ISH) staining in Zebrafish embryos to monitor neural crest development in the presence of compound 4, compound 9 and compound 2 (#4, #9 and #2 respectively; See FIGS. 21 to 23 for compound structure and formula). When referring also to FIG. 25, it is shown that DHODH inhibitors #4, #9 and #2 are less effective than leflunomide. Indeed at 1.75 uM these drugs do not affect crestin expression like observed upon the same dose of leflunomide in FIG. 25b.

The efficacy of compound 4, compound 9 and compound 2 is shown in FIG. 26 (#4, #9 and #2 respectively; See FIGS. 21 to 23 for compound structure and formula). When referring also to the results obtained in FIG. 25, it is shown that DHODH inhibitors #4, #9 and #2 are less effective than leflunomide. Indeed at 1.75 uM these drugs do not affect crestin expression like observed upon the same dose of leflunomide in FIG. 25b. The effect of compound 1>compound 7>leflunomide, which is approximately the same as compounds 5 and 6, which >compound 4, which is about the same as compound 9, which >compound 10>compound 2.

We also tested the effect of all of the DHODH inhibitors compounds 1-10 (DHODH analogs) (See FIGS. 21-23) on A375 cells after 3 days of treatment, See FIG. 27 for the results. Compounds 1, 4, and 7 significantly decreased cell proliferation at lower doses compared to leflunomide and A771726.

FIGS. 28a to 28e show graphs depicting the effects of leflunomide, compound 1 (PH-1), and compound 7 (PH-7) (See FIG. 21 (compound 1) and FIG. 23 (compound 7)) on the indicated melanoma cells in vitro. FIG. 28a, M481 cells. FIG. 28b, A375 cells. FIG. 28c, M405 cells. FIG. 28d, M528 cells. FIG. 28e, M715 cells. Compound 1, compound 7 and leflumide affect cell viability of human primary melanoma cells. FIGS. 28a and 28b show respectively that lefunomide as well as DHODH #1 (PH-01, i.e. compound 1), DHODH#7 (PH-07, i.e. compound 7) impair cell survival in primary human melanoma cells (M481) and in the melanoma cell line (A375). FIG. 28c shows that the effect of these inhibitors is variable in different primary melanoma cells (M405, M528 and M715).

We also tested the in vivo effects of leflunimide in combination with digitoxin on M405 tumor xenografts in mouse. FIG. 29a, shows the effect on tumor diameter (cm) vs. time. FIG. 29b, effect on tumor weight. FIG. 29c, effect on frequency of melanoma cells in the blood. FIG. 29d, Total flux (photons/second). The M405 cells were not sensitive to drug treatment as shown in FIG. 28 and accordingly there is no effect on tumor growth (FIG. 29a) and number of melanoma cells in blood circulating cells (FIG. 29b). But there is significant difference in blood circulating cells in co-treatment with Leflunomide and Digitoxin. No change in flux was observed (FIG. 29d).

Figure 30:
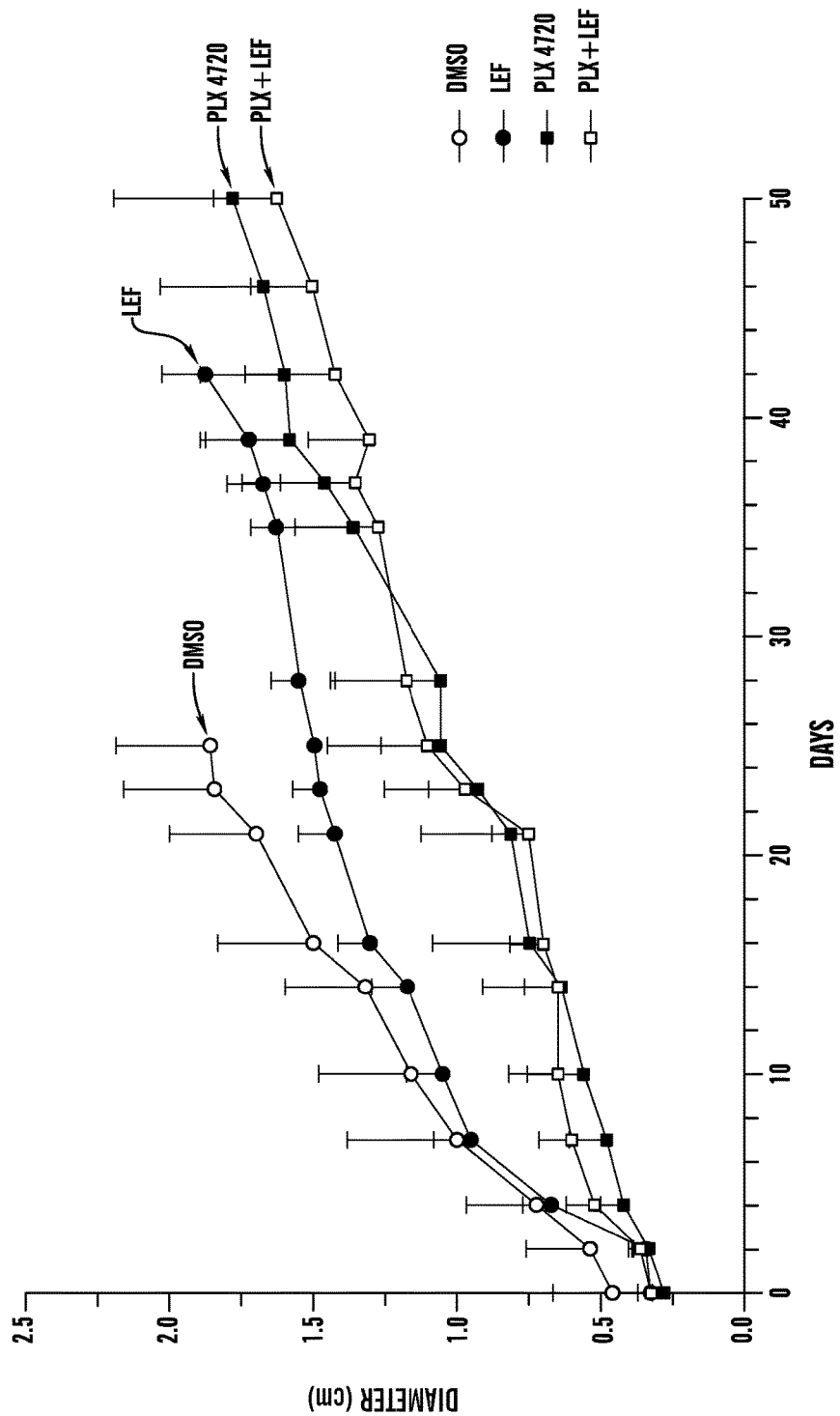
FIG. 30 is a graph of in vivo effects of the combination of DHODH inhibitor and Braf inhibitor on tumor volume, of M481 primary human melanoma xenografts in mice.

In addition, M841 primary human melanoma xenografts in mice revealed that leflunomide and other DHODH inhibitors are more effective when used in combination with Plexicon (FIG. 30 and data not shown). FIG. 30 shows the in vivo effects of the combination of DHODH inhibitor and Braf inhibitor on tumor volume, of M481 primary human melanoma xenografts in mice.

Figure 31:
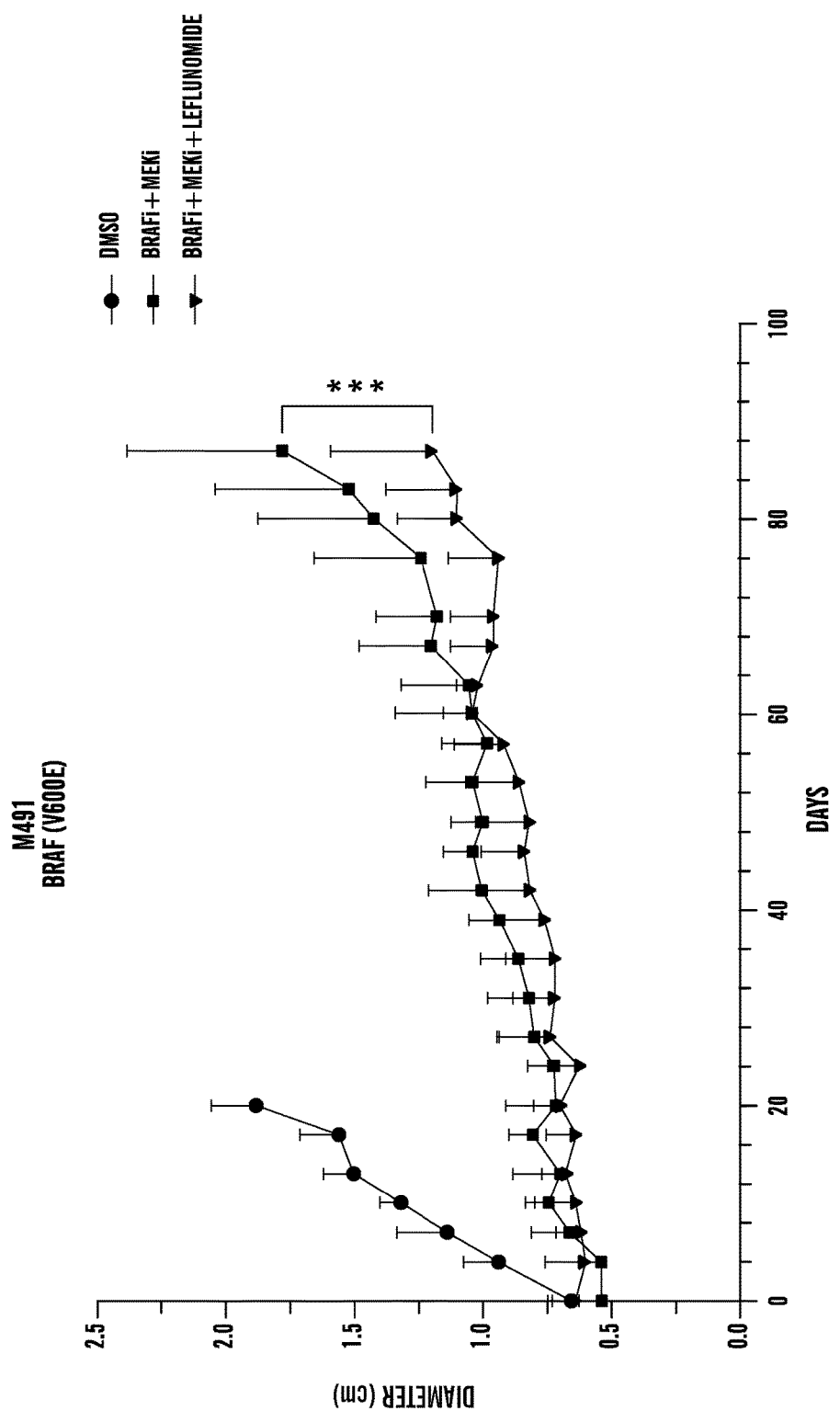
FIG. 31 is a graph that shows the effect leflunomide in combination with Braf and Mek inhibitors on primary human melanoma cells xenografts in mice. Human BRAFV600 (M491) cells were treated with a combination of drugs including BRAF inhibitors (BRAFi), MEK inhibitors (MEKi) and Leflunomide. Leflunomide significantly impair tumor growth in combination with BRAFi and MEKi.

We have also determined that Leflunomide and other DHODH inhibitors significantly impair tumor growth in combination with BRAFi and MEKi (FIG. 31 and Data not shown). FIG. 31 shows the effect leflunomide in combination with Braf and Mek inhibitors on primary human melanoma cells xenografts in mice. Human BRAFV600 (M491) cells were treated with a combination of drugs including BRAF inhibitors (BRAFi), MEK inhibitors (MEKi) and Leflunomide.

SEQUENCES
Human wt BRAF (SEQ ID NO: 1)

```
  1 maalsggggg gaepgqalth gdmepeagag agaaassaad paipeevwni kqmikltqeh
 61 iealldkfgg ehnppsiyle ayeeytskld alqqreqqll eslgngtdfs vsssasmdtv
121 tsssssslsv lpsslsvfqn ptdvarsnpk spqkpivrvf lpnkqrtvvp arcgvtvrds
181 lkkalmmrgl ipeccavyri qdgekkpigw dtdiswltge elhvevlenv pltthnfvrk
241 tfftlafcdf crkllfqgfr cqtcgykfhq rcstevplmc vnydqldllf vskffehhpi
301 pqeeaslaet altsgsspsa pasdsigpqi ltspspsksi pipqpfrpad edhrnqfgqr
361 drsssapnvh intiepvnid dlirdqgfrg dggsttglsa tppaslpgsl tnvkalqksp
421 gpqrerksss ssedrnrmkt lgrrdssddw eipdgqitvg qrigsgsfgt vykgkwhgdv
481 avkmlnvtap tpqqlqafkn evgvlrktrh vnillfmgys tkpqlaivtq wcegsslyhh
541 lhiietkfem iklidiarqt aqgmdylhak siihrdlksn niflhedltv kigdfglatv
601 ksrwsgshqf eqlsgsilwm apevirmqdk npysfqsdvy afgivlyelm tgqlpysnin
661 nrdqiifmvg rgylspdlsk vrsncpkamk rlmaeclkkk rderplfpqi lasiellars
721 lpkihrsase pslnragfqt edfslyacas pktpiqaggy gafpvh
```

Human dihydroorotate dehydrogenase (DHODH) protein (SEQ IN NO:2)

```
  1 klpwrhlqkr aqdaviilgg ggllfasylm atgderfyae hlmptlqgll dpesahrlav
 61 rftslgllpr arfqdsdmle vrvlghkfrn pvgiaagfdk hgeavdglyk mgfgfveigs
121 vtpkpqegnp rprvfrlped qavinrygfn shglsvvehr lrarqqkqak ltedglplgv
181 nlgknktsvd aaedyaegvr vlgpladylv vnvsspntag lrslqgkael rrlltkvlqe
241 rdglrrvhrp avlvkiapdl tsqdkedias vvkelgidgl ivtnttvsrp aglqgalrse
301 tgglsgkplr dlstqtirem yaltqgrvpi igvggvssgq dalekiraga slvqlytalt
361 fwgppvvgkv kreleallke qgfggvtdai gadhrr
```

Human BRAF(V600E)

(SEQ ID NO: 3)

```
  1 maalsggggg gaepgqalth gdmepeagag agaaassaad paipeevwni kqmikltqeh
 61 iealldkfgg ehnppsiyle ayeeytskld alqqreqqll eslgngtdfs vsssasmdtv
121 tsssssslsv lpsslsvfqn ptdvarsnpk spqkpivrvf lpnkqrtvvp arcgvtvrds
181 lkkalmmrgl ipeccavyri qdgekkpigw dtdiswltge elhvevlenv pltthnfvrk
241 tfftlafcdf crkllfqgfr cqtcgykfhq rcstevplmc vnydqldllf vskffehhpi
301 pqeeaslaet altsgsspsa pasdsigpqi ltspspsksi pipqpfrpad edhrnqfgqr
361 drsssapnvh intiepvnid dlirdqgfrg dggsttglsa tppaslpgsl tnvkalqksp
421 gpqrerksss ssedrnrmkt lgrrdssddw eipdgqitvg qrigsgsfgt vykgkwhgdv
481 avkmlnvtap tpqqlqafkn evgvlrktrh vnillfmgys tkpqlaivtq wcegsslyhh
541 lhiietkfem iklidiarqt aqgmdylhak siihrdlksn niflhedltv kigdfglate
601 ksrwsgshqf eqlsgsilwm apevirmqdk npysfqsdvy afgivlyelm tgqlpysnin
661 nrdqiifmvg rgylspdlsk vrsncpkamk rlmaeclkkk rderplfpqi lasiellars
721 lpkihrsase pslnragfqt edfslyacas pktpiqaggy gafpvh
```

Human dihydroorotate dehydrogenase (DHODH) mRNA - GenBank accession NM_001361

(SEQ ID NO: 4)

```
  1 gggcttaatg acggaaggag catggcgtgg agacacctga aaaagcgggc ccaggatgct
 61 gtgatcatcc tggggggagg aggacttctc ttcgcctcct acctgatggc cacgggagat
121 gagcgtttct atgctgaaca cctgatgccg actctgcagg ggctgctgga cccggagtca
```

-continued

```
 181 gcccacagac tggctgttcg cttcacctcc ctggggctcc ttccacgggc cagatttcaa
 241 gactctgaca tgctggaagt gagagttctg ggccataaat tccgaaatcc agtaggaatt
 301 gctgcaggat ttgacaagca tggggaagcc gtggacggac tttataagat gggctttggt
 361 tttgttgaga taggaagtgt gactccaaaa cctcaggaag aaaccctag acccagagtc
 421 ttccgcctcc ctgaggacca agctgtcatt aacaggtatg gatttaacag tcacgggctt
 481 tcagtggtgg aacacaggtt acgggccaga cagcagaagc aggccaagct cacagaagat
 541 ggactgcctc tgggggtcaa cttggggaag aacaagacct cagtgacgc cgcggaggac
 601 tacgcagaag gggtgcgcgt actgggcccc ctggccgact acctggtggt gaatgtgtcc
 661 agccccaaca ctgccgggct gcggagcctt cagggaaagg ccgagctgcg ccgcctgctg
 721 accaaggtgc tgcaggagag ggatggcttg cggagagtgc acaggccggc agtcctggtg
 781 aagatcgctc ctgacctcac cagccaggat aaggaggaca ttgccagtgt ggtcaaagag
 841 ttgggcatcg atgggctgat tgttacgaac accaccgtga gtcgccctgc gggcctccag
 901 ggtgccctgc gctctgaaac aggagggctg agtgggaagc ccctccggga tttatcaact
 961 caaaccattc gggagatgta tgcactcacc caaggccgag ttcccataat tggggttggt
1021 ggtgtgagca gcgggcagga cgcgctggag aagatccggg caggggcctc cctggtgcag
1081 ctgtacacgg ccctcacctt ctgggggcca cccgttgtgg gcaaagtcaa gcgggaactg
1141 gaggcccttc tgaaagagca gggctttggc ggagtcacag atgccattgg agcagatcat
1201 cggaggtgag gacagcgtct gacgggaagc ctgatctgga accttcccaa ggactcaggc
1261 aagcctttgt ggctggatca tgagaggagg gactccatct tgagccatgt cccccagcca
1321 tggcatggct gcactgtaaa cgccaatcgg ggggtcacca ggatcaaccg caggctttct
1381 tcagtcccct ggtcagacca taaactgcat ttttgattct ttgtggattc aaaccctagg
1441 atccatcagt cttgcaagga cattgaatat taggaggaaa aagtcatgga aaaaataaag
1501 ccatttagaa cctgggtttc aacgctagcc ctttctggtt tgccataggc cctgccaaga
1561 tactgcaggt ccatccaggc ctctgctatc tgcatctgca gtgggcttcc caggaacttg
1621 actgtctttc atttgatctt tattttgtt tatttaatat tttaaacttt attttaaaaa
1681 tatttcaaac ataagggcgg ggtgtggtgg ctcatgcctg taatcccagc actttgggag
1741 gccgaggcgg gcggatcacc tgaggccagg agttggagac cagccaggcc accatggtga
1801 aaccctgtct ctaccaaaaa tacaaaaaat tagccagata ttgtggcagg cacttttaat
1861 cccagctact cgggaggctg aggcaggaga attgcttgaa cctgggaggc ggaggttgca
1921 gtgagccaag attgcaccag tgcactccag cttgggcgac agatcaagac tctgtcacac
1981 acaaaacaaa caaacaaatt ttcccgtttc tctctgtccc tttctctata acatggataa
2041 aatattcacg tcttatgtat ttattattgc tgagtcattg gtgccttatt cttcagtgtt
2101 tcagtctgta tctcctaagc atcctgatgt tagtttttg actataaaat tgacctgcat
2161 tctttactag caattcaaac ggtacagcac tcttgaagtg taaacattcc tgttcctcct
2221 caccccactc tgcagacatg cctttctgtc tgtcctccca gacttttccc ctgcataaag
2281 atgttcattt tgtacataca ctcagacata catgtggctg tatttttgt ataccgattt
2341 ctggatggaa tgcacactgt tatctgttta gttactttat gttttcatac aaatgacatc
2401 atcccacaaa tagaattctg ccatttaaaa aaaaaaaa
```

-continued

Human BRAF mRNA: v-raf murine sarcoma viral oncogene homolog B1 (BRAF),
(SEQ ID NO: 5)

```
   1 cgcctccctt ccccctcccc gcccgacagc ggccgctcgg gccccggctc tcggttataa
  61 gatggcggcg ctgagcggtg gcggtggtgg cggcgcggag ccgggccagg ctctgttcaa
 121 cggggacatg gagcccgagg ccggcgccgg cgccggcgcc gcggcctctt cggctgcgga
 181 ccctgccatt ccggaggagg tgtggaatat caaacaaatg attaagttga cacaggaaca
 241 tatagaggcc ctattggaca aatttggtgg ggagcataat ccaccatcaa tatatctgga
 301 ggcctatgaa gaatacacca gcaagctaga tgcactccaa caaagagaac aacagttatt
 361 ggaatctctg gggaacggaa ctgatttttc tgtttctagc tctgcatcaa tggataccgt
 421 tacatcttct tcctcttcta gcctttcagt gctaccttca tctctttcag tttttcaaaa
 481 tcccacagat gtggcacgga gcaaccccaa gtcaccacaa aaacctatcg ttagagtctt
 541 cctgcccaac aaacagagga cagtggtacc tgcaaggtgt ggagttacag tccgagacag
 601 tctaaagaaa gcactgatga tgagaggtct aatcccagag tgctgtgctg tttacagaat
 661 tcaggatgga gagaagaaac caattggttg gacactgat atttcctggc ttactggaga
 721 agaattgcat gtggaagtgt tggagaatgt tccacttaca acacacaact tgtacgaaaa
 781 aacgtttttc accttagcat tttgtgactt ttgtcgaaag ctgcttttcc agggtttccg
 841 ctgtcaaaca tgtggttata aatttcacca gcgttgtagt acagaagttc cactgatgtg
 901 tgttaattat gaccaacttg atttgctgtt tgtctccaag ttctttgaac caccccaat
 961 accacaggaa gaggcgtcct tagcagagac tgccctaaca tctggatcat ccccttccgc
1021 acccgcctcg gactctattg gccccaaat tctcaccagt ccgtctcctt caaaatccat
1081 tccaattcca cagcccttcc gaccagcaga tgaagatcat cgaaatcaat ttgggcaacg
1141 agaccgatcc tcatcagctc ccaatgtgca tataaacaca atagaacctg tcaatattga
1201 tgacttgatt agagaccaag gatttcgtgg tgatggagga tcaaccacag gtttgtctgc
1261 tacccccct gcctcattac ctggctcact aactaacgtg aaagcttac agaaatctcc
1321 aggacctcag cgagaaagga agtcatcttc atcctcagaa gacaggaatc gaatgaaaac
1381 acttggtaga cgggactcga gtgatgattg ggagattcct gatgggcaga ttacagtggg
1441 acaaagaatt ggatctggat catttggaac agtctacaag ggaaagtggc atggtgatgt
1501 ggcagtgaaa atgttgaatg tgacagcacc tacacctcag cagttacaag ccttcaaaaa
1561 tgaagtagga gtactcagga aaacacgaca tgtgaatatc ctactcttca tgggctattc
1621 cacaaagcca caactggcta ttgttaccca gtggtgtgag ggctccagct tgtatcacca
1681 tctccatatc attgagacca atttgagat gatcaaactt atagatattg cacgacagac
1741 tgcacagggc atggattact acacgccaa gtcaatcatc cacagagacc tcaagagtaa
1801 taatatattt cttcatgaag acctcacagt aaaaataggt gattttggtc tagctacagt
1861 gaaatctcga tggagtgggt cccatcagtt gaacagttg tctggatcca ttttgtggat
1921 ggcaccagaa gtcatcagaa tgcaagataa aaatccatac agctttcagt cagatgtata
1981 tgcatttgga attgttctgt atgaattgat gactggacag ttaccttatt caaacatcaa
2041 caacagggac cagataattt ttatggtggg acgaggatac ctgtctccag atctcagtaa
2101 ggtacggagt aactgtccaa aagccatgaa gagattaatg gcagagtgcc tcaaaaagaa
2161 aagagatgag agaccactct ttccccaaat tctcgcctct attgagctgc tggcccgctc
2221 attgccaaaa attcaccgca gtgcatcaga accctccttg aatcgggctg gtttccaaac
2281 agaggatttt agtctatatg cttgtgcttc tccaaaaaca cccatccagg cagggggata
```

-continued

```
2341 tggtgcgttt cctgtccact gaaacaaatg agtgagagag ttcaggagag tagcaacaaa 2401 aggaaaataa atgaacatat gtttgcttat atgttaaatt gaataaaata ctctcttttt 2461 ttttaaggtg aaccaaagaa cacttgtgtg gttaaagact agatataatt tttccccaaa 2521 ctaaaattta tacttaacat tggatttta acatccaagg gttaaaatac atagacattg 2581 ctaaaaattg gcagagcctc ttctagaggc tttactttct gttccgggtt tgtatcattc 2641 acttggttat tttaagtagt aaacttcagt ttctcatgca acttttgttg ccagctatca 2701 catgtccact agggactcca gaagaagacc ctacctatgc ctgtgtttgc aggtgagaag 2761 ttggcagtcg gttagcctgg gttagataag gcaaactgaa cagatctaat ttaggaagtc 2821 agtagaattt aataattcta ttattattct taataatttt tctataacta tttctttta 2881 taacaatttg gaaaatgtgg atgtctttta tttccttgaa gcaataaact aagtttcttt 2941 ttataaaaa.
```

The invention claimed is:

1. A method for treating melanoma in a subject comprising: (i) selecting a subject with rising cancer marker protein levels or having a family history of cancer or who has had a melanoma removed surgically; and (ii) administering to a subject in need thereof a therapeutically effective amount of an inhibitor of dihydroorotate dehydrogenase (DHODH) and administering an effective amount of an inhibitor of oncogenic BRAF, wherein the inhibitor of DHODH is selected from the group consisting of:

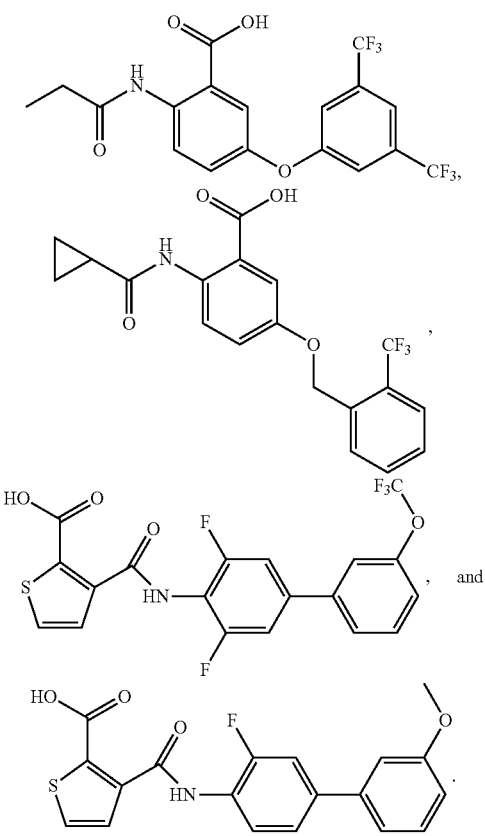

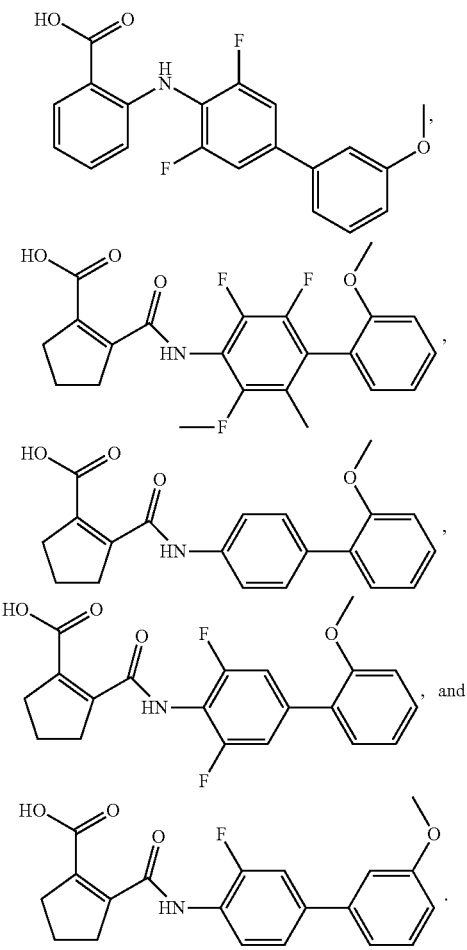

2. The method of claim 1, wherein the inhibitor of oncogenic BRAF is selected from the group consisting of: a small molecule, a nucleic acid RNA, a nucleic acid DNA, a protein, a peptide, and an antibody.

3. The method of claim 1, wherein the oncogenic BRAF is BRAF(V600E).

4. The method of claim 1, wherein the inhibitor of oncogenic BRAF is selected from the group consisting of: Sorafenib, RAF265, XL281, AZ628, GSK2118436, GDC-0879, PLX4032, and PLX4720.

5. The method of claim 1, wherein the inhibitor of oncogenic BRAF and inhibitor of dihydroorotate dehydrogenase (DHODH) are administered to the subject sequentially or simultaneously.

6. A method for treating melanoma in a subject comprising: (i) selecting a subject with rising cancer marker protein levels or having a family history of cancer or who has had a melanoma removed surgically; and (ii) administering to a subject in need thereof a therapeutically effective amount of an inhibitor of dihydroorotate dehydrogenase (DHODH) and administering an effective amount of an inhibitor of oncogenic BRAF, wherein the inhibitor of DHODH is selected from the group consisting of:

7. The method of claim 6, wherein the inhibitor of dihydroorotate dehydrogenase is

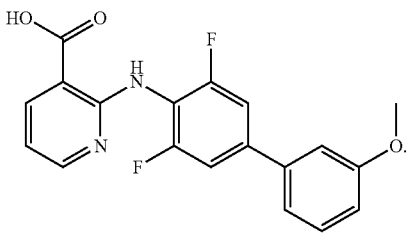 [SMILES: COc1cccc(-c2cc(F)c(Nc3ncccc3C(=O)O)c(F)c2)c1]

8. The method of claim 6, wherein the inhibitor of dihydroorotate dehydrogenase (DHODH) is

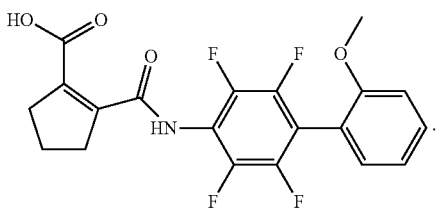 [SMILES: COc1ccccc1-c1c(F)c(F)c(NC(=O)C2=C(C(=O)O)CCC2)c(F)c1F]

9. The method of claim 6, wherein the inhibitor of oncogenic BRAF is selected from the group consisting of: a small molecule, a nucleic acid RNA, a nucleic acid DNA, a protein, a peptide, and an antibody.

10. The method of claim 6, wherein the oncogenic BRAF is BRAF(V600E).

11. The method of claim 6, wherein the inhibitor of oncogenic BRAF is selected from the group consisting of: Sorafenib, RAF265, XL281, AZ628, GSK2118436, GDC-0879, PLX4032, and PLX4720.

12. The method of claim 6, wherein the inhibitor of oncogenic BRAF and inhibitor of dihydroorotate dehydrogenase (DHODH) are administered to the subject sequentially or simultaneously.

* * * * *

SEQUENCE LISTING

<160> NUMBER OF SEQ ID NOS: 12

<210> SEQ ID NO 1
<211> LENGTH: 766
<212> TYPE: PRT
<213> ORGANISM: Homo sapiens

<400> SEQUENCE: 1

```
Met Ala Ala Leu Ser Gly Gly Gly Gly Ala Glu Pro Gly Gln
1               5                   10                  15

Ala Leu Phe Asn Gly Asp Met Glu Pro Glu Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240
```

```
Thr Phe Phe Thr Leu Ala Phe Cys Asp Phe Cys Arg Lys Leu Leu Phe
            245                 250                 255
Gln Gly Phe Arg Cys Gln Thr Cys Gly Tyr Lys Phe His Gln Arg Cys
            260                 265                 270
Ser Thr Glu Val Pro Leu Met Cys Val Asn Tyr Asp Gln Leu Asp Leu
            275                 280                 285
Leu Phe Val Ser Lys Phe Phe Glu His His Pro Ile Pro Gln Glu Glu
            290                 295                 300
Ala Ser Leu Ala Glu Thr Ala Leu Thr Ser Gly Ser Ser Pro Ser Ala
305                 310                 315                 320
Pro Ala Ser Asp Ser Ile Gly Pro Gln Ile Leu Thr Ser Pro Ser Pro
            325                 330                 335
Ser Lys Ser Ile Pro Ile Pro Gln Pro Phe Arg Pro Ala Asp Glu Asp
            340                 345                 350
His Arg Asn Gln Phe Gly Gln Arg Asp Arg Ser Ser Ser Ala Pro Asn
            355                 360                 365
Val His Ile Asn Thr Ile Glu Pro Val Asn Ile Asp Asp Leu Ile Arg
            370                 375                 380
Asp Gln Gly Phe Arg Gly Asp Gly Gly Ser Thr Thr Gly Leu Ser Ala
385                 390                 395                 400
Thr Pro Pro Ala Ser Leu Pro Gly Ser Leu Thr Asn Val Lys Ala Leu
            405                 410                 415
Gln Lys Ser Pro Gly Pro Gln Arg Glu Arg Lys Ser Ser Ser Ser Ser
            420                 425                 430
Glu Asp Arg Asn Arg Met Lys Thr Leu Gly Arg Arg Asp Ser Ser Asp
            435                 440                 445
Asp Trp Glu Ile Pro Asp Gly Gln Ile Thr Val Gly Gln Arg Ile Gly
450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
            485                 490                 495
Ala Phe Lys Asn Glu Val Gly Val Leu Arg Lys Thr Arg His Val Asn
            500                 505                 510
Ile Leu Leu Phe Met Gly Tyr Ser Thr Lys Pro Gln Leu Ala Ile Val
            515                 520                 525
Thr Gln Trp Cys Glu Gly Ser Ser Leu Tyr His His Leu His Ile Ile
            530                 535                 540
Glu Thr Lys Phe Glu Met Ile Lys Leu Ile Asp Ile Ala Arg Gln Thr
545                 550                 555                 560
Ala Gln Gly Met Asp Tyr Leu His Ala Lys Ser Ile Ile His Arg Asp
            565                 570                 575
Leu Lys Ser Asn Asn Ile Phe Leu His Glu Asp Leu Thr Val Lys Ile
            580                 585                 590
Gly Asp Phe Gly Leu Ala Thr Val Lys Ser Arg Trp Ser Gly Ser His
            595                 600                 605
Gln Phe Glu Gln Leu Ser Gly Ser Ile Leu Trp Met Ala Pro Glu Val
            610                 615                 620
Ile Arg Met Gln Asp Lys Asn Pro Tyr Ser Phe Gln Ser Asp Val Tyr
625                 630                 635                 640
Ala Phe Gly Ile Val Leu Tyr Glu Leu Met Thr Gly Gln Leu Pro Tyr
            645                 650                 655
```

```
Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Arg Asp Glu Arg
            690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
            755                 760                 765

<210> SEQ ID NO 2
<211> LENGTH: 396
<212> TYPE: PRT
<213> ORGANISM: Homo sapiens

<400> SEQUENCE: 2

Lys Leu Pro Trp Arg His Leu Gln Lys Arg Ala Gln Asp Ala Val Ile
1               5                   10                  15

Ile Leu Gly Gly Gly Gly Leu Leu Phe Ala Ser Tyr Leu Met Ala Thr
            20                  25                  30

Gly Asp Glu Arg Phe Tyr Ala Glu His Leu Met Pro Thr Leu Gln Gly
            35                  40                  45

Leu Leu Asp Pro Glu Ser Ala His Arg Leu Ala Val Arg Phe Thr Ser
50                  55                  60

Leu Gly Leu Leu Pro Arg Ala Arg Phe Gln Asp Ser Asp Met Leu Glu
65                  70                  75                  80

Val Arg Val Leu Gly His Lys Phe Arg Asn Pro Val Gly Ile Ala Ala
                85                  90                  95

Gly Phe Asp Lys His Gly Glu Ala Val Asp Gly Leu Tyr Lys Met Gly
            100                 105                 110

Phe Gly Phe Val Glu Ile Gly Ser Val Thr Pro Lys Pro Gln Glu Gly
            115                 120                 125

Asn Pro Arg Pro Arg Val Phe Arg Leu Pro Glu Asp Gln Ala Val Ile
            130                 135                 140

Asn Arg Tyr Gly Phe Asn Ser His Gly Leu Ser Val Val Glu His Arg
145                 150                 155                 160

Leu Arg Ala Arg Gln Gln Lys Gln Ala Lys Leu Thr Glu Asp Gly Leu
                165                 170                 175

Pro Leu Gly Val Asn Leu Gly Lys Asn Lys Thr Ser Val Asp Ala Ala
            180                 185                 190

Glu Asp Tyr Ala Glu Gly Val Arg Val Leu Gly Pro Leu Ala Asp Tyr
            195                 200                 205

Leu Val Val Asn Val Ser Ser Pro Asn Thr Ala Gly Leu Arg Ser Leu
            210                 215                 220

Gln Gly Lys Ala Glu Leu Arg Arg Leu Leu Thr Lys Val Leu Gln Glu
225                 230                 235                 240

Arg Asp Gly Leu Arg Arg Val His Arg Pro Ala Val Leu Val Lys Ile
                245                 250                 255

Ala Pro Asp Leu Thr Ser Gln Asp Lys Glu Asp Ile Ala Ser Val Val
            260                 265                 270
```

-continued

Lys Glu Leu Gly Ile Asp Gly Leu Ile Val Thr Asn Thr Thr Val Ser
            275                 280                 285

Arg Pro Ala Gly Leu Gln Gly Ala Leu Arg Ser Glu Thr Gly Gly Leu
        290                 295                 300

Ser Gly Lys Pro Leu Arg Asp Leu Ser Thr Gln Thr Ile Arg Glu Met
305                 310                 315                 320

Tyr Ala Leu Thr Gln Gly Arg Val Pro Ile Ile Gly Val Gly Gly Val
                325                 330                 335

Ser Ser Gly Gln Asp Ala Leu Glu Lys Ile Arg Ala Gly Ala Ser Leu
            340                 345                 350

Val Gln Leu Tyr Thr Ala Leu Thr Phe Trp Gly Pro Pro Val Val Gly
        355                 360                 365

Lys Val Lys Arg Glu Leu Glu Ala Leu Leu Lys Glu Gln Gly Phe Gly
370                 375                 380

Gly Val Thr Asp Ala Ile Gly Ala Asp His Arg Arg
385                 390                 395

<210> SEQ ID NO 3
<211> LENGTH: 766
<212> TYPE: PRT
<213> ORGANISM: Homo sapiens

<400> SEQUENCE: 3

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe

```
                   245                 250                 255
Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
            275                 280                 285

Leu Phe Val Ser Lys Phe Phe Glu His His Pro Ile Pro Gln Glu Glu
        290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ala Pro Asn
        355                 360                 365

Val His Ile Asn Thr Ile Glu Pro Val Asn Ile Asp Asp Leu Ile Arg
370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser
            420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
        450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Glu Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670
```

```
Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Lys Arg Asp Glu Arg
        690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
            755                 760                 765

<210> SEQ ID NO 4
<211> LENGTH: 2438
<212> TYPE: DNA
<213> ORGANISM: Homo sapiens

<400> SEQUENCE: 4
```

| | | | | | |
|---|---|---|---|---|---|
| gggcttaatg | acggaaggag | catggcgtgg | agacacctga | aaaagcgggc | ccaggatgct   60 |
| gtgatcatcc | tggggggagg | aggacttctc | ttcgcctcct | acctgatggc | cacgggagat  120 |
| gagcgtttct | atgctgaaca | cctgatgccg | actctgcagg | ggctgctgga | cccgagtca   180 |
| gcccacagac | tggctgttcg | cttcacctcc | ctggggctcc | ttccacgggc | cagatttcaa  240 |
| gactctgaca | tgctggaagt | gagagttctg | ggccataaat | tccgaaatcc | agtaggaatt  300 |
| gctgcaggat | ttgacaagca | tggggaagcc | gtggacggac | tttataagat | gggctttggt  360 |
| tttgttgaga | taggaagtgt | gactccaaaa | cctcaggaag | aaaccctag  | acccagagtc  420 |
| ttccgcctcc | ctgaggacca | agctgtcatt | aacaggtatg | gatttaacag | tcacgggctt  480 |
| tcagtggtgg | aacacaggtt | acgggccaga | cagcagaagc | aggccaagct | cacagaagat  540 |
| ggactgcctc | tggggtcaa  | cttggggaag | aacaagacct | cagtggacgc | cgcggaggac  600 |
| tacgcagaag | gggtgcgcgt | actgggcccc | ctggccgact | acctggtggt | gaatgtgtcc  660 |
| agccccaaca | ctgccgggct | gcggagcctt | cagggaaagg | ccgagctgcg | ccgcctgctg  720 |
| accaaggtgc | tgcaggagag | ggatggcttg | cggagagtgc | acaggccggc | agtcctggtg  780 |
| aagatcgctc | ctgacctcac | cagccaggat | aaggaggaca | ttgccagtgt | ggtcaaagag  840 |
| ttgggcatcg | atgggctgat | tgttacgaac | accaccgtga | gtcgccctgc | gggcctccag  900 |
| ggtgccctgc | gctctgaaac | aggagggctg | agtgggaagc | ccctccggga | tttatcaact  960 |
| caaaccattc | gggagatgta | tgcactcacc | caaggccgag | ttcccataat | tggggttggt | 1020 |
| ggtgtgagca | gcggcagga  | cgcgctggag | aagatccggg | cagggcctc  | cctggtgcag | 1080 |
| ctgtacacgg | ccctcacctt | ctgggggcca | cccgttgtgg | gcaaagtcaa | gcgggaactg | 1140 |
| gaggcccttc | tgaaagagca | gggctttggc | ggagtcacag | atgccattgg | agcagatcat | 1200 |
| cggaggtgag | gacagcgtct | gacgggaagc | ctgatctgga | accttcccaa | ggactcaggc | 1260 |
| aagcctttgt | ggctggatca | tgagaggagg | gactccatct | tgagccatgt | ccccagcca  | 1320 |
| tggcatggct | gcactgtaaa | cgccaatcgg | ggggtcacca | ggatcaaccg | caggctttct | 1380 |
| tcagtccctt | ggtcagacca | taaactgcat | ttttgattct | ttgtggattc | aaaccctagg | 1440 |
| atccatcagt | cttgcaagga | cattgaatat | taggaggaaa | aagtcatgga | aaaataaag  | 1500 |
| ccatttagaa | cctgggtttc | aacgctagcc | ctttctggtt | tgccataggc | cctgccaaga | 1560 |

```
tactgcaggt ccatccaggc ctctgctatc tgcatctgca gtgggcttcc caggaacttg    1620
actgtctttc atttgatctt tattttgtt tatttaatat tttaaactt attttaaaaa    1680 tatttcaaac ataagggcgg ggtgtggtgg ctcatgcctg taatcccagc actttgggag    1740
gccgaggcgg gcggatcacc tgaggccagg agttggagac cagccaggcc accatggtga    1800
aaccctgtct ctaccaaaaa tacaaaaaat tagccagata ttgtggcagg cacttttaat    1860
cccagctact cggaggctg aggcaggaga attgcttgaa cctgggaggc ggaggttgca    1920
gtgagccaag attgcaccag tgcactccag cttgggcgac agatcaagac tctgtcacac    1980
acaaaacaaa caaacaaatt tcccgtttc tctctgtccc tttctctata acatggataa    2040
aatattcacg tcttatgtat ttattattgc tgagtcattg gtgccttatt cttcagtgtt    2100
tcagtctgta tctcctaagc atcctgatgt tagttttttg actataaaat tgacctgcat    2160
tctttactag caattcaaac ggtacagcac tcttgaagtg taaacattcc tgttcctcct    2220
caccccactc tgcagacatg cctttctgtc tgtcctccca gacttttccc ctgcataaag    2280
atgttcattt tgtacataca ctcagacata catgtggctg tatttttgt taccgattt    2340 ctggatggaa tgcacactgt tatctgttta gttactttat gttttcatac aaatgacatc    2400
atcccacaaa tagaattctg ccatttaaaa aaaaaaa                              2438

<210> SEQ ID NO 5
<211> LENGTH: 2949
<212> TYPE: DNA
<213> ORGANISM: Homo sapiens

<400> SEQUENCE: 5 cgcctcccctt ccccctcccc gcccgacagc ggccgctcgg gccccggctc tcggttataa    60
gatggcggcg ctgagcggtg gcggtggtgg cggcgcggag ccgggccagg ctctgttcaa    120
cggggacatg gagcccgagg ccggcgccgg cgccggcgcc gcggcctctt cggctgcgga    180
ccctgccatt ccgaggagg tgtggaatat caaacaaatg attaagttga cacaggaaca    240
tatagaggcc ctattggaca aatttggtgg ggagcataat ccaccatcaa tatatctgga    300
ggcctatgaa gaatacacca gcaagctaga tgcactccaa caaagagaac aacagttatt    360
ggaatctctg gggaacggaa ctgatttttc tgtttctagc tctgcatcaa tggataccgt    420
tacatcttct tcctcttcta gcctttcagt gctaccttca tctctttcag ttttcaaaa    480 tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact ttgtacgaaa    780 aacgttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac cacccaat    960 accacaggaa gaggcgtcct tagcagagac tgccctaaca tctggatcat cccttccgc    1020 acccgcctcg gactctattg gccccaaat tctcaccagt ccgtctcctt caaaatccat    1080
tccaattcca cagcccttcc gaccagcaga tgaagatcat cgaaatcaat tgggcaacg    1140 agaccgatcc tcatcagctc ccaatgtgca tataaacaca atagaacctg tcaatattga    1200
tgacttgatt agagaccaag gatttcgtgg tgatggagga tcaaccacag gtttgtctgc    1260
```

```
tacccccct gcctcattac ctggctcact aactaacgtg aaagccttac agaaatctcc    1320
aggacctcag cgagaaagga agtcatcttc atcctcagaa acaggaatc gaatgaaaac    1380 acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttcccaaat tctcgcctct attgagctgc tggcccgctc    2220
attgccaaaa attaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggatttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttctttta    2880 taacaatttg gaaaatgtgg atgtctttta tttccttgaa gcaataaact aagtttcttt    2940
ttataaaaa                                                         2949
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgctcttgac ctcagactgg                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
cctcaataaa caccctacgg                                                      20

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaggctttgt cgaatcggac cggtg                                                25

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttgaacagag cctggcccgg ct                                                   22

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgtgtctgtc catctgttta acagtca                                              27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatagcctag tgcgagcaca ctctt                                                25

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccggcgatgg gctgattgtt acgaactcga gttcgtaaca atcagcccat cgttttt            57